(12) United States Patent
Kaplan et al.

(10) Patent No.: US 12,280,101 B2
(45) Date of Patent: *Apr. 22, 2025

(54) COMPOSITIONS AND METHODS FOR STABILIZATION OF ACTIVE AGENTS

(71) Applicant: Trustees of Tufts College, Medford, MA (US)

(72) Inventors: David L. Kaplan, Concord, MA (US); Fiorenzo G. Omenetto, Lexington, MA (US)

(73) Assignee: Trustees of Tufts College, Medford, MA (US)

( * ) Notice: Subject to any disclaimer, the term of this patent is extended or adjusted under 35 U.S.C. 154(b) by 38 days.

This patent is subject to a terminal disclaimer.

(21) Appl. No.: 15/858,239

(22) Filed: Dec. 29, 2017

(65) Prior Publication Data

US 2018/0360947 A1    Dec. 20, 2018

Related U.S. Application Data

(60) Continuation of application No. 15/492,363, filed on Apr. 20, 2017, now abandoned, which is a division of application No. 14/112,769, filed as application No. PCT/US2012/034643 on Apr. 23, 2012, now abandoned.

(60) Provisional application No. 61/477,737, filed on Apr. 21, 2011.

(51) Int. Cl.
| | | |
|---|---|---|
| A61K 39/20 | (2006.01) | |
| A61K 9/00 | (2006.01) | |
| A61K 9/06 | (2006.01) | |
| A61K 9/14 | (2006.01) | |
| A61K 9/19 | (2006.01) | |
| A61K 9/50 | (2006.01) | |
| A61K 9/70 | (2006.01) | |
| A61K 38/00 | (2006.01) | |
| A61K 39/00 | (2006.01) | |
| A61K 39/02 | (2006.01) | |
| A61K 39/04 | (2006.01) | |
| A61K 39/08 | (2006.01) | |
| A61K 39/09 | (2006.01) | |
| A61K 39/095 | (2006.01) | |
| A61K 39/12 | (2006.01) | |
| A61K 39/165 | (2006.01) | |
| A61K 47/42 | (2017.01) | |
| A61K 47/46 | (2006.01) | |
| B82Y 5/00 | (2011.01) | |

(52) U.S. Cl.
CPC ............ *A61K 39/20* (2013.01); *A61K 9/0019* (2013.01); *A61K 9/06* (2013.01); *A61K 9/146* (2013.01); *A61K 9/19* (2013.01); *A61K 9/5026* (2013.01); *A61K 9/5063* (2013.01); *A61K 9/7007* (2013.01); *A61K 39/0015* (2013.01); *A61K 39/02* (2013.01); *A61K 39/04* (2013.01); *A61K 39/08* (2013.01); *A61K 39/092* (2013.01); *A61K 39/095* (2013.01); *A61K 39/099* (2013.01); *A61K 39/12* (2013.01); *A61K 39/165* (2013.01); *A61K 47/42* (2013.01); *A61K 47/46* (2013.01); *B82Y 5/00* (2013.01); *A61K 38/00* (2013.01); *A61K 2039/5252* (2013.01); *A61K 2039/5254* (2013.01); *A61K 2039/6031* (2013.01); *A61K 2039/622* (2013.01); *A61K 2039/64* (2013.01); *A61K 2039/70* (2013.01); *C12N 2760/18434* (2013.01); *C12N 2760/18734* (2013.01); *C12N 2770/36234* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 3,832,253 | A | 8/1974 | Palma |
| 3,854,480 | A | 12/1974 | Zaffaroni |
| 4,452,775 | A | 6/1984 | Kent |
| 4,667,014 | A | 5/1987 | Nestor, Jr. |
| 4,675,189 | A | 6/1987 | Kent |
| 4,748,034 | A | 5/1988 | de Rham |
| 5,075,109 | A | 12/1991 | Tice |
| 5,133,974 | A | 7/1992 | Paradissis |
| 5,239,660 | A | 8/1993 | Ooi |
| 5,245,012 | A | 9/1993 | Lombari |
| 5,346,481 | A | 9/1994 | Bunin |

(Continued)

FOREIGN PATENT DOCUMENTS

| | | |
|---|---|---|
| EP | 0290197 | 11/1988 |
| EP | 0404097 | 12/1990 |

(Continued)

OTHER PUBLICATIONS

You et al. "Rapidly dissolving fibroin microneedles for transdermal drug delivery," Materials Science and Engineering C 31:1632-1636, 2011 (available online Jun. 28, 2011).*

(Continued)

*Primary Examiner* — David J Blanchard
*Assistant Examiner* — Alissa Prosser
(74) *Attorney, Agent, or Firm* — GTC Law Group PC & Affiliates

(57) ABSTRACT

Provided herein are methods and compositions for stabilization of active agents. The active agents are distributed, mixed or embedded in a silk fibroin matrix, thereby retaining the bioactivity of the active agents upon storage and/or transportation. In some embodiments, the storage-stable vaccine-silk compositions are also provided herein.

26 Claims, 22 Drawing Sheets
Specification includes a Sequence Listing.

(56) References Cited

U.S. PATENT DOCUMENTS

| | | |
|---|---|---|
| 5,407,686 A | 4/1995 | Patel |
| 5,736,152 A | 4/1998 | Dunn |
| 5,797,898 A | 8/1998 | Santini, Jr. |
| 5,900,238 A | 5/1999 | Gombotz |
| 6,669,683 B2 | 12/2003 | Santini, Jr. |
| 7,052,488 B2 | 5/2006 | Uhland |
| 7,060,260 B2 | 6/2006 | Fahnestock |
| 7,582,080 B2 | 9/2009 | Santini, Jr. |
| 7,635,755 B2 | 12/2009 | Kaplan |
| 7,842,780 B2 | 10/2010 | Kaplan |
| 8,206,774 B2 | 6/2012 | Kaplan et al. |
| 2004/0096455 A1 | 5/2004 | Maa |
| 2004/0133160 A1 | 7/2004 | Dalton |
| 2005/0112135 A1 | 5/2005 | Cormier |
| 2005/0123565 A1 | 6/2005 | Subramony |
| 2005/0255121 A1 | 11/2005 | Campbell |
| 2009/0043280 A1 | 2/2009 | Dalton |
| 2009/0142836 A1 | 6/2009 | Wang |
| 2009/0143724 A1 | 6/2009 | Cormier |
| 2009/0155330 A1* | 6/2009 | Ghartey-Tagoe .... A61B 17/205 424/422 |
| 2009/0182306 A1* | 7/2009 | Lee .................... A61M 37/0015 604/506 |
| 2009/0202614 A1* | 8/2009 | Kaplan ............... A61L 27/3604 424/443 |
| 2010/0028451 A1 | 2/2010 | Kaplan |
| 2010/0178304 A1 | 7/2010 | Wang |
| 2010/0279112 A1 | 11/2010 | Kaplan |
| 2011/0171239 A1 | 7/2011 | Kaplan |
| 2012/0052124 A1 | 3/2012 | Kaplan |
| 2014/0287043 A1 | 9/2014 | Kaplan |

FOREIGN PATENT DOCUMENTS

| | | |
|---|---|---|
| EP | 1725258 | 11/2006 |
| JP | S628054 | 1/1987 |
| JP | S6393727 | 4/1988 |
| JP | S646220 | 1/1989 |
| JP | H02311500 | 12/1990 |
| JP | H11151438 | 6/1999 |
| JP | 2000507963 | 6/2000 |
| JP | 2005097229 | 4/2005 |
| RU | 21271 | 1/2002 |
| WO | 199311161 | 6/1993 |
| WO | 1997008315 | 3/1997 |
| WO | 199828000 | 7/1998 |
| WO | 2004062697 | 7/2004 |
| WO | 2005016239 | 2/2005 |
| WO | 2005085327 | 9/2005 |
| WO | 2006062685 | 6/2006 |
| WO | WO-2006/076711 | 7/2006 |
| WO | WO-2008/118133 | 10/2008 |
| WO | 2012054582 | 4/2012 |

OTHER PUBLICATIONS

You et al. "Rapidly dissolving fibroin microneedles for transdermal drug delivery," Proceedings of the 2010 IEEE, pp. 144-147, 2010.*
Mathur et al. "Silk fibroin-derived nanoparticles for biomedical applications," Nanomedicine, 5(5):807-820, 2010.*
Wikipedia "Conjugate vaccine," last edited Dec. 18, 2019; https://en.wikipedia.org/wiki/Conjugate_vaccine.*
ip.com translation of DE-20-2011-100790, published Oct. 26, 2011, printed 2020 (Year: 2020).*
Wang et al. "In vivo degradation of three-dimensinal silk fibroin scaffolds," Biomaterials 29:3415-3428, 2008 (Year: 2008).*
Ohtake, S. et al., Arginine as a Synergistic Virucidal Agent, Molecules, 15(3): 1408-1424 (2010).
Ohtake, S. et al., Heat-stable measles vaccine produced by spray drying, Vaccine, 28(5):1275-84 (2010).
Ohtsuka, E. et al., An alternative approach to deoxyoligonucleotides as hybridization probes by insertion of deoxyinosine at ambiguous codon positions, J. Biol. Chem., 260(5): 2605-2608 (1985).
Peetermans et al., Stability of freeze-dried rubella virus vaccine (Cendehill strain) at various temperatures, 1 J. Biological Standardization 179 (1973).
Perry, H. et al., Nano- and Micropatterning of Optically Transparent, Mechanically Robust, Biocompatible Silk Fibroin Films, Advanced Materials, 20:3070-3072 (2008).
Pluckthun, The Pharmacology of Monoclonal Antibodies, vol. 113, Rosenburg and Moore eds., Springer-Verlag, New York, pp. 269-315 (1994).
Pritchard, E. et al., Silk fibroin encapsulated powder reservoirs for sustained release of adenosine, Journal of Controlled Release, 144(2):159-167 (2010).
Pritchard, E.M. et al., Physical and chemical aspects of stabilization of compounds in silk, Biopolymers, 97(6):479-498 (2012).
Rapp, F. et al., Protection of measles virus by sulfate ions against thermal inactivation, J. Bact., 90(1): 132-135 (1965).
Retraction: Applied Biological Sciences, Engineering, PNAS, 113(26): E3810, 6 pages (2016).
Rexroad, J. et al., Effect of pH and ionic strength on the physical stability of adenovirus type 5, Journal of Pharmaceutical Sciences, 95(2): 237-247 (2006).
Roberts, C.J., Non-Native Protein Aggregation Kinetics. Biotechnology and Bioengineering. 98 (5): 927-938 (2007).
Rossolini, G.M. et al., Use of Deoxyinosine-containing primers vs degenerate primers for polymerase chain reaction pased on ambiguous sequence information, Molecular and Cellular Probes, 8(2):91-98 (1994).
Russell, B. et al., The particle size of rubella virus, Journal of General Virology, 1(3): 305-310 (1967).
Santin et al. In vitro Evaluation of the Inflammatory Potential of the Silk Fibroin, J. Biomed. Mater. Res. 46:382-389 (1999).
Schalk, J.A. et al., Potency estimation of measles, mumps and rubella trivalent vaccines with quantitative PCR Infectivity assay, Biologicals, 33(2): 71-79 (2005).
Sofia, et al., Functionalized silk-based biomaterials for bone formation, Journal of Biomedical Materials Research, 54 (1):139-148 (2001).
Tsioris, K. et al., Fabrication of silk microneedles for controlled-release drug delivery, Advanced Functional Materials (2011).
Vepari, C. et al., Silk as a Biomaterial, Prog. Polym. Sci., 32(8-9): 991-1007 (2007).
Wang, X. et al., Sonication-Induced Gelation of Silk-Fibroin for Cell Encapsulation, Biomaterials, 29(8): 1054-1064 (2008).
Wang, X. et al., Silk nanospheres and microspheres from silk/pva blend films for drug delivery, Biomaterials, 31(6): 1025-1035 (2010).
Wang, X., Controlled release from multilayer silk biomaterial coatings to modulate vascular cell responses, Biomaterials, 29(7): 894-903 (2008).
Waterman, K. and Adami, R.C., Accelerated aging: Prediction of chemical stability of pharmaceuticals, International Journal of Pharmaceutics, 293(1-2): 101-125 (2005).
Wenk, et al., Silk Fibroin Spheres as a Platform for Controlled Drug Delivery, Journal of Controlled Release, 132 (1):26-34 (2008).
WHO (2006). Temperature sensitivity of vaccines. WHO publications. [Online]. The reference can be accessed at whqlibdoc.who.int/hq/2006/WHO_IVB_06.10_eng.pdf.
WHO, UNAIDA, World Bank, UNESCO, UNFPA (2000). Health: a key to prosperity. In: Success Stories in Developing Countries. World Health Organization, Geneva.
WHO. (1982). Report of Expert Committee on Biological Standardization. Thirty-second report. Requirement for measles vaccine (live). Addendum 1981, Geneva, World Health Organization. (Technical Report Series No. 673, Annex 6).
WHO. (1994). Report of Expert Committee on Biological Standardization. Requirements for measles, mumps and rubella vaccines and combined vaccines (live). Geneva, World Health Organization. (Technical Report Series, No. 840, Annex 39).
WHO. (2011). Measles. Media centre fact sheet No. 286. Oct. 2011. [online]. The reference can be accessed at who.int/mediacentre/factsheets/fs286/en/.

(56) References Cited

OTHER PUBLICATIONS

Wightman, G. et al., An investigation into the behaviors of air rifle pellets in ballistic gel and their interaction with bone, Forensic Science International, 200 (1-3): 41-49 (2007).
Wild, T.F. et al., Measles vims: both the haemagglutinin and fusion glycoproteins are required for fusion, Journal of General Virology, 72 (Pt 2): 439-442 (1991).
Woelk, C.H. et al., Increased positive selection pressure in persistent (SSPE) versus acute measles vims infections, Journal of General Virology, 83(Pt 6): 1419-1430 (2002).
Wolfson, L.J. et al., Estimating the costs of achieving the WHO-UNICEF Global Immunization Vision and Strategy, 2006-2015, Bulletin of the World Health Organization, 86(1): 27-39 (2008).
Worrall, E.E. et al., Xerovac: an ultra-rapid method for the dehydration and preservation of live attenuated Rinderpest and Peste des Petits ruminants vaccines, Vaccine, 19(7-8): 834-839 (2001).
Written Opinion for PCT/US12/34643, 5 pages (Sep. 6, 2012).
Yildirim, S. et al., Development of silk fibroin-based beads for immobilized cell fermentations, Journal of Microencapsulation, 27(1): 1-9 (2010).
Zapata, G. et al., Engineering linear F(ab')2 fragments for efficient production in *Escherichia coli* and enhanced antiproliferative activity, Protein Engineering, 8(10):1057-1062 (1995).
Zweig, S.E., Advances in vaccine stability monitoring technology, Vaccine, 24(33-34): 5977-5985 (2006).
Adu, F.D., et al., Live viral vaccine potency: an index for assessing the cold chain system, Public Health, 110(6): 325-330 (1996).
Altman, G. H. et al., Silk-based biomaterials, Biomaterials, 24:401-416 (2003).
Arora, A., et al., Micro-scale devices for transdermal drug delivery, International Journal of Pharmaceutics. 364: 227-236 (2008).
Arya, S.C., Stabilization of vaccines: to be or not to be, Vaccine, 19(4-5):595-597 (2001).
Ausar, S.F., et al., Conformational stability and disassembly of Norwalk virus like particles: effect of pH and temperature, Journal of Biological Chemistry, 281(28): 19478-19488. (2006).
Batzer, M.A. et al., Enhanced evolutionary PCR using oligonucleotides with insosine at the 3'-terminus, Nucleic Acids Research, 19(18): 5081 (1991).
Beauchamp, J. and Mansoor, O., Temperature and the storage of vaccines, New Zealand Medical Journal. 105 (931): 135 (1992).
Bishai, D.M., Vaccine storage practices in pediatric offices, Pediatrics, 89(2): 193-196 (1992).
Brandau, D.T. et al., Thermal Stability of Vaccines, Journal of Pharmaceutical Sciences, 92(2): 218-231 (2003).
Center for Disease Control (CDC) Monthly Immunization Table, 45 MMWR 24 (1996).
Chen, D. and Kristensen, D., Opportunities and challenges of developing thermostable vaccines, Expert Review of Vaccines, 8(5): 547-558 (2009).
Cheriyan, E., Monitoring the vaccine cold chain, Archives of disease in childhood, 69(5): 600-601 (1993).
Cheyne, J., Vaccine delivery management, Rev. Infect. Dis., 11(Suppl. 3): S617-S622 (1989).
Chinese Patent Office Search Report for 2012800305827, mailing date of Feb. 17, 2015, 2 pages.
Chinese Patent Office Search Report for 2015105598406, mailing date of Jul. 19, 2017, 11 pages.
Chothia, C. et al., Canonical structure for the hypervariable regions of immunoglobulins, Journal of Molecular Biology, 196(4):901-917 (1987).
Colinet G. et al., A study of the stability of a bivalent measles-mumps vaccine, Journal of Biological Standardization, 10(4): 341-346 (1982).
Creighton, T.E., Protein folding, Biochemical Journal, 270(1): 1-16 (1990).
Dorsett, P.H. et al., Structure and function of the rubella virus proteins, Reviews of Infectious Diseases, 7(1): S150-S156 (1985).
European Search Report for EP 12774253.4, 9 pages (Nov. 24, 2014).
Evans, M. and Pope, M., Vaccine handling and storage in general practice, Health Trends, 27: 124-126 (1995).
Galazka et al., Thermostability of vaccines, in Global Programme for Vaccines & Immunization (World Health Organization, Geneva, 1998).
Hall, W.W. and Martin, S.J., Purification and Characterization of Measles Virus, Journal of General Virology, 19(2): 175-188 (1973).
Health Protection Agency, Foreign travel-associated illness, England, Wales, and Northern Ireland: 2007 report. London: Health Protection Agency (2007).
Hoffman, et al., Silk Fibroin as an Organic Polymer for Controlled Drug Delivery, Journal of Controlled Release, 11 (1-2):219-227 (2006).
Holliger, P. et al, "Diabodies": small bivalent and bispecific antibody fragments, Proc. Natl. Acad. Sd. USA, 90: 6444-6448 (1993).
Horan, RL et al., In vitro degradation of silk fibroin, Biomaterials, 26(17): 3385-93 (2005).
Hu, X. et al., Effect of water on the thermal properties of silk fibroin, Thermochimica Acta, 461: 137-144 (2007).
Hubschen, J.M. et al., A multiplex TaqMan PCR assay for the detection of measles and rubella virus, J. Virol. Methods, 149(2): 246-250 (2008).
International Search Report for PCT/US12/34643, 4 pages (Sep. 6, 2012).
Jin, H.J. and Kaplan, D.L., Mechanism of silk processing in insects and spiders, Nature 424(6952):1057-1061 (2003).
Kikuchi, J. et al., Spectroscopic investigation of tertiary fold of staphylococcal protein A to expore its engineering application, Biomaterials 20(7): 647-654 (1999).
Kingston, R.L. et al., Structure of the nucleocapsid-binding domain from the mumps virus polymerase; An example of protein folding induced by crystallization, Journal of Molecular Biology, 379(4): 719-731 (2008).
Kissman, J. et al., Stabilization of measles virus for vaccine formulation, Human Vaccines. 4(5): 350-359(2008).
Koppel, D.E., Analysis of macromolecular polydispersity in intensity correlation spectroscopy: The method of cumulants, Journal of Chemical Physics, 57(11): 4814-4820 (1972).
Kubar, A. et al., Rapid and quantitative detection of mumps virus RNA by one-step real-time RT-PCR, Diagnostic Microbiology and Infectious Disease, 49(2): 83-88 (2004).
Kumakura, M., Effect of heat treatment on enzyme entrapped into polymer gels, Journal of Molecular Catalysis B: Enzymatic, L1-L6 (1995).
Lee, S. et al., Chemical instability of protein pharmaceuticals: mechanisms of oxidation and strategies of stabilization, Biotechnology and Bioengineering, 48(5): 490-500 (1994).
Liddle, J.L.M. and Harris, M.F., How general practitioners store vaccines. A survey in south-western Sydney, The Medical Journal of Australia, 162: 366-368 (1995).
Lu, S. et al., Stabilization of Enzymes in Silk Films, Biomacromolecules, 10(5): 1032-1042 (2009).
Lucas et al., "The silk fibroins." Advances in protein chemistry. vol. 13. Academic Press, 1958. 107-242.
Malvoisin, E. and Wild T.F., Measles virus glycoproteins: studies on the structure and interaction of the haemagglutinin and fusion proteins, Journal of General Virology, 74(Pt 11): 2365-2372 (1993).
Manning, M.D. and Borchardt, P.K., Stability of pharmaceutical proteins, Pharmaceutical Research, 6(11): 903-918 (1989).
McAleer, W.J. et al., Stability on storage at various temperatures of live measles, mumps and rubella virus vaccines in new stabilizer, 8(4): 281-287 (1980).
Middaugh, C.R., Formulation and delivery of biopharmaceuticals, Journal of Pharmaceutical Sciences, 85: 1259-1260 (1996).
Mirchamsy et al., Stabilizing effect of magnesium chloride and sucrose on Sabin live polio vaccine, 41 Devel. Biol. Standardization 255 (1978).
Moss, W.J. and Gliffin, D.E., Global measles elimination, Nature Review Microbiology, 4(12): 900-908 (2006).
Murphy, A.R. et al., Modification of Silk Fibroin Using Diazonium Coupling Chemistry and the Effects on hMSC Proliferation and Differentiation, Biomaterials, 29(19):2829-2838 (2008).

(56) References Cited

OTHER PUBLICATIONS

Nakhasi, H.L. et al., Specific binding of host cell proteins to the 3'-terminal stem-loop structure of rubella virus negative-strand RNA, Journal of Virology, 65(11): 5961-5967 (1991).

* cited by examiner

AGGREGATED VIRAL PARTICLES

SILK-ENTRAPPED VIRAL PARTICLES

F

SEQUENCE LISTING

<160> NUMBER OF SEQ ID NOS: 9

<210> SEQ ID NO 1
<211> LENGTH: 24

```
<212> TYPE: DNA
<213> ORGANISM: Artificial Sequence
<220> FEATURE:
<223> OTHER INFORMATION: synthetic primer

<400> SEQUENCE: 1
ccctgaggga ttcaacatga ttct                                        24

<210> SEQ ID NO 2
<211> LENGTH: 23
<212> TYPE: DNA
<213> ORGANISM: Artificial Sequence
<220> FEATURE:
<223> OTHER INFORMATION: synthetic primer

<400> SEQUENCE: 2
atccaccttc ttagctccga atc                                         23

<210> SEQ ID NO 3
<211> LENGTH: 24
<212> TYPE: DNA
<213> ORGANISM: Artificial Sequence
<220> FEATURE:
<223> OTHER INFORMATION: synthetic primer

<400> SEQUENCE: 3
tcttgctcgc aaaggcggtt acgg                                        24

<210> SEQ ID NO 4
<211> LENGTH: 22
<212> TYPE: DNA
<213> ORGANISM: Artificial Sequence
<220> FEATURE:
<223> OTHER INFORMATION: synthetic primer

<400> SEQUENCE: 4
tgatacccag acctgtgttc ac                                          22

<210> SEQ ID NO 5
<211> LENGTH: 20
<212> TYPE: DNA
<213> ORGANISM: Artificial Sequence
<220> FEATURE:
<223> OTHER INFORMATION: synthetic primer

<400> SEQUENCE: 5
ggtcgatgag gacgtgtagg                                             20

<210> SEQ ID NO 6
<211> LENGTH: 22
<212> TYPE: DNA
<213> ORGANISM: Artificial Sequence
<220> FEATURE:
<223> OTHER INFORMATION: synthetic primer

<400> SEQUENCE: 6
gatcacccag cactccacgc aa                                          22

<210> SEQ ID NO 7
<211> LENGTH: 18
<212> TYPE: DNA
<213> ORGANISM: Artificial Sequence
<220> FEATURE:
<223> OTHER INFORMATION: synthetic primer

<400> SEQUENCE: 7
```

```
cataggagat atgtgggg                                                      18

<210> SEQ ID NO 8
<211> LENGTH: 26
<212> TYPE: DNA
<213> ORGANISM: Artificial Sequence
<220> FEATURE:
<223> OTHER INFORMATION: synthetic primer

<400> SEQUENCE: 8
gtcttcgcca acgatggtga tgattg                                             26

<210> SEQ ID NO 9
<211> LENGTH: 30
<212> TYPE: DNA
<213> ORGANISM: Artificial Sequence
<220> FEATURE:
<223> OTHER INFORMATION: synthetic primer

<400> SEQUENCE: 9
ccatgcaggc ggtcacattc cgacaactgc                                         30
```

COMPOSITIONS AND METHODS FOR STABILIZATION OF ACTIVE AGENTS

CROSS REFERENCE TO RELATED APPLICATIONS

This Application claims the benefit under 35 U.S.C § 119(e) of U.S. Provisional Application No. 61/477,737, filed Apr. 21, 2011, which is herein incorporated by reference in its entirety.

GOVERNMENT SUPPORT

This invention was made with Government support under grants EB002520 awarded by the National Institutes of Health and FA9550-07-1-0079 awarded by the US Air Force. The Government has certain rights in the invention.

TECHNICAL FIELD

The present invention generally relates to methods and compositions for stabilization of active agents.

BACKGROUND

Stabilization of active agents is a critical feature of many applications, because the active agents are usually labile and sensitive to changes in surrounding conditions, e.g., temperature, humidity and/or light. Even if an active agent is identified to be useful for a given reaction, its application is often hampered by a lack of long-term stability under process conditions.

Various modes to stabilize active agents, e.g., enzymes and therapeutic proteins, have been studied, from lyophilization to covalent immobilization, for different applications. In general, many immobilized active agents demonstrate improved stability, likely due to reduce mobility to prevent changes in hydrophobic hydration and thus aggregation and loss of activity. Techniques for immobilization of active agents, e.g., enzymes, usually fall into four categories: (1) noncovalent adsorption of enzymes to carrier material surfaces; (2) covalent attachment to material surfaces; (3) physical entrapment into a material matrix; and (4) crosslinking of an enzyme to "lock" the structure. All these approaches are a compromise between maintaining high catalytic activity while achieving the advantages listed above. The lack of materials that provide specific surface binding sites or relative hydrophilic/hydrophobic microenvironments for the retention of high loading and activity of active agents limits the application of the above carrier-based immobilization approaches. Further, for many applications, carrier materials need to be biodegradable and biocompatible for biomedical applications, which rules out the use of most synthetic polymer materials.

Recently, new immobilization approaches have been developed to improve stability and activity of active agent, e.g., enzymes. For example, the microenvironment of the carrier material may be engineered by using blocking agents to reduce non-specific binding sites. Alternatively, hydrophilic macromolecules may be introduced proximal to the active agent, or hydrophilic spacers used between the active agent and the material surface. Further, sol-gel materials have been used for immobilization and found to enhance the activity of enzymes, e.g., lipases, up to 100-fold due to the effects of microenvironmental confinement.

Further, enzyme cross-linking methods have been combined with protein crystallization to generate cross-linked enzyme crystals (CLECs) with increased enzyme stability and selectivity when compared to the native enzyme. While this method has been used by pharmaceutical companies to formulate therapeutic protein drugs, protein crystallization is complicated and often unpredictable. Cross-linked enzyme aggregates (CLEAs) can be obtained by precipitation of proteins followed by cross-linking with glutaraldehyde. The CLEA from penicillin acylase had the same activity as a CLEC in the synthesis of ampicillin. Magnetic nanoparticles have also been used for covalent immobilization of enzymes and thus enhancement of enzyme stability. Yet none of these immobilization methods are biocompatible/biodegradable or simple to use while providing stability under ambient storage conditions (e.g., room temperature) for long periods of time.

In particular, vaccine stabilization has been a long-lasting challenge and large amounts of vaccines have been wasted due to improper storage. Although global immunization currently saves the lives of 2-3 million children every year, of the 10.5 million child deaths that occur annually, 2.5 million are due to diseases that are preventable by vaccines. Measles, mumps, and rubella are three common childhood diseases, caused by measles virus, mumps virus (paramyxoviruses), and rubella virus (togavirus), respectively, that may be associated with serious complications and/or death. For example, pneumonia and encephalitis are caused by measles. Mumps is associated with aseptic meningitis, deafness and orchitis; and rubella during pregnancy may cause congenital rubella syndrome in the infants of infected mothers. The impact of measles, mumps, and rubella vaccination on the natural history of each disease in the U.S. can be quantified by comparing the maximum number of measles, mumps, and rubella cases reported in a given year prior to vaccine use to the number of cases of each disease reported in 1995. For measles, 894,134 cases reported in 1941 compared to 288 cases reported in 1995 resulted in a 99.97% decrease in reported cases; for mumps, 152,209 cases reported in 1968 compared to 840 cases reported in 1995 resulted in a 99.45% decrease in reported cases; and for rubella, 57,686 cases reported in 1969 compared to 200 cases reported in 1995 resulted in a 99.65% decrease. *Monthly Immunization Table,* 45 MMWR 24 (1996).

Vaccines are biological substances that may lose their effectiveness quickly if they become too hot or too cold, especially during transport and storage. Inadvertent freezing, heating above 8° C. or other breaks in the cold chain may result in either failure of efficacy or vaccine wastage. According to the WHO, between 2006-2015, the U.S. alone will have contributed $35 billion for global vaccination programs. About one third will be spent on vaccines and remainder will be spent on vaccine delivery systems. It is clear that even 1% vaccine wastage because of cold chain failure is a considerable sum. Indeed, for five U.S. states, the average wastage of 1% to 5% cost approximately $6-$31 million. In other parts of the world, vaccine wastage can reach 10%. The two most common forms of wastage relate to heat stability and shelf life, with inadvertent freezing remaining another key problem. Hence, there is a great need for storage-stable active agents, e.g., storage-stable vaccines, with longer shelf life that can maintain efficacy under various robust environmental conditions, e.g., without requiring cold chain compliance.

SUMMARY

Various embodiments described herein provide for a storage-stable composition comprising a silk fibroin matrix and an active agent distributed therein, wherein the active agent retains at least about 30% of its original bioactivity when the composition is subjected to at least one state-changing cycle, and/or is maintained for a period of time under a specified condition. In one embodiment, the state-changing cycle is a freeze-thaw cycle. In one embodiment, the period of time for maintaining the active agent is at least about 24 hours. In some embodiments, the specified condition can be an environmental condition under which an active agent is stored and/or transported. Non-limiting examples of environmental conditions include temperatures, air pressures, humidity, and light exposure. In some embodiments, the active agent is an immunogen. In some embodiments, the active agent is a vaccine.

Kits and delivery devices, e.g., useful in biomedical fields, are also provided herein. Exemplary delivery devices include, but are not limited to, syringes, dry powder injectors, nasal sprays, nebulizers, and implants. Such kits and devices comprise a storage-stable composition described herein, and optionally a pharmaceutically acceptable solution. In one embodiment, the kit further includes at least one delivery device for administering to a subject a storage-stable composition described herein, and/or a disinfectant.

FIG. 4 is a bar graph comparing initial recovered potency of measles, mumps, and rubella virus in silk films with the addition of the stabilizing additives $MgCl_2$, $MgSO_4$ and sucrose. N=3, error bars represent standard deviations.

FIG. 5 shows reconstituted MMR vaccine at 24, 18, 12 and 6 hours in 70% sucrose prior to cell inoculation stored at 25° C. protected from light. N=3, error bars represent standard deviations.

FIGS. 6A-6D present comparisons of residual potency of reconstituted MMR vaccine in water at 4° C. (FIG. 6A) or 37° C. (FIG. 6C), or 70% sucrose at 4° C. (FIG. 6B) or 37° C. (FIG. 6D). Vaccines were reconstituted at 24, 18, 12 and 6 hours in water or 70% sucrose prior to cell inoculation stored at 25° C. protected from light. N=3, error bars represent standard deviations.

FIG. 7 shows a schematic of vaccine-encapsulated silk film fabrication and infectivity assay. (1) Lyophilized vaccine powder is reconstituted in sterilized aqueous silk solution. (2a) Vaccine-encapsulated silk films were prepared by casting an aliquot of the vaccine-silk mixture onto a Teflon-coated surface and allowed to dry in a sterile hood for 12 hours at room temperature, protected from light. (3a) Individual dried films were stored in Eppendorf tubes at the appropriate temperatures for stability studies. (2b) After lyophilized vaccine powder was reconstituted in sterilized aqueous silk solution, lyophilized vaccine-encapsulated silk films were prepared by casting an aliquot of vaccine-silk mixture into a 96-well plate and lyophilized. (3b) Individual lyophilized films were removed from the well plate and transferred to glass serum vials, capped with a lyophilization stopper and alum seal under nitrogen and vacuum conditions. (4) For infectivity studies, the films were redissolved in nuclease-free sterile water and the solution was added directly to Vero cells grown in M199 media cultured in a 24-well plate. The cells were incubated for 3 days to allow the virus to replicate, then the RNA was isolated, converted to cDNA and quantitated using real-time PCR. (5) RNA was isolated from the Vero cells using TRIzol/chloroform, the RNA was purified and reverse transcription was carried out to synthesize cDNA for real-time R T-PCR.

FIGS. 8A-8C show graphs of residual potency of measles, mumps and rubella components of the lyophilized vaccine reconstituted in water for different times, stored at 4° C. (FIG. 8A), 25° C. (FIG. 8B) and 37° C. (FIG. 8C) (+) measles, (o) mumps, (•) rubella. N=3, error bars represent standard deviations.

FIGS. 9A-9D show graphs of the stability of the measles virus component of the MMR vaccine stored in 9% (w/v) silk films over 6 months at 4° C. (FIG. 9A), 25° C. (FIG. 9B), 37° C. (FIG. 9C), and 45° C. (FIG. 9D). (+) MMR-silk films. (o) MMR powder. N=3, error bars represent standard deviations.

FIGS. 10A-10D show graphs of the stability of the mumps virus component of the MMR vaccine stored in 9% (w/v) silk films over 6 months at 4° C. (FIG. 10A), 25° C. (FIG. 10B), 37° C. (FIG. 10C), and 45° C. (FIG. 10D). (+) MMR-silk films. (o) MMR powder. N=3, error bars represent standard deviations.

FIGS. 11A to 11D shows graphs of the stability of the rubella virus component of the MMR vaccine stored in 9% (w/v) silk films over 6 months at 4° C. (FIG. 11A), 25° C. (FIG. 11B), 37° C. (FIG. 11C), and 45° C. (FIG. 11D). (+) MMR-silk films. (o) MMR powder. N=3, error bars represent standard deviations.

FIGS. 12A to 12D show graphs of the stability of the measles virus component of the MMR vaccine stored in 9% (w/v) lyophilized silk films over 6 months at 4° C. (FIG. 12A), 25° C. (FIG. 12B), 37° C. (FIG. 12C), and 45° C. (FIG. 12D). (+) MMR-silk lyophilized films. (o) MMR powder. N=3, error bars represent standard deviations.

FIGS. 13A-13D show graphs of the stability of the mumps virus component of the MMR vaccine stored in 9% (w/v) lyophilized silk films over 6 months at 4° C. (FIG. 13A), 25° C. (FIG. 13B), 37° C. (FIG. 13C), and 45° C. (FIG. 13D). (+) MMR-silk lyophilized films. (o) MMR powder. N=3, error bars represent standard deviations.

FIGS. 14A-14D show graphs of the stability of the rubella virus component of the MMR vaccine stored in 9% (w/v) lyophilized silk films over 6 months at 4° C. (FIG. 14A), 25° C. (FIG. 14B), 37° C. (FIG. 14C), and 45° C. (FIG. 14D). (+) MMR-silk lyophilized films. (o) MMR powder. N=3, error bars represent standard deviations.

FIGS. 15A-15C show Arrhenius plots of the degradation rates of the measles (FIG. 15A), mumps (FIG. 15B) and rubella (FIG. 15C) components of the vaccine as a function of the inverse of the absolute temperature. (+) lyophilized silk films, (o) silk films, (•) powder.

FIGS. 16A-16C show graphs of the predicted half-lives of the measles (FIG. 16A), mumps (FIG. 16B) and rubella (FIG. 16C) viral components as a function of temperature and the corresponding upper and lower limits of the half-life. The predicted half-lives represent the estimated time required for the viral component to degrade to 50% of the initial value. (+) lyophilized silk films, (o) silk films, (•) powder FIG. 17 shows a graph of differential scanning calorimetry, solid-state DSC. Solid-state DSC of a lyophilized silk film shows glass transition (Tg) at 178° C. The Tg of the manufacturer provided MMR vaccine powder (containing a wide variety of excipients and stabilizers) was 68.9° C. The lyophilized MMR-silk films showed a Tg at 89.2° C., indicating the addition of silk to the MMR powder increased stability of the vaccine reflected in the increased Tg. The MMR-silk lyophilized film curve, however, showed two peaks at 116.6° C. and 164.8° C. which could indicate a Tm and Td, describing the unfolding or degradation of vaccine components.

Figure 18:
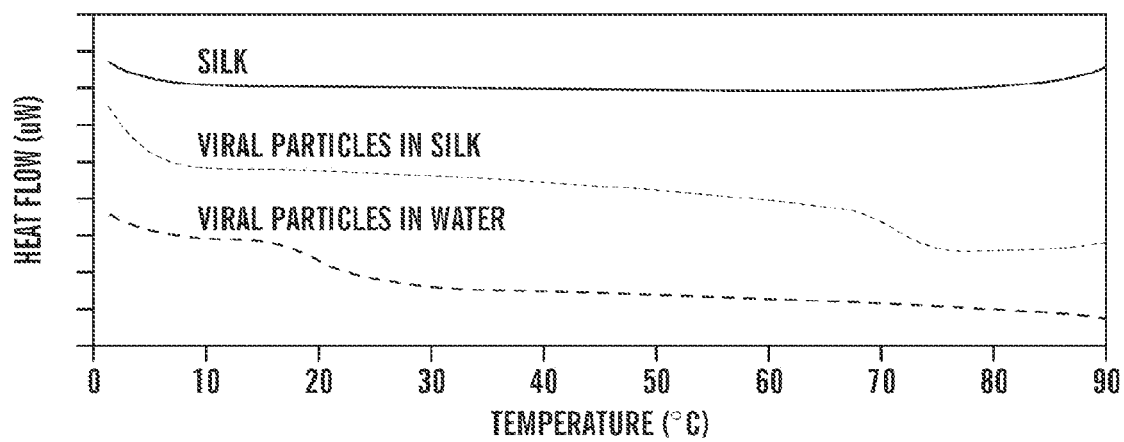

FIG. 18 shows a graph of nano differential scanning calorimetry, nano-DSC. The Tm of purified viral particles appears around 16.8° C. The presence of silk increases the Tm of the viral particles to 68.3° C. The sharp drop following the Tm is an exothermic event most likely due to aggregation as a result of the protein unfolding at the Tm. The Tg of silk was around 178° C. so the elevated Tg values were due to the effect silk has on the encapsulated viral proteins.

Figure 19:
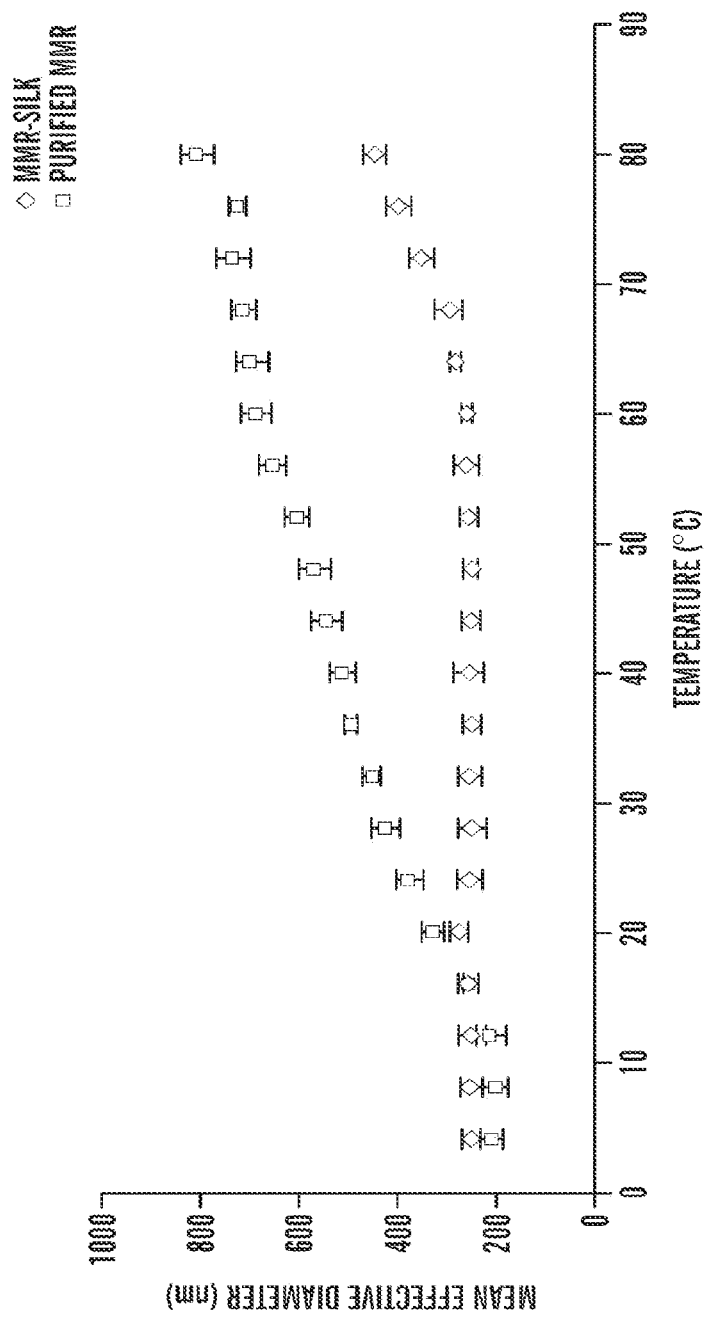

FIG. 19 shows a graph indicating comparison of dynamic light scattering of purified viral particles in water and purified viral particles in silk solution. The average mean effective diameter of MMR viral particles was about 250 nm. The mean effective diameter of the purified MMR solution began increasing at around 16° C., indicating aggregation of viral particles due to the increased thermal input. The MMR-silk solution did not show signs of aggregation until 70° C., indicating silk provided the structural stability to prevent the aggregation of the viral proteins.

Figure 20A:
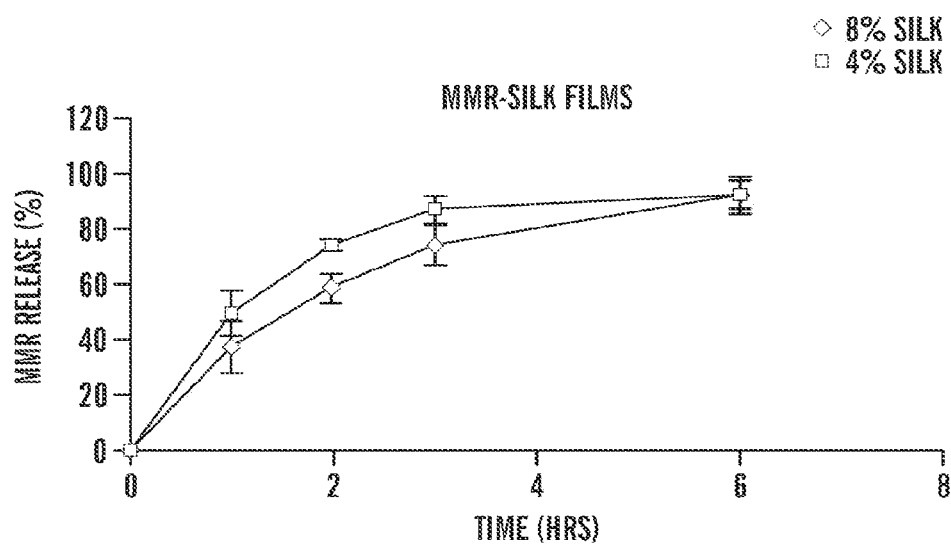
Figure 20B:
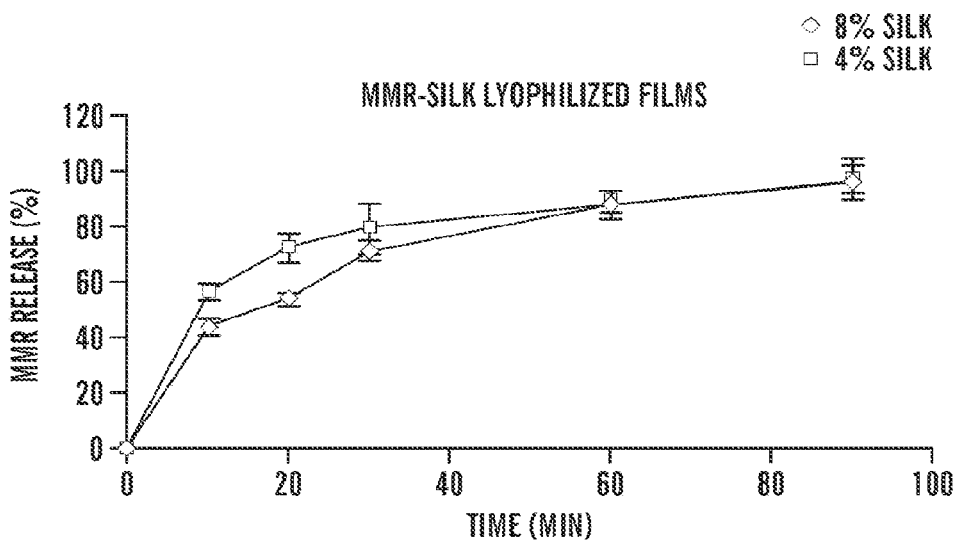

FIGS. 20A-20B show graphs of MMR release from (FIG. 20A) silk films and (FIG. 20B) lyophilized silk films. N=3, error bars represent standard deviations.

Figure 21A:
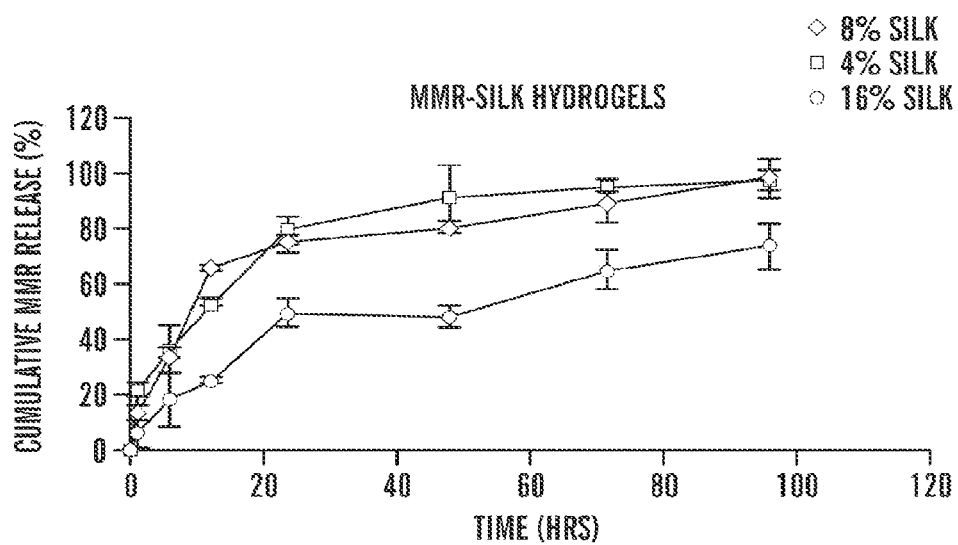
Figure 21B:
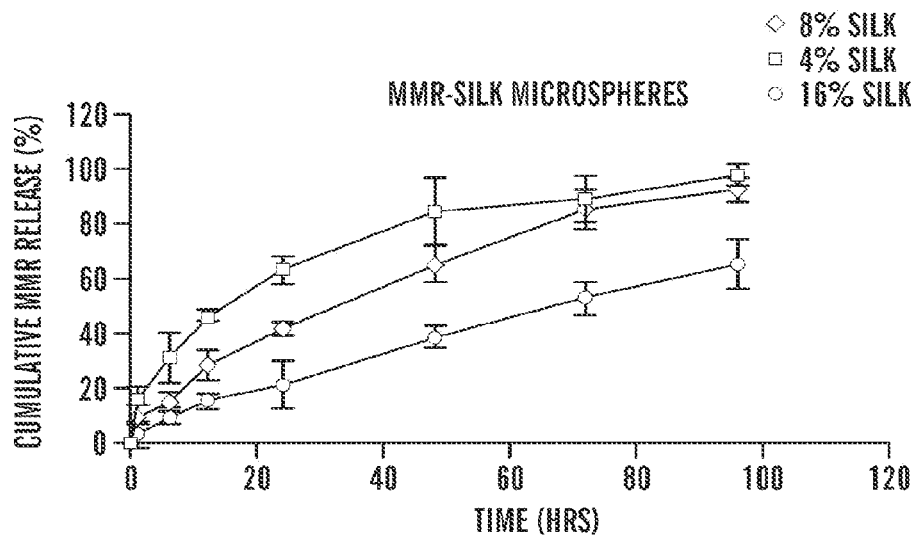

FIGS. 21A-21B show graphs of MMR release (FIG. 21A) silk hydrogels and (FIG. 21B) silk microspheres. N=3, error bars represent standard deviations.

Figure 22D:
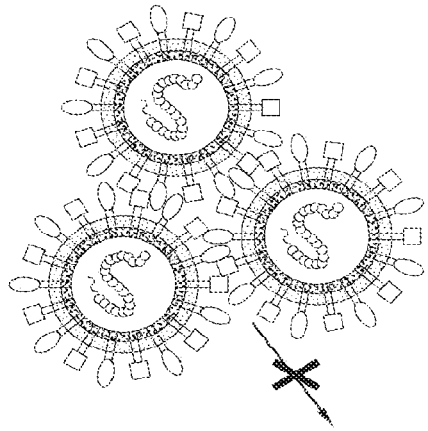
Figure 22B:
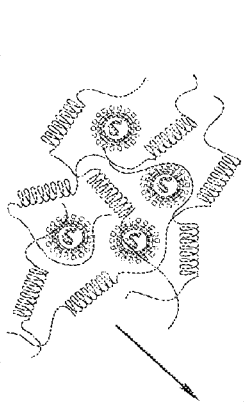

FIGS. 22A-22D show schematic diagrams. FIG. 22A, measles and mumps belong to the Paramyxoviridae family and their structures consist of single-stranded, negative-sense RNA enclosed in nucleocapsids within a lipid bilayer. The viral envelop is formed by the matrix protein (M), haemaglutinin protein (H) and fusion protein (F). Structurally intact Hand F proteins are responsible for binding and fusion of the viral particles to the animal cells. FIG. 22B, by a combination of hydrophobic interaction and limited chain mobility, silk-entrapped viral particles maintain structural activity at elevated temperatures. FIG. 22C, the F and H proteins binding to the receptors CD46 and CD150 (collectively known as SLAM) to gain entry into the cell to initiate viral replication. FIG. 22D, denaturation of the surface proteins can cause aggregation of the viral particles. The perturbation of the proteins can cause it to be unrecognized by the cell and denied entry.

DETAILED DESCRIPTION

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

One aspect provided herein relates to methods and compositions of maintaining or stabilizing the bioactivity of an active agent. The method includes maintaining a composition, wherein the composition comprises a silk fibroin matrix and at least one active agent distributed, mixed, or embedded therein, and wherein the at least one active agent retains or stabilizes at least about 30% of its original bioactivity when the composition is subjected to a specified condition, which inhibits or reduces the bioactivity of the active agent, for a period of time. Such conditions can include, but are not limited to, a state-changing cycle, temperatures, air pressures, humidity, and light exposure. In one embodiment, the state-changing cycle is a freeze-thaw cycle.

Embodiments of various aspects described herein provide for stabilized active agents, in which stabilization of an active agent is achieved by distributing, mixing, or embedding an active agent in a silk fibroin matrix. The silk fibroin matrix can be a silk fibroin solution or a solid-state silk fibroin matrix. This approach provides for the active agent to retain bioactivity regardless of the cold chain and/or environmental conditions under which the active agent is stored and/or transported. Exemplary environmental conditions include, but are not limited to, temperatures, air pressures, humidity, and light exposure. For example, the cold chain is a standard practice for stabilizing active agents in the pharmaceutical industry: maintaining the cold chain ensures that active agents are transported and stored according to the manufacturer's recommended temp range (e.g., 2° C. to 8° C. or sub-zero temperatures) until time of use.

In certain embodiments, the active agents described herein are immunogens. In one embodiment, the immunogen is a vaccine. Most vaccines are sensitive to environmental conditions under which they are stored and/or transported. For example, freezing may increase reactogenicity (e.g., capability of causing an immunological reaction) and/or loss of potency for some vaccines (e.g., HepB, and DTaP/IPV/HIB), or cause hairline cracks in the container, leading to contamination. Further, some vaccines (e.g., BCG, Varicella, and MMR) are sensitive to heat. Many vaccines (e.g., BCG, MMR, Varicella, Meningococcal C Conjugate, and most DTaP-containing vaccines) are light-sensitive. See, e.g., Galazka et al., *Thermostability of vaccines*, in Global Programme for Vaccines & Immunization (World Health Organization, Geneva, 1998); Peetermans et al., *Stability of freeze-dried rubella virus vaccine (Cendehill strain) at various temperatures*, 1 J. Biological Standardization 179 (1973). Thus, the compositions and methods described herein also provide for stabilization of vaccines regardless of the cold chain and/or other environmental conditions.

Stabilization of Active Agents

The terms "stabilizing," "stabilize," "stability," and "stabilization," are used herein in reference to maintaining or retaining bioactivity of at least one active agent in a silk fibroin matrix. The phrase "stabilization of active agents" as used herein means that one or more active agents distributed, mixed or embedded in a silk fibroin matrix retain at least about 30% of its original bioactivity, including at least about 40%, at least about 50%, at least about 60%, at least about 70%, at least about 80%, at least about 90% of its original bioactivity or higher. The terms "stabilize" and "retain" in reference to bioactivity of active agents are used herein interchangeably.

As used herein, the terms "maintaining," "maintain," and "maintenance," when referring to compositions or active agents mean keeping, sustaining, or retaining the bioactivity of at least one active agent in a silk fibroin matrix, when the active agent is subjected to certain conditions. In some embodiments, one or more active agents distributed in a silk fibroin matrix retains at least about 30% of its original bioactivity, including at least about 40%, at least about 50%, at least about 60%, at least about 70%, at least about 80%, at least about 90% of its original bioactivity or higher.

The term "bioactivity," as used herein in reference to an active agent, generally refers to the ability of an active agent to interact with a biological target and/or to produce an effect on a biological target. For example, bioactivity can include, without limitation, elicitation of a stimulatory, inhibitory, regulatory, toxic or lethal response in a biological target. The biological target can be a molecule or a cell. For example, a bioactivity can refer to the ability of an active agent to modulate the effect/activity of an enzyme, block a receptor, stimulate a receptor, modulate the expression level of one or more genes, modulate cell proliferation, modulate cell division, modulate cell morphology, or any combination thereof. In some instances, a bioactivity can refer to the ability of a compound to produce a toxic effect in a cell.

The bioactivity can be determined by assaying a cellular response. Exemplary cellular responses include, but are not limited to, lysis, apoptosis, growth inhibition, and growth promotion; production, secretion, and surface exposure of a protein or other molecule of interest by the cell; membrane surface molecule activation including receptor activation; transmembrane ion transports; transcriptional regulations; changes in viability of the cell; changes in cell morphology; changes in presence or expression of an internal component of the cell; changes in presence or expression of a nucleic acid produced within the cell; changes in the activity of an enzyme produced within the cell; and changes in the presence or expression of a receptor. Methods for assaying different cellular responses are well known to one of skill in the art, e.g., western blot for determining changes in presence or expression of an endogenous protein of the cell, or microscopy for monitoring the cell morphology in response to the active agent.

In reference to an antibody, the term "bioactivity" includes, but is not limited to, epitope or antigen binding affinity, the in vivo and/or in vitro stability of the antibody, the immunogenic properties of the antibody, e.g., when administered to a human subject, and/or the ability to neutralize or antagonize the bioactivity of a target molecule in vivo or in vitro. The aforementioned properties or characteristics can be observed or measured using art-recognized techniques including, but not limited to, scintillation proximity assays, ELISA, ORIGEN immunoassay (IGEN), fluorescence quenching, fluorescence ELISA, competitive ELISA, SPR analysis including, but not limited to, SPR analysis using a BIAcore biosenser, in vitro and in vivo neutralization assays (see, for example, International Publication No. WO 2006/062685), receptor binding, and immunohistochemistry with tissue sections from different sources including human, primate, or any other source as needed. In reference to an immunogen, the "bioactivity" includes immunogenicity, the definition of which is discussed in detail later. In reference to a virus, the "bioactivity" includes infectivity, the definition of which is discussed in detail later. In reference to a contrast agent, e.g., a dye, the "bioactivity" refers to the ability of a contrast agent when administered to a subject to enhance the contrast of structures or fluids within the subject's body. The bioactivity of a contrast agent also includes, but is not limited to, its ability to interact with a biological environment and/or influence the response of another molecule under certain conditions.

By "original bioactivity" in reference to an active agent is generally meant the bioactivity of an active agent as measured immediately before or immediately after the active agent is introduced into a silk fibroin matrix. That is, the original bioactivity of an active agent can be measured, for example, within about 20 minutes, before or after the active agent is introduced into a silk fibroin matrix. In some instances, the original bioactivity of an active agent can be measured, for example, about 10 seconds, about 15 seconds, about 20 seconds, about 25 seconds, about 30 seconds, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, or about 20 minutes, before or after the active agent is introduced into a silk fibroin matrix. In one embodiment, the silk fibroin matrix is a solid-state silk fibroin matrix. In such embodiment, an active agent can lose some of its bioactivity during handling before it is distributed into a solid-state silk fibroin matrix. In another embodiment, the term "original bioactivity," as used herein, can be used to describe the bioactivity of an active agent before the active agent is introduced into a silk-fibroin matrix. In some embodiments, the term "original bioactivity" refers to the maximum bioactivity of an active agent, e.g., bioactivity measured immediately after activation of the active agent, e.g., by reconstitution or by increasing the temperature. For example, if the active agent is initially in powder, the original bioactivity of the active agent can be measured immediately after reconstitution. In some embodiments, the term "original bioactivity" refers to bioactivity of an active agent when stored or transported in the absence of a silk fibroin matrix under conditions specified by the manufacturer. In some embodiments, the term "original bioactivity" refers to bioactivity of an active agent when stored or transported in a storage-stable composition as described herein under conditions specified by the manufacturer. The definitions of the term "original bioactivity" described herein are also applied to the terms "original immunogenicity" and "original infectivity" as used later herein.

In accordance with the methods described herein, distributing, mixing, or embedding an active agent in a silk fibroin matrix retains or stabilizes the bioactivity of the active agent, e.g., at least about 30% of its original bioactivity, regardless of the environmental or storage conditions (e.g., state-changing cycles, temperature, humidity, or light exposure). The silk fibroin matrix can be in solution or in a solid state. In various embodiments, when an active agent is distributed in a silk fibroin matrix and such composition is subjected to a state-changing cycle and/or is maintained for a period of time under a specified condition, the active agent can retain at least about 30% of its original bioactivity e.g., at least about 40%, at least about 50%, at least about 60%, at least about 70%, at least about 80%, at least about 90%, at least about 95% of the original bioactivity or higher. In one embodiment, the active agent can retain at least about 80% of its original bioactivity. Stated another way, the stability of an active agent in a silk fibroin matrix (i.e., the ability of an active agent to retain its bioactivity (e.g., at least about 30% of its original bioactivity) in a silk fibroin matrix) can be increased by at least about 30%, at least about 40%, at least about 50%, at least about 60%, at least about 70%, at least about 80%, at least about 90%, at least about 95%, relative to the stability of an active agent in the absence of a silk fibroin matrix. In one embodiment, the active agent can retain at least about 80% of its original bioactivity.

The compositions described herein can be maintained for any period of time, e.g., hours, days, weeks, months or years. In some embodiments, the compositions described herein can be maintained at a temperature above 0° C. for at least about 3 hours, at least about 6 hours, at least about 9 hours, at least about 12 hours, at least about 24 hours or longer. In some embodiments, the compositions described herein can be maintained for at least about 1 day, at least about 2 days, at least about 3 days, at least about 4 days, at least about 5 days, at least about 6 days, at least about 7 days or longer. In some embodiments, the compositions described herein can be maintained for at least about 1 week, at least about 2 weeks, at least about 3 weeks, at least about 4 weeks or longer. In some embodiments, the compositions described herein can be maintained for at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months or longer.

In methods and compositions described herein, the compositions described herein can be maintained at any temperatures or at a manufacturer's recommended temperature specified for an active agent. In some embodiments, the compositions can be maintained in liquid nitrogen or in dry ice. In some embodiments, the compositions can be maintained, for example, between about −80° C. and about −20° C., inclusive, or between about −20° C. and about 0° C., inclusive. In some embodiments, the compositions can be maintained at a temperature above 0° C. In those embodiments, the compositions can be maintained at a temperature from about 0° C. to about an ambient temperature. As used herein, the term "ambient temperature" is used to describe a surrounding temperature at which the compositions described herein are maintained and it includes temperatures between 0° C. and 60° C., between 0° C. and 50° C., or between 0° C. and 40° C. In some embodiments, the ambient temperature is the fridge temperature (e.g., between 0° C. and 15° C., inclusive). In some embodiments, the ambient temperature is about the body temperature of a subject (e.g., between 36° C. and 38° C., inclusive, for a human subject, or a higher or lower body temperature range for other animals). In some embodiments, the ambient temperature is the room temperature, e.g., between 20° C. and 35° C., and it can vary with geographical conditions. For example, the room temperature in warm-climate regions, e.g., Africa, can be generally warmer than that in cool-climate regions, e.g., the United States or United Kingdom. In some embodiments, the compositions can be maintained at a temperature of at least about 37° C. or greater than 37° C. In some embodiments, the compositions can be maintained at a temperature of at least about 40° C. or greater than 40° C. In some embodiments, the compositions can be maintained at a temperature of at least about 45° C. or greater than 45° C.

Some embodiments described herein are beneficial for development of implantable drug delivery devices in which an active agent can retain at least 30% (including at least about 40%, at least about 60%, at least about 80% or higher) of its original bioactivity or higher for a period of time. In some embodiments, a composition or an active agent in an implantable drug device can retain at least about 30% of its original bioactivity or higher for at least about 6 hours, at least about 12 hours, at least about 24 hours, at least about 36 hours, at least about 48 hours, at least 3 days, at least about 4 days, at least about 5 days, at least about 6 days, at least about 1 week, at least about 2 weeks, at least about 3 weeks, at least about 4 weeks, at least about 2 months, at least about 3 months, at least about 4 months, at least about 5 months, at least about 6 months, or at least after 1 year or longer, after implantation.

In some embodiments, one or more active agents, e.g., immunogens such as vaccines, encapsulated in an injectable form of silk fibroin matrix (e.g., but not limited to, hydrogel, gel-like particles, and/or microspheres) can be administered to a subject (e.g., by injection such as subcutaneous injection) as a depot of the active agent (e.g., a vaccine depot) such that the active agent (e.g., a vaccine) can be released, continuously or intermittently, from the depot for an extended period of time, e.g., for a period of hours, days, weeks, or months. In some embodiments, the active agent (e.g., a vaccine) can be released at a rate at which at least about 1% (including at least about 5%, at least about 10%, at least about 20%, at least about 30%, at least about 40%, at least about 50%, at least about 60%, at least about 70%, at least about 80%, at least about 90%, at least about 95%, or more) of the encapsulated active agent is released over a period of at least 1 hour, at least 2 hours, at least 3 hours, at least about 4 hours, at least about 5 hours, at least about 6 hours, at least about 12 hours, at least about 24 hours or longer. In some embodiments, the active agent (e.g., a vaccine) can be released at a rate at which at least about 10% (including at least about 20%, at least about 30%, at least about 40%, at least about 50%, at least about 60%, at least about 70%, at least about 80%, at least about 90%, at least about 95%, or more) of the encapsulated active agent is released over a period of 5 days, a period of 1 week, at least about 2 weeks, at least about 3 weeks, at least about 1 month, at least about 2 months, at least about 3 months or longer.

In some embodiments, the active agent retains at least about 30% of its original bioactivity e.g., at least about 40%, at least about 50%, at least about 60%, at least about 70%, at least about 80%, at least about 90%, at least about 95% of the original bioactivity or higher activity at about 4° C., at about 25° C., at about 37° C., at about 45° C., or greater, for at least up to 6 months. In some embodiments, the active agent retains at least about 8% of the original bioactivity at temperatures of about 37° C. or greater, for at least 6 months.

In some embodiments, the compositions described herein can be maintained under exposure to light, e.g., light of different wavelengths and/or from different sources. In some embodiments, the compositions described herein can be maintained under exposure to UV or infra-red irradiation. In some embodiments, the compositions described herein can be maintained under visible lights.

In some embodiments, the composition described herein when stored or transported can be subjected to at least one state-changing cycle. The term "state-changing cycle" as used herein refers to a change of a material state, including, but not limited to, from a solid state to a fluid state, or from a fluid state to a solid state. A fluid state can include, but is not limited to, liquids, gases, slurries, flowable paste, plasmas, and any combinations thereof. A solid state refers to a state that is not flowable, and it can also encompass semi-solids, e.g., a gel. The composition described herein can be maintained at a certain state for any period of time, e.g., seconds, minutes, hours, weeks, months, or years, before changing to another state. A state-changing cycle can be resulted from at least one change in an environmental condition described herein, e.g., a temperature change, a change in ambient air pressure, light condition, humidity, or any combinations thereof.

In one embodiment, the state-changing cycle refers to a freeze-thaw cycle. In such embodiments, the composition described herein when stored or transported can be subjected to at least one freeze-thaw cycle, at least two freeze-thaw cycles, at least three freeze-thaw cycles, at least four freeze-thaw cycles, at least five freeze-thaw cycles, at least six freeze-thaw cycles, at least seven freeze-thaw cycles, at least eight freeze-thaw cycles, at least nine freeze-thaw cycles, at least ten free-thaw cycles or more. The term "freeze-thaw cycles" is used herein to describe a series of alternating freezing and thawing, and also encompasses a series of alternating frozen (solid) and fluid state. For example, one freeze-thaw cycle involves a change of state between a frozen (solid) state and a fluid state. The time interval between freezing and thawing, or frozen and fluid state, can be any period of time, e.g., hours, days, weeks or months. For example, once an active agent composition has been frozen or is in a frozen state, it can be continually stored in the frozen state at sub-zero temperatures, e.g., between about −20° C. and −80° C., until it needs to be thawed for use again. Freezing of a composition can be performed rapidly, e.g., in liquid nitrogen, or gradually, e.g., in a freezing temperature, e.g., between about −20° C. and −80° C. Thawing of a frozen composition can be performed at any temperature above 0° C. rapidly, e.g., at room temperature, or gradually, e.g., on ice. Typically, an active agent in non-silk fibroin matrix can lose its bioactivity over one or more freeze-thaw cycles. As described herein, distributing an active agent in a silk fiborin matrix can increase the stability of the active agent and thus retain its bioactivity during one or more freeze-thaw cycles.

In some embodiments, the compositions described herein can be maintained at a relative humidity of at least about 5%, at least about 10%, at least about 20%, at least about 30%, at least about 40%, at least about 50% or higher. The term "relative humidity" as used herein is a measurement of the amount of water vapor in a mixture of air and water vapor. It is generally defined as the partial pressure of water vapor in the air-water mixture, given as a percentage of the saturated vapor pressure under those conditions.

In some embodiments, the compositions described herein can be lyophilized to decrease residual moisture during storage. In some embodiments, residual moisture is decreased by at least about 5%, at least about 10%, at least about 20%, at least about 30%, at least about 40%, at least about 50%, at least about 60%, at least about 70%, at least about 80%, at least about 90%, or at least about 95%.

In some embodiments, the compositions described herein can be maintained under or subjected to any air pressure. In some embodiments, the compositions described herein can be maintained under or subjected to about atmospheric pressure, or higher, e.g., about 1 atm, about 2 atms, about 3 atms, about 4 atms, about 5 atms, about 6 atms, about 7 atms, about 8 atms, about 9 atms or about 10 atms. In some embodiments, the compositions described herein can be maintained under or subjected to vacuum.

In one embodiment, the composition is maintained under two or more conditions specified herein.

Without wishing to be bound by theory, silk can reduce the degradation rate of an immunogen (e.g., vaccine) at an elevated temperature (e.g., at room temperature or above, including at least about 20° C., at least about 30° C., at least about 40° C. or higher). Thus, an immunogen (e.g., vaccine) distributed in a silk fibroin matrix can have a half-life longer at an elevated temperature (e.g., at room temperature or above, including at least about 20° C., at least about 30° C., at least about 40° C. or higher) by at least about 1.5-fold (e.g., at least about 2-fold, at least about 3-fold, at least about 4-fold, at least about 5-fold, at least about 10-fold, at least about 15-fold, at least about 20-fold, at least about 25-fold, at least about 30-fold, or more), as compared to an immunogen without the silk matrix. As used herein, the term "half-life" refers to the time at which an agent retains about 50% of its original bioactivity (including original immunogenicity or original infectivity). Accordingly, a method for extending the half-life of an immunogen (e.g., vaccine), for example, at an elevated temperature (e.g., at room temperature or above, including at least about 20° C., at least about 30° C., at least about 40° C. or higher) is also provided herein. The method comprises maintaining an immunogenic composition, wherein the composition comprises a silk fibroin matrix and at least one immunogen (e.g., vaccine) distributed therein, and wherein the immunogen (e.g., vaccine) retains at least about 30% of its original immunogenticity (e.g., infectivity) when the composition is maintained for at least about 24 hours at a temperature of at least about room temperature or higher. In some embodiments, the immunogen (e.g., vaccine) can retain at least about 80% of its original immunogenticity (e.g., infectivity). In some embodiments, the composition can be maintained for at least up to about 6 months. In some embodiments, the composition can be maintained at a temperature higher than 37° C., or higher than 45° C., or higher.

Storage-Stable Compositions

Another aspects described herein are storage-stable compositions, which comprise a silk fibroin matrix and an active agent distributed, mixed or embedded therein, wherein the active agent retains at least about 30% of its original bioactivity when the composition is subjected to at least one state-changing cycle, and/or is maintained for a period of time under one or more conditions specified herein. In one embodiment, the state-changing cycle is a freeze-thaw cycle. In one embodiment, the period of time for maintaining the active agent is at least about 24 hours. In some embodiments, the specified condition can be an environmental condition under which an active agent is stored and/or transported. Non-limiting examples of environmental conditions include temperatures, air pressures, humidity, and light exposure. In some embodiments, the compositions described herein can be immunogenic. In such embodiments, the active agent is an immunogen. In some embodiments, the active agent is a vaccine.

Any compositions described herein can be present in any material state, e.g., a film, a fiber, a particle, a gel, a microsphere, or a hydrogel. In various embodiments, the material state of the compositions described herein can vary with the state of the silk fibroin matrix, e.g., a film, a fiber, a particle, a gel, a microsphere, or a hydrogel. In some embodiments, the silk fibroin matrix is present in a solid state. In other embodiments, the silk fibroin matrix can be a solution.

Any ratio of silk fibroin to active agent may be used. In various embodiments, the ratio of a silk fibroin matrix to an active agent is about 1:1000 to about 1000:1, about 1:500 to about 500:1, about 1:250 to about 250:1, about 1:125 to about 125:1, about 1:100 to about 100:1, about 1:50 to about 50:1, about 1:25 to about 25:1, about 1:10 to about 10:1, about 1:5 to about 5:1, about 1:3 to about 3:1, or about 1:1. The ratio of the silk fibroin matrix to the active agent can vary with a number of factors, including the selection of an active agent, the storage condition and duration, the concentration of the silk fibroin matrix and the form of the silk matrix. One of skill in the art can determine appropriate ratio of the silk fibroin matrix to the active agent, e.g., by measuring the bioactivity of the active agent retained at various ratios described herein over a pre-defined amount of time under a defined condition, e.g., at a temperature of above 0° C. Methods for measuring the bioactivity of various active agents described herein, e.g., enzymes, vaccines, proteins, antibodies and nucleic acids, are well known in the art. By way of example, stability or bioactivity of a given active agent in silk fibroin may be determined based on combinations of time and temperature. For example, stabilization studies can be conducted for 6 months. Activity assays can be conducted, for example, after 2 weeks, 4 weeks, then monthly. Samples can be prepared to provide N=3 for each time point. The range of temperature storage conditions to be assessed include 4° C. (refrigeration), 25° C. (room temperature), 37° C. (body temperature), 45° C. and/or 50° C., inclusive. Additionally, activity can be assayed after one, two, three or more freeze-thaw cycles. These variables can be combined exhaustively to fully characterize the optimum formulation for long-term stability of active agent(s). In some embodiments, the results of the silk-related active agent stability can be compared with e.g., lyophilized active agent preparations with the same storage conditions, with the goal of improving the stability of the manufacture-recommended storage conditions (e.g., 4° C.) of lyophilized active agent preparations.

When the silk fibroin matrix is in solid state, it can be further processed. In some embodiments, the compositions comprising a solid-state silk fibroin matrix can be further micronized. The term "micronized" is used herein in reference to particles with an average size of about 1000 µm or less, and encompasses nanoparticles and/or microparticles. As used herein, the term "nanoparticles" is defined as particles with an average size ranging from about 1 nm to about 1000 nm, from about 5 nm to about 900 nm, or from about 10 nm to about 800 nm. The term "microparticles" refers to particles with an average size ranging from about 1 µm to 1000 µm, from about 5 µM to about 900 µm, or from about 10 µm to about 800 µm. It should be understood that "micronized" does not refer only to particles which have been produced by the finely dividing such as mechanical grinding, crushing or impinging jet, of materials which are in bulk or other form, e.g., a solid-state silk fibroin film. In some embodiments, micronized particles can also be formed by other mechanical, chemical or physical methods known in the art, such as, for example, formation in solution or in situ. A composition described herein can be micronized, e.g., by pulverizing, crushing, grinding, freeze-drying, or any combinations thereof.

Silk Fibroin

Silk fibroin is a particularly appealing biopolymer candidate to be used for embodiments of various aspects described herein, e.g., because of its all aqueous processing (Sofia et al., 54 J. Biomed. Mater. Res. 139 (2001); Perry et al., 20 Adv. Mater. 3070-72 (2008)), relatively easy functionalization (Murphy et al., 29 Biomat. 2829-38 (2008)), and biocompatibility (Santin et al., 46 J. Biomed. Mater. Res. 382-9 (1999)). For example, silk has been approved by U.S. Food and Drug Administration as a tissue engineering scaffold in human implants. See Altman et al., 24 Biomaterials: 401 (2003).

Silk can provide an immobilization matrix capable of stabilizing bioactive molecules. Previous reports on entrapment of enzymes, antibodies, and antibiotics entrapped in silk matrices indicates stabilization and recovered activity even at elevated temperatures and without specialized storage conditions or the addition of additives (Pritchard et al., "Silk fibroin encapsulated powder reservoirs for sustained release of adenosine" Journal of Controlled Release (2010) 144:159-167; Lu et al., "Stabilization of enzymes in silk films" Biomacromolecules (2009) 10:1032-1042). However, these reports do not describe that silk fibroin can stabilize vaccine (e.g., a live vaccine), which is a biological preparation and is temperature sensitive.

As used herein, the term "silk fibroin" includes silkworm fibroin and insect or spider silk protein. See e.g., Lucas et al., 13 Adv. Protein Chem. 107 (1958). Any type of silk fibroin can be used according to various aspects described herein. Silk fibroin produced by silkworms, such as *Bombyx mori*, is the most common and represents an earth-friendly, renewable resource. For instance, silk fibroin used in a silk film may be attained by extracting sericin from the cocoons of *B. mori*. Organic silkworm cocoons are also commercially available. There are many different silks, however, including spider silk (e.g., obtained from Nephila clavipes), transgenic silks, genetically engineered silks, such as silks from bacteria, yeast, mammalian cells, transgenic animals, or transgenic plants (see, e.g., WO 97/08315; U.S. Pat. No. 5,245,012), and variants thereof, that can be used.

In various embodiments, the silk fibroin matrix can be modified for different biomedical applications. For instance, to maintain the stability of an active agent distributed in a silk fibroin matrix when implanted in vivo for tissue engineering or drug delivery purposes, the silk particles can be genetically modified, which provides for further modification of the silk such as the inclusion of a fusion polypeptide comprising a fibrous protein domain and a mineralization domain, which can be used to form an organic-inorganic composite. See WO 2006/076711. Additionally, the silk matrix can be combined with one or more biocompatible polymers such as polyethylene oxide, polyethylene glycol, collagen, fibronectin, keratin, polyaspartic acid, polylysin, alginate, chitosan, chitin, hyaluronic acid, and the like. See, e.g., WO 04/062697; WO 05/012606. In some embodiments, the silk fibroin can also be chemically modified, for example through diazonium or carbodiimide coupling reactions, avidin-biodin interaction, or gene modification and the like, to alter the physical properties and functionalities of the silk protein. See, e.g., WO 2011/011347, Functionalization of Silk Material by, 4vidin-Biotin Interaction; WO 2010/057142, Surface Modification of Silk Fibroin Matrices with PEG Useful as Anti-Adhesion Barriers & Anti-Thrombotic Materials; U.S. Ser. No. 12/192,588, Diazonium Salt Modification of Silk Polymer. Additionally, the silk fibroin matrix can be combined with a chemical, such as glycerol, that, e.g., affects flexibility of the matrix. See, e.g., WO 2010/042798, Modified Silk films Containing Glycerol.

Active Agents

As used herein, the term "active agent" refers to any molecule, compound or composition, bioactivity of which is desired to be stabilized when such molecule, compound, or composition is subjected to at least one state-changing cycle, and/or is maintained under certain conditions as described herein. For the methods and compositions described herein, any active agent can be maintained within a silk-fibroin matrix. Examples of active agents include, but are not limited to, proteins, peptides, antigens, immunogens, vaccines, antibodies or portions thereof (e.g., antibody-like molecules), enzymes, nucleic acids (e.g., oligonucleotides, polynucleotides, siRNA, shRNA), aptamers, viruses, bacteria, small molecules, cells, photosynthetic and energy-harvesting compounds, flavors, antibiotics, therapeutic agents, diagnostic agents such as contrast agents or dye, viral vectors, and anti-venom.

As used herein, the terms "proteins" and "peptides" are used interchangeably herein to designate a series of amino acid residues connected to the other by peptide bonds between the alpha-amino and carboxy groups of adjacent residues. The terms "protein", and "peptide", which are used interchangeably herein, refer to a polymer of protein amino acids, including modified amino acids (e.g., phosphorylated, glycated, etc.) and amino acid analogs, regardless of its size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein" and "peptide" are used interchangeably herein when referring to a gene product and fragments thereof. Thus, exemplary peptides or proteins include gene products, naturally occurring proteins, homologs, orthologs, paralogs, fragments and other equivalents, variants, fragments, and analogs of the foregoing.

The term "nucleic acids" used herein refers to polynucleotides such as deoxyribonucleic acid (DNA), and, where appropriate, ribonucleic acid (RNA), polymers thereof in either single- or double-stranded form. Unless specifically limited, the term encompasses nucleic acids containing known analogs of natural nucleotides, which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer, et al., Nucleic Acid Res. 19:5081 (1991); Ohtsuka, et al., J. Biol. Chem. 260:2605-2608 (1985), and Rossolini, et al., Mol. Cell. Probes 8:91-98 (1994)). The term "nucleic acid" should also be understood to include, as equivalents, derivatives, variants and analogs of either RNA or DNA made from nucleotide analogs, and, single (sense or antisense) and double-stranded polynucleotides.

The term "short interfering RNA" (siRNA), also referred to herein as "small interfering RNA" is defined as an agent which functions to inhibit expression of a target gene, e.g., by RNAi. An siRNA can be chemically synthesized, it can be produced by in vitro transcription, or it can be produced within a host cell. siRNA molecules can also be generated by cleavage of double stranded RNA, where one strand is identical to the message to be inactivated. The term "siRNA" refers to small inhibitory RNA duplexes that induce the RNA interference (RNAi) pathway. These molecules can vary in length (generally 18-30 base pairs) and contain varying degrees of complementarity to their target mRNA in the antisense strand. Some, but not all, siRNA have unpaired overhanging bases on the 5' or 3' end of the sense 60 strand and/or the antisense strand. The term "siRNA" includes duplexes of two separate strands, as well as single strands that can form hairpin structures comprising a duplex region.

The term "shRNA" as used herein refers to short hairpin RNA which functions as RNAi and/or siRNA species but differs in that shRNA species are double stranded hairpin-like structure for increased stability. The term "RNAi" as used herein refers to interfering RNA, or RNA interference molecules are nucleic acid molecules or analogues thereof for example RNA-based molecules that inhibit gene expression. RNAi refers to a means of selective post-transcriptional gene silencing. RNAi can result in the destruction of specific mRNA, or prevents the processing or translation of RNA, such as mRNA.

The term "enzymes" as used here refers to a protein molecule that catalyzes chemical reactions of other substances without it being destroyed or substantially altered upon completion of the reactions. The term can include naturally occurring enzymes and bioengineered enzymes or mixtures thereof. Examples of enzyme families include kinases, dehydrogenases, oxidoreductases, GTPases, carboxyl transferases, acyl transferases, decarboxylases, transaminases, racemases, methyl transferases, formyl transferases, and a-ketodecarboxylases.

The term "vaccines" as used herein refers to any preparation of killed microorganisms, live attenuated organisms, subunit antigens, toxoid antigens, conjugate antigens or other type of antigenic molecule that when introduced into a subjects body produces immunity to a specific disease by causing the activation of the immune system, antibody formation, and/or creating of a T-cell and/or B-cell response. Generally vaccines against microorganisms are directed toward at least part of a virus, bacteria, parasite, *mycoplasma*, or other infectious agent. In one embodiment, vaccine encapsulated in a silk fibroin matrix is a live vaccine.

As used herein, the term "aptamers" means a single-stranded, partially single-stranded, partially double-stranded or double-stranded nucleotide sequence capable of specifically recognizing a selected non-oligonucleotide molecule or group of molecules. In some embodiments, the aptamer recognizes the non-oligonucleotide molecule or group of molecules by a mechanism other than Watson-Crick base pairing or triplex formation. Aptamers can include, without limitation, defined sequence segments and sequences comprising nucleotides, ribonucleotides, deoxyribonucleotides, nucleotide analogs, modified nucleotides and nucleotides comprising backbone modifications, branchpoints and non-nucleotide residues, groups or bridges. Methods for selecting aptamers for binding to a molecule are widely known in the art and easily accessible to one of ordinary skill in the art.

As used herein, the term "antibody" or "antibodies" refers to an intact immunoglobulin or to a monoclonal or polyclonal antigen-binding fragment with the Fc (crystallizable fragment) region or FcRn binding fragment of the Fc region. The term "antibodies" also includes "antibody-like molecules", such as fragments of the antibodies, e.g., antigen-binding fragments. Antigen-binding fragments can be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies, and polypeptides that contain at least a portion of an immunoglobulin that is sufficient to confer specific antigen binding to the polypeptide. Linear antibodies are also included for the purposes described herein. The terms Fab, Fc, pFc', F(ab') 2 and Fv are employed with standard immunological meanings (Klein, Immunology (John Wiley, New York, N.Y., 1982); Clark, W. R. (1986) The Experimental Foundations of Modern Immunology (Wiley & Sons, Inc., New York); and Roitt, I. (1991) Essential Immunology, 7th Ed., (Blackwell Scientific Publications, Oxford)). Antibodies or antigen-binding fragments specific for various antigens are available commercially from vendors such as R&D Systems, BD Biosciences, e-Biosciences and Miltenyi, or can be raised against these cell-surface markers by methods known to those skilled in the art.

As used herein, the term "Complementarity Determining Regions" (CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). In some instances, a complementarity determining region can include amino acids from both a CDR region defined according to Kabat and a hypervariable loop.

The expression "linear antibodies" refers to the antibodies described in Zapata et al., Protein Eng., 8(10):1057-1062 (1995). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

The expression "single-chain Fv" or "scFv" antibody fragments, as used herein, is intended to mean antibody fragments that comprise the VH and VL domains of antibody, wherein these domains are present in a single polypeptide chain. Preferably, the Fv polypeptide further comprises a polypeptide linker between the VH and VL domains which enables the scFv to form the desired structure for antigen binding. (Pluckthun, The Pharmacology of Monoclonal Antibodies, vol. 113, Rosenburg and Moore eds., Springer-Verlag, New York, pp. 269-315 (1994)).

The term "diabodies," as used herein, refers to small antibody fragments with two antigen-binding sites, which fragments comprise a heavy-chain variable domain (VH) Connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. (EP 404,097; WO 93/11161; Hollinger et ah, Proc. Natl. Acad. Sd. USA, P0:6444-6448 (1993)).

As used herein, the term "small molecules" refers to natural or synthetic molecules including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The term "bacteria" as used herein is intended to encompass all variants of bacteria, for example, prokaryotic organisms and cyanobacteria. Bacteria are small (typical linear dimensions of around 1 m), non-compartmentalized, with circular DNA and ribosomes of 70S.

The term "antibiotics" is used herein to describe a compound or composition which decreases the viability of a microorganism, or which inhibits the growth or reproduction of a microorganism. As used in this disclosure, an antibiotic is further intended to include an antimicrobial, bacteriostatic, or bactericidal agent. Exemplary antibiotics include, but are not limited to, penicillins, cephalosporins, penems, carbapenems, monobactams, aminoglycosides, sulfonamides, macrolides, tetracyclins, lincosides, quinolones, chloramphenicol, vancomycin, metronidazole, rifampin, isoniazid, spectinomycin, trimethoprim, sulfamethoxazole, and the like.

The term "cells" used herein refers to any cell, prokaryotic or eukaryotic, including plant, yeast, worm, insect and mammalian. Mammalian cells include, without limitation; primate, human and a cell from any animal of interest, including without limitation; mouse, hamster, rabbit, dog, cat, domestic animals, such as equine, bovine, murine, ovine, canine, feline, etc. The cells may be a wide variety of tissue types without limitation such as; hematopoietic, neural, mesenchymal, cutaneous, mucosal, stromal, muscle spleen, reticuloendothelial, epithelial, endothelial, hepatic, kidney, gastrointestinal, pulmonary, T-cells etc. Stem cells, embryonic stem (ES) cells, ES-derived cells and stem cell progenitors are also included, including without limitation, hematopoeitic, neural, stromal, muscle, cardiovascular, hepatic, pulmonary, gastrointestinal stem cells, etc. Yeast cells can also be used as cells in some embodiments. In some embodiments, the cells can be ex vivo or cultured cells, e.g. in vitro. For example, for ex vivo cells, cells can be obtained from a subject, where the subject is healthy and/or affected with a disease. Cells can be obtained, as a non-limiting example, by biopsy or other surgical means know to those skilled in the art.

The term "photosynthetic and energy-harvesting compounds" refers to molecules that can obtain or absorb energy from light, e.g., chlorophyll.

As used herein, the term "viral vector" typically includes foreign DNA which is desired to be inserted in a host cell and usually includes an expression cassette. The foreign DNA can comprise an entire transcription unit, promoter gene-poly A or the vector can be engineered to contain promoter/transcription termination sequences such that only the gene of interest need be inserted. These types of control sequences are known in the art and include promoters for transcription initiation, optionally with an operator along with ribosome binding site sequences. Viral vectors include, but are not limited to, lentivirus vectors, retroviral vectors, lentiviral vectors, herpes simplex viral vectors, adenoviral vectors, adeno-associated viral (AAV) vectors, EPV, EBV or variants or derivatives thereof. Various companies produce such viral vectors commercially, including, but not limited to, Avigen, Inc. (Alameda, Calif.; AAV vectors), Cell Genesys (Foster City, Calif.; retroviral, adenoviral, AAV, and lentiviral vectors), Clontech (retroviral and baculoviral vectors), Genovo, Inc. (Sharon Hill, Pa.; adenoviral and AAV vectors), Genvec (France; adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

As used herein, the term "antigens" refers to a molecule or a portion of a molecule capable of being bound by a selective binding agent, such as an antibody, and additionally capable of being used in an animal to elicit the production of antibodies capable of binding to an epitope of that antigen. An antigen may have one or more epitopes. The term "antigen" can also refer to a molecule capable of being bound by an antibody or a T cell receptor (TCR) if presented by MHC molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

As used herein, the term "viruses" refers to an infectious agent composed of a nucleic acid encapsidated in a protein. Such infectious agents are incapable of autonomous replication (i.e., replication requires the use of the host cell's machinery). Viral genomes can be single-stranded (ss) or double-stranded (ds), RNA or DNA, and can or cannot use reverse transcriptase (RT). Additionally, ssRNA viruses can be either sense (+) or antisense (−). Exemplary viruses include, but are not limited to, dsDNA viruses (e.g. Adenoviruses, Herpesviruses, Poxviruses), ssDNA viruses (e.g. Parvoviruses), dsRNA viruses (e.g. Reoviruses), (+)ssRNA viruses (e.g. Picornaviruses, Togaviruses), (−)ssRNA viruses (e.g. Orthomyxoviruses, Rhabdoviruses), ssRNA-RT viruses, i.e., (+)sense RNA with DNA intermediate in lifecycle (e.g. Retroviruses), and dsDNA-RT viruses (e.g. Hepadnaviruses). In some embodiments, viruses can also include wild-type (natural) viruses, killed viruses, live attenuated viruses, modified viruses, recombinant viruses or any combinations thereof. Other examples of viruses include, but are not limited to, enveloped viruses, respiratory syncytial viruses, non-enveloped viruses, bacteriophages, recombinant viruses, and viral vectors. The term "bacteriophages" as used herein refers to viruses that infect bacteria.

The term "anti-venom," as used herein, refers to a biological product used in the treatment of venomous bites or stings. The anti-venom is created by milking venom from the desired snake, spider or insect. The venom is then diluted and injected into a horse, sheep, goat or cat. The subject animal will undergo an immune response to the venom, producing antibodies against the venom's active molecule which can then be harvested from the animal's blood and used to treat envenomation.

The term "therapeutic agents" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians' Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from the subject composition into adjacent tissues or fluids upon administration to a subject. Examples include steroids and esters of steroids (e.g., estrogen, progesterone, testosterone, androsterone, cholesterol, norethindrone, digoxigenin, cholic acid, deoxycholic acid, and chenodeoxycholic acid), boron-containing compounds (e.g., carborane), chemotherapeutic nucleotides, drugs (e.g., antibiotics, antivirals, antifungals), enediynes (e.g., calicheamicins, esperamicins, dynemicin, neocarzinostatin chromophore, and kedarcidin chromophore), heavy metal complexes (e.g., cisplatin), hormone antagonists (e.g., tamoxifen), non-specific (non-antibody) proteins (e.g., sugar oligomers), oligonucleotides (e.g., antisense oligonucleotides that bind to a target nucleic acid sequence (e.g., mRNA sequence)), peptides, proteins, antibodies, photodynamic agents (e.g., rhodamine 123), radionuclides (e.g., I-131, Re-186, Re-188, Y-90, Bi-212, At-211, Sr-89, Ho-166, Sm-153, Cu-67 and Cu-64), toxins (e.g., ricin), and transcription-based pharmaceuticals.

A "diagnostic agent" is any chemical moiety that can be used for diagnosis. For example, diagnostic agents include imaging agents containing radioisotopes such as indium or technetium; contrast agents or dyes containing iodine, gadolinium or cyanine; enzymes such as horse radish peroxidase, GFP, alkaline phosphatase, or β-galactosidase; fluorescent substances such as europium derivatives; luminescent substances such as N-methylacrydium derivatives or the like.

Immunogen and Vaccines

In certain embodiments, the active agents are immunogens. In some embodiments, the immunogen is a vaccine. As shown herein, a model vaccine MMR live attenuated vaccine entrapped and subsequently recovered from a silk earlier maintained significant biological activity compared to non-silk-entrapped vaccine. In one embodiment, provided herein is a stabilized MMR vaccine that can be stored at ambient temperature for several weeks while maintaining a substantial proportion of original activity. The stabilization of live attenuated vaccines provides an important breakthrough in immunization programs, lowering costs for transportation, equipment and training; reducing wastage; and thus expanding immunization programs.

The term "immunogen" refers to any substance, e.g., vaccines, capable of eliciting an immune response in an organism. An "immunogen" is capable of inducing an immunological response against itself on administration to a subject. The term "immunological" as used herein with respect to an immunological response, refers to the development of a humoral (antibody mediated) and/or a cellular (mediated by antigen-specific T cells or their secretion products) response directed against an immunogen in a recipient subject. Such a response can be an active response induced by administration of an immunogen or immunogenic peptide to a subject or a passive response induced by administration of antibody or primed T-cells that are directed towards the immunogen. A cellular immune response is elicited by the presentation of polypeptide epitopes in association with Class I or Class II MHC molecules to activate antigen-specific CD4+ T helper cells and/or CDS+ cytotoxic T cells. Such a response can also involve activation of monocytes, macrophages, NK cells, basophils, dendritic cells, astrocytes, microglia cells, eosinophils or other components of innate immunity.

The term "immunogenicity" refers to the ability of a substance, such as an antigen or epitope, to provoke humoral and/or cell-mediated immunological response in a subject. A skilled artisan can readily measure immunogenicity of a substance. The presence of a cell-mediated immunological response can be determined by any art-recognized methods, e.g., proliferation assays (CD4+ T cells), CTL (cytotoxic T lymphocyte) assays (see Burke, supra; Tigges, supra), or immunohistochemistry with tissue section of a subject to determine the presence of activated cells such as monocytes and macrophages after the administration of an immunogen. One of skill in the art can readily determine the presence of humoral-mediated immunological response in a subject by any well-established methods. For example, the level of antibodies produced in a biological sample such as blood can be measured by western blot, ELISA or other methods known for antibody detection.

Immunogens useful in some embodiments of various aspects described herein include killed pathogens, live attenuated pathogens, protein subunits and conjugates thereof, inactivated toxins, and synthetic peptides, carbohydrates and conjugates thereof, and antigens. The term "pathogen" as used herein means any disease-producing agent (especially a virus or bacterium or other microorganism).

The term "killed pathogens" is used herein in reference to pathogen that were previously virulent (i.e. able to cause disease) but have been destroyed with chemicals or heat. Examples of vaccines comprising killed pathogens include, without limitations, the influenza vaccine, cholera vaccine, bubonic plague vaccine, polio vaccine, hepatitis A vaccine, and rabies vaccine.

The term "live attenuated pathogens" as used herein refers to pathogens that have not been inactivated, i.e. pathogens capable of replicating on permissive cells and inducing a specific immunological response, but do not induce diseases caused by the corresponding wild-type pathogens in a subject. Live attenuated pathogens can be produced by one of skill in the art, e.g., by cultivating wild-type pathogens under conditions that disable their virulent properties, or using closely-related but less virulent organisms to produce such an immunological response. Exemplary live attenuated pathogens include, but are not limited to, the viral diseases yellow fever, measles, rubella, and mumps and the bacterial disease typhoid. In some embodiments, the live *Mycobacterium tuberculosis* vaccine is not made of a contagious strain, but contains a virulently modified strain called "BCG" used to elicit an immune response to the vaccine. The live attenuated vaccine containing strain *Yersinia pestis* EV is used for plague immunization.

In some embodiments, an immunogen used in the compositions described herein can be inactivated toxins that cause diseases rather than the pathogen. Such non-limiting compositions include tetanus and diphtheria. In some embodiments, while an immunogen can comprise an inactivated compound, e.g., an inactivated toxin, from a pathogen, synthetic peptides, carbohydrates, or antigens can also be used as an immunogen in the immunogenic compositions described herein.

In certain embodiments, an immunogen used in the compositions described herein can include a protein subunit, i.e., a fragment of a killed or live attenuated pathogen, or a conjugate thereof. Such exemplary examples include, without limitations, the subunit vaccine against Hepatitis B virus that is composed of only the surface proteins of the virus (previously extracted from the blood serum of chronically infected patients, but now produced by recombination of the viral genes into yeast), the virus-like particle (VLP) vaccine against human papillomavirus (HPV) that is composed of the viral major capsid protein, and the hemagglutinin and neuraminidase subunits of the influenza virus. In such embodiments, certain pathogens have polysaccharide outer coats that are poorly immunogenic. By linking these outer coats to proteins (e.g. toxins), the immune system can recognize the polysaccharide as if it were a protein antigen. An exemplary conjugated immunogen is the one used in *Haemophilus influenzae* type B vaccine. Accordingly, conjugated immunogens are also included in the aspects described herein.

Additional examples of immunogens includes the ones that can be derived from hepatitis B virus, *Haemophilus influenzae* Type B, poliovirus, *Neisseria meningitides* C, influenza, *Varicella*, or *Mycobacteria tuberculosis* bacille Calmette-Guérin, tetanus toxoid, diphtheria toxoid, or *Bordetella pertussis*. The immunogen can also be a combination immunogen, such as DTaP, DTwP, DTwP hepB, DTP hep B Hib, or DTaP hep B Hib IPV.

In some embodiments, the immunogen is a bacterium, such as *Mycobacteria tuberculosis* bacille Calmette-Guérin or *Bordetella pertussis*. The bacterial immunogen can be killed or attenuated. The immunogen can comprise a bacterial subunit. Example immunogenic bacterial subunits include those derived from *Neisseria meningitides* type C, *Haemophilus influenzae* type B, *Streptococcus pneumoniae*, Group B *streptococcus*, or *Bordetella pertussis*. The bacterial immunogen can be recombinant. The bacterial subunit can be, or include, a polysaccharide. In still other embodiments, the immunogen is a viral subunit, for example, derived from Hepatitis B virus or Human Papillomavirus. The viral immunogen can also be recombinant. The viral immunogen can also comprise killed virus.

The immunogen stabilized as described herein can be a vaccine product, for example, BIOTHRAX® (anthrax vaccine adsorbed, Emergent Biosolutions, Rockville, MD); TICE® BCG Live (*Bacillus* Calmette-Guerin for intravesical use, Organon Tekina Corp. LLC, Durham, NC); MYCOBAX BCG Live (Sanofi Pasteur Inc); DAPTACEL® (diphtheria and tetanus toxoids and acellular pertussis [DTaP] vaccine adsorbed, Sanofi Pasteur Inc.); INFANRIX® (DTaP vaccine adsorbed, GlaxoSmithKline); TRIPEDIA® (DTaP vaccine, Sanofi Pasteur); TRIHIBIT® (DTaP/Hib#, sanofi pasteur); KINRIX® (diphtheria and tetanus toxoids, acellular pertussis adsorbed and inactivated poliovirus vaccine, GlaxoSmithKline); PEDIARIX® (DTaP-HepB-IPV, GlaxoSmithKline); PENTACEL® (diphtheria and tetanus toxoids and acellular pertussis adsorbed, inactivated poliovirus and *Haemophilus* b conjugate [tetanus toxoid conjugate] vaccine, sanofi pasteur); Diphtheria and Tetanus Toxoids, adsorbed (for pediatric use, Sanofi Pasteur); DECAVAC® (diphtheria and tetanus toxoids adsorbed, for adult use, Sanofi Pasteur); ACTHIB® (*Haemophilus* b tetanus toxoid conjugate vaccine, Sanofi Pasteur); PEDVAXHIB® (Hib vaccine, Merck); Hiberix (*Haemophilus* b tetanus toxoid conjugate vaccine, booster dose, GlaxoSmithKline); COMVAX® (Hepatitis B-Hib vaccine, Merck); HAVRIX® (Hepatitis A vaccine, pediatric, GlaxoSmithKline); VAQTA® (Hepatitis A vaccine, pediatric, Merck); ENGERIX-B® (Hep B, pediatric, adolescent, GlaxoSmithKline); RECOMBIVAX HB® (hepatitis B vaccine, Merck); TWINRIX® (HepA/HepB vaccine, 18 years and up, GlaxoSmithKline); CERVARIX® (human papillomavirus bivalent [types 16 and 18] vaccine, recombinant, GlaxoSmithKline); GARDASIL® (human papillomavirus bivalent [types 6, 11, 16 and 18] vaccine, recombinant, Merck); AFLURIA® (Influenza vaccine, 18 years and up, CSL); AGRIFLU™ (influenza virus vaccine for intramuscular injection, Novartis Vaccines); FLUARIX® (Influenza vaccine, 18 years and up, GaxoSmithKline); FLULAVAL® (Influenza vaccine, 18 years and up, GaxoSmithKline); FLUVIRIN® (Influenza vaccine, 4 years and up, Novartis Vaccine); FLUZONE® (Influenza vaccine, 6 months and up, Sanofi Pasteur); FLUMIST® (Influenza vaccine, 2 years and up, Medimmune); IPOL® (e-IPV polio vaccine, sanofi Pasteur); JE-VAX® (Japanese encephalitis virus vaccine inactivated, EIKEN, Japan); IXIARO® (Japanese encephalitis virus vaccine inactivated, Novarits); MENACTRA® (Meningococcal [Groups A, C, Y and W-135] and diphtheria vaccine, Sanofi Pasteur); MENOMUNE®-A/C/Y/W-135 (Meningococcal polysaccharide vaccine, sanofi pasteur); MMRII® (MMR vaccine, Merck); MENVEO® (Meningococcal [Groups A, C, Y and W-135] oligosaccharide diphtheria $CRM_{197}$ conjugate vaccine, Novartis Vaccines); PROQUAD® (MMR and varicella vaccine, Merck); PNEUMOVAX 23® (pneumococcal polysaccharide vaccine, Merck); PREVNAR® (pneumococcal vaccine, 7-valent, Wyeth/Lederle); PREVNAR-130 (pneumococcal vaccine, 13-valent, Wyeth/Lederle); POLIOVAX™ (poliovirus inactivated, sanofi pasteur); IMOVAX® (Rabies vaccine, Sanofi Pasteur); RABAVERT™ (Rabies vaccine, Chiron); ROTATEQ® (Rotavirus vaccine, live, oral pentavalent, Merck); ROTARIX® (Rotavirus, live, oral vaccine, GlaxoSmithKline); DECAVAC™ (tetanus and diphtheria toxoids vaccine, sanofi pasteur); Td (generic) (tetanus and diphtheria toxoids, adsorbed, Massachusetts Biol. Labs); TYPHIMVI® (typhoid Vi polysaccharide vaccine, Sanofi Pasteur); ADACEL® (tetanus toxoid, reduced diphtheria toxoid and acellular pertussis, sanofi pasteur); BOOSTRIX® (tetanus toxoid, reduced diphtheria toxoid and acellular pertussis, GlaxoSmithKline); VIVOTIF® (typhoid vaccine live oral Ty21a, Berna Biotech); ACAM2000™ (Smallpox (vaccinia) vaccine, live, Acambis, Inc.); DRYVAX® (Smallpox (vaccinia) vaccine); VARIVAX® (varicella [live] vaccine, Merck); YF-VAX® (Yellow fever vaccine, Sanofi Pasteur); ZOSTAVAX® (*Varicella* zoster, Merck); or combinations thereof. Any vaccine products listed in database of Center for Disease Control and Prevention (CDC) can also be included in the compositions described herein.

In some embodiments, animal vaccines such as canine and feline vaccines can also be included in the methods and compositions described herein. Examples of animal vaccines include, but are not limited to, DURAN/TUNE® MAX 5 (5-way vaccine: Canine Distemper, Infectious Canine Hepatitis, Adenovirus Type 2, Parainfluenza, and Parvovirus, Fort Dodge); NEO PAR® (parvovirus, Neo Tech); VANGUARD® PLUS 5 (Canine Distemper, Adenovirus Type 1 and 2, Parainfluenza and Parvovirus; Pfizer); BRONCHI-SHIELD® III (Canine Parainfluenza; Fort Dodge); and ECLIPSE® 4 (feline rhinotracheitis, calici, and panleukopenia viruses and *Chlamydia psittaci*, Schering-Plough/Intervet). Any commercially available animal vaccines can be included in the compositions described herein.

Live Attenuated Virus

Live attenuated immunogenic compositions, e.g., live attenuated vaccines, can generally provoke more durable immunological responses. Thus, they are sometimes the preferred compositions for administration to a subject, e.g., a healthy mammalian. In some embodiments, the immunogens used in the compositions described herein is live, attenuated pathogens. In particular embodiments, the immunogens are live attenuated viruses. Accordingly, methods and immunogenic compositions comprising at least one live attenuated virus (including at least two live attenuated viruses, at least three live attenuated viruses, or more) are also described herein. The immunogenic compositions include a silk-fibroin matrix and at least one live attenuated virus (including at least two live attenuated viruses, at least three live attenuated viruses, or more) distributed therein, wherein the live attenuated virus(es) retains at least about 30% of its original infectivity when the composition is (a) subjected to at least one state-changing cycle, and/or (b) maintained for a period of time under a specified condition. In some embodiments, the live attenuated virus(es) can retain at least about 30%, at least about 40%, at least about 50%, at least about 60%, at least about 70%, at least about 80%, at least about 90%, at least about 95% of original infectivity or higher.

As used herein, the term "infectivity" in reference to a virus means the characteristic of a virus that embodies capability of entering, surviving in, and multiplying or causing an immunological response in a susceptible host. Any methods known to a skilled artisan for determination of virus infectivity can be used for the purposes described herein, e.g., the in vitro infectivity assay described in Example 1 can be employed.

In particular embodiments, the live attenuated virus can be an enveloped virus such as Paramyxoviridae, Togaviridae, Orthomyxoviridae, Flaviviridae, Herpesviridae, Rhabdovirus, or Retroviridae. These enveloped, live, attenuated virus can be varicella, measles virus, mumps virus, German measles virus, respiratory syncytial virus, yellow fever virus, or influenza virus. By "enveloped virus" is meant a virus comprising a lipid-containing or lipoprotein-containing membrane which surrounds their protein capsids. These viral envelopes can be derived from portions of the host cell membranes (phospholipids and proteins), but include some viral glycoproteins. Functionally, viral envelopes can be used to help viruses enter host cells. For example, glycoproteins on the surface of the envelope serve to identify and bind to receptor sites on the host's membrane. The viral envelope then fuses with the host's membrane, allowing the capsid and viral genome to enter and infect the host. However, as the viral envelope is relatively sensitive to desiccation, heat and detergents, these enveloped viruses can be sterilized more easily than non-enveloped viruses, and thus have limited survival outside host environments. Accordingly, methods and immunogenic compositions provided herein are of particular importance to maintain the survival of live attenuated enveloped virus outside host environments and thus their infectivity once introduced into a host cell.

In other embodiments, the live, attenuated virus can be a non-enveloped virus, i.e. a virus with no viral envelop as described above. The non-enveloped virus can be rotavirus, reovirus, hepatitis virus, rabies virus and/or poliovirus.

Further provided herein is a cell-free, stabilized virus preparation comprising a silk fibroin matrix and infective virus distributed, mixed or embedded therein, wherein the virus retains at least about 30% of its original infectivity when the preparation is (a) subjected to at least one state-changing cycle, and/or (b) is maintained for a period of time under a condition specified herein.

Additives and Pharmaceutically-Acceptable Carriers

Various embodiments of the compositions described herein can further comprise an additive distributed, mixed or embedded in the silk fibroin matrix. In some embodiments, the additive is a stabilizing agent. The addition of "stabilizing agent" to the compositions described herein can further increase the stability of the active agent, i.e., the active agent can retain a higher bioactivity, relative to the bioactivity in the absence of the stabilizing agent. In some embodiments, the stabilizing agent is selected from the group consisting of a saccharide, a sugar alcohol, an ion, a surfactant, and any combinations thereof. In one embodiment, the saccacharide, e.g., sucrose, is added into the compositions described herein.

By way of example, additional stabilizing agents can be added to the silk fibroin solution or matrix. Example stabilizers previously shown to be effective on oral polio vaccine as well as those discussed herein can be used. Stabilizing agents may include cationic stabilizers (listed most to least stabilizing): $(CH_3)_4N^+ > Mg^{2+}$, $K^+ > Na^+$, $NH_4^+ > Li^+$, anionic stabilizers (most to least stabilizing): $CH_3COO^-$, $SO_4^{2-}$, $PO_4^{2-} > Cl^-$, $SCN^-$; and heavy water ($D_2O$) (Dorval et al, 1989). See, e.g., Mirchamsy et al., *Stabilizing effect of magnesium chloride and sucrose on Sabin live polio vaccine*, 41 Devel. Biol. Standardization 255 (1978); Rapp et al., *Protection of measles virus by sulfate ions against thermal inactivation*, 90 J. Bact. 132 (1965). Other stabilizing agents known in the art, e.g., for stabilizing other vaccines, can also be included in the compositions described herein, for example, amino acids, such as sodium glutamate, arginine, lysine, and cysteine; monosaccharides, such as glucose, galactose, fructose, and mannose; disaccharides, such as sucrose, maltose, and lactose; sugar alcohols such as sorbitol and mannitol; polysaccharides, such as oligosaccharide, starch, cellulose, and derivatives thereof; human serum albumin and bovine serum albumin; gelatin, and gelatin derivatives, such as hydrolyzed gelatin; and ascorbic acid as an antioxidant. These materials are described in publications, e.g., "Toketsu-Kanso To Hogo Busshitsu (Lyophilization And Protective Materials)" written by Nei, p. 1-176, published by Tokyo Daigaku Shuppan Kai (Publishing Association of the University of Tokyo), Japan in 1972; and "Shinku Gijutsu Koza (8): Sinku Kanso (Lecture on Vacuum Technology (8): Vacuum Drying)" written by Ota et al., p. 176-182, published by Nikkan Kogyo Shimbun Co., Ltd., Japan in 1964.

In some embodiments, the compositions or preparations described herein can further comprise a pharmaceutically acceptable carrier. Depending on the selected administration route, the compositions or preparations can be in any form, e.g., a tablet, a lozenge, a suspension, a free-flowing powder, an aerosol, and a capsule. The term "pharmaceutically acceptable," as used herein, refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable carrier" refers to a pharmaceutically-acceptable material, composition or vehicle for administration of an active agent described herein. Pharmaceutically acceptable carriers include any and all solvents, dispersion media, coatings, antibacterial and antifungal agents, isotonic and absorption delaying agents, and the like which are compatible with the activity of the active agent and are physiologically acceptable to the subject. Some examples of materials which can serve as pharmaceutically-acceptable carriers include: (i) sugars, such as lactose, glucose and sucrose; (ii) starches, such as corn starch and potato starch; (iii) cellulose, and its derivatives, such as sodium carboxymethyl cellulose, methylcellulose, ethyl cellulose, microcrystalline cellulose and cellulose acetate; (iv) powdered tragacanth; (v) malt; (vi) gelatin; (vii) lubricating agents, such as magnesium stearate, sodium lauryl sulfate and talc; (viii) excipients, such as cocoa butter and suppository waxes; (ix) oils, such as peanut oil, cottonseed oil, safflower oil, sesame oil, olive oil, corn oil and soybean oil; (x) glycols, such as propylene glycol; (xi) polyols, such as glycerin, sorbitol, mannitol and polyethylene glycol (PEG); (xii) esters, such as ethyl oleate and ethyl laurate; (xiii) agar; (xiv) buffering agents, such as magnesium hydroxide and aluminum hydroxide; (xv) alginic acid; (xvi) pyrogen-free water; (xvii) isotonic saline; (xviii) Ringer's solution; (xix) ethyl alcohol; (xx) pH buffered solutions; (xxi) polyesters, polycarbonates and/or polyanhydrides; (xxii) bulking agents, such as polypeptides and amino acids (xxiii) serum component, such as serum albumin, HDL and LDL; (xxiv) C2-C12 alcohols, such as ethanol; and (xxv) other non-toxic compatible substances employed in pharmaceutical formulations. Wetting agents, coloring agents, release agents, coating agents, sweetening agents, flavoring agents, perfuming agents, preservative and antioxidants can also be present in the formulation. For compositions or preparations described herein to be administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Pharmaceutically acceptable carriers can vary in a preparation described herein, depending on the administration route and formulation. The compositions and preparations described herein can be delivered via any administration mode known to a skilled practitioner. For example, the compositions and preparations described herein can be delivered in a systemic manner, via administration routes such as, but not limited to, oral, and parenteral including intravenous, intramuscular, intrapelitoneal, intradermal, and subcutaneous. In some embodiments, the compositions and preparations described herein are in a form that is suitable for injection. In other embodiments, the compositions and preparations described herein are formulated for oral administration.

When administering parenterally, a composition and preparation described herein can be generally formulated in a unit dosage injectable form (solution, suspension, emulsion). The compositions and preparations suitable for injection include sterile aqueous solutions or dispersions. The carrier can be a solvent or dispersing medium containing, for example, water, cell culture medium, buffers (e.g., phosphate buffered saline), polyol (for example, glycerol, propylene glycol, liquid polyethylene glycol, and the like), suitable mixtures thereof. In some embodiments, the pharmaceutical carrier can be a buffered solution (e.g. PBS).

An oral composition can be prepared in any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. Liquid preparations for oral administration can also be prepared in the form of a dry powder to be reconstituted with a suitable solvent prior to use.

The compositions can also contain auxiliary substances such as wetting or emulsifying agents, pH buffering agents, gelling or viscosity enhancing additives, preservatives, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation. With respect to compositions described herein, however, any vehicle, diluent, or additive used should have to be biocompatible with the active agents described herein. Those skilled in the art will recognize that the components of the compositions should be selected to be biocompatible with respect to the active agent. This will present no problem to those skilled in chemical and pharmaceutical principles, or problems can be readily avoided by reference to standard texts or by simple experiments (not involving undue experimentation).

In some embodiments, the compositions and preparations described herein can be formulated in an emulsion or a gel. Such gel compositions and preparations can be implanted locally to a diseased tissue region of a subject.

For in vivo administration, the compositions or preparations described herein can be administered with a delivery device, e.g., a syringe. Accordingly, an additional aspect described herein provides for delivery devices comprising at least one chamber with an outlet, wherein the at least one chamber comprises a pre-determined amount of any composition described herein and the outlet provides an exit for the composition enclosed inside the chamber. In some embodiments, a delivery device described herein can further comprise an actuator to control release of the composition through the outlet. Such delivery device can be any device to facilitate the administration of any composition described herein to a subject, e.g., a syringe, a dry powder injector, a nasal spray, a nebulizer, or an implant such as a microchip, e.g., for sustained-release or controlled release of any composition described herein.

In some embodiments of the compositions described herein, the silk fibroin matrix itself can be modified to control its degradation and thus the release of active agents, e.g. such that release occurs over a period of time ranging from hours to days, or months. In some embodiments, the compositions described herein can be combined with other types of delivery systems available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations thereof. Microcapsules of the foregoing polymers containing drugs are described in, for example, U.S. Pat. No. 5,075,109. Other examples include nonpolymer systems that are lipid-based including sterols such as cholesterol, cholesterol esters, and fatty acids or neukal fats such as mono-, di- and triglycerides; hydrogel release systems; liposome-based systems; phospholipid based-systems; silastic systems; peptide based systems; or partially fused implants. Specific examples include, but are not limited to, erosional systems in which the composition is contained in a form within a matrix (for example, as described in U.S. Pat. Nos. 4,452,775, 4,675,189, 5,736,152, 4,667,014, 4,748,034 and -295,239,660), or diffusional systems in which an active component controls the release rate (for example, as described in U.S. Pat. Nos. 3,832,253, 3,854, 480, 5,133,974 and 5,407,686). The formulation may be as, for example, microspheres, hydrogels, polymeric reservoirs, cholesterol matrices, or polymelic systems. In some embodiments, the system may allow sustained or controlled release of the composition to occur, for example, through control of the diffusion or erosion/degradation rate of the formulation containing the composition. In addition, a pump-based hardware delivery system can be used to deliver one or more embodiments of the compositions or preparations described herein. Use of a long-term sustained release formulations or implants can be particularly suitable for treatment of chronic conditions, such as diabetes. Long-term release, as used herein, means that a formulation or an implant is made and arranged to deliver compositions or preparations described herein at a therapeutic level for at least 30 days, or at least 60 days. In some embodiments, the long-term release refers to a formulation or an implant being configured to deliver an active agent at a therapeutic level over several months.

Methods for Preparing a Storage-Stable Composition

Provided are methods for preparing storage-stable compositions as described herein. In some embodiments, the storage-stable compositions are immunogenic. The method includes providing or obtaining a silk fibroin matrix comprising at least one active agent, in which the at least one active agent retains at least about 30% of its original bioactivity upon storage or transported for a period of time under a specified condition. In some embodiments, the method further comprises mixing, or adding at least one active agent in a silk fibroin matrix. In some embodiments, the method further comprises drying the silk fibroin matrix comprising at least one active agent to form a solid-state silk fibroin, in which the at least one active agent retains at least about 30% of its original bioactivity upon storage or transported for a period of time under a specified condition. In these embodiments, the silk fibroin matrix can be a solution or a gel-like solution. The silk fibroin matrix containing at least one active agent can be dried in air or nitrogen, or by lyophilization. In one embodiment, the silk fibroin matrix (e.g., silk solution) containing at least one active agent can be subjected to lyophilization to form lyophilized solid-state silk fibroin loaded with the active agent, in which the at least one active agent retains at least about 60%, at least about 70%, or at least about 80% of its original bioactivity (e.g. viral potency, see e.g. Example 3) upon storage or transport for a period of time (e.g. for at least 6 months, or for up to 6 months) under a specified condition (e.g. storage or transport at 37° C., at 45° C., or at greater than at 45° C.).

In some embodiments, the method can further comprise lyophilization of the solid-state or dried silk fibroin comprising at least one active agent, e.g., to further decrease residual moisture of the composition, in which the at least one active agent retains at least about 60%, at least about 70%, or at least about 80% of its original bioactivity (e.g. viral potency, see e.g. Example 3) upon storage or transport for a period of time (e.g. for at least 6 months, or for up to 6 months) under a specified condition (e.g. storage or transport at 37° C., at 45° C., or at greater than at 45° C.).

In one embodiment, the method of producing a solid-state storage-stable composition includes (a) providing or obtaining a silk fibroin matrix comprising at least one active agent; and (b) drying the silk fibroin matrix comprising the at least one active agent to form a solid-state silk fibroin, in which the at least one active agent retains at least about 30% of its original bioactivity upon storage or transported for a period of time under a specified condition. In some embodiments, the method further comprises step (c) of lyophilizing the solid state silk-fibroin of step (b), e.g. to retain at least about 60%, at least about 70%, or at least about 80% original bioactivity of the active agent at temperatures above 0° C., e.g. greater than 30° C., greater than 37° C., greater than 40° C. In some embodiments, the solid state silk-fibroin of step (b) is subjected to a post treatment, e.g. treatment with methanol, ethanol, shear stress, electric filed, pressure etc., prior to the lyophilization of step (c). In some embodiments the active agent is an immunogenic composition. In one embodiment, the immunogenic composition comprises a monovalent vaccine. In another embodiment, the immunogenic composition comprises a multivalent or polyvalent vaccine, e.g., a divalent vaccine or a trivalent vaccine.

As used herein, the term "a monovalent vaccine" refers to a vaccine that is designed to immunize against a single antigen or single microorganism.

As used herein, the term "a multivalent or polyvalent vaccine" refers to a vaccine that is designed to immunize against two or more different strains of a microorganism, or against two or more different microorganisms. For example, a divalent vaccine is generally a vaccine that is designed to immunize against two different strains of a microorganism or against two different microorganisms. A trivalent vaccine is generally a vaccine that is designed to immunize against three different strains of a microorganism or against three different microorganisms. An exemplary trivalent vaccine is a vaccine that is designed to immunize against measles, mumps, and rubella.

Without wishing to be bound by theory, silk can prevent the virus proteins from undergoing heat-induced aggregation and/or raise the glass-transition temperature of the vaccine (or melting point of a viral protein), thus maintaining infectivity at elevated temperatures. Accordingly, in some embodiments, the method of preparing an immunogenic composition described herein can be employed for decreasing the likelihood of or preventing viral protein aggregation at a temperature at which a virus would otherwise aggregate in the absence of silk matrix. For example, in some embodiments, the method of preparing an immunogenic composition described herein can be used to decrease the likelihood of viral protein aggregation by at least about 10%, at least about 20%, at least about 30%, at least about 40%, at least about 50%, at least about 60%, at least about 70%, at least about 80%, at least about 90%, at least about 95% or more, as compared to an immunogen without the silk fibroin matrix. In some embodiments, viral protein aggregation in an immunogenic composition described herein can be reduced by at least about 1.5 fold, at least about 2-fold, at least about 3-fold, at least about 4-fold, at least about 5-fold, or more, as compared to an immunogen without the silk fibroin matrix. The viral protein aggregation can be determined, e.g., by measuring the effective diameter of viral particles using dynamic light scattering as shown in Example 3.

Stated another way, in some embodiments, the methods of preparing an immunogenic composition described herein can be employed for increasing the viral protein aggregation temperature by at least about 10° C., at least about 20° C., at least about 30° C., at least about 40° C., at least about 50° C., at least about 60° C., at least about 70° C., at least about 80° C., at least about 90° C., at least about 100° C., or higher, as compared to an immunogen without the silk fibroin matrix. The viral protein aggregation temperature can be determined, e.g., by measuring the effective diameter of viral particles over a range of temperatures using dynamic light scattering as shown in Example 3. The temperature at which the effective diameter of viral particles begins to increase can be the viral protein aggregation temperature.

In some embodiments, the methods of preparing an immunogenic composition described herein can be employed for increasing the glass-transition temperature and/or melting point of a vaccine by at least about 10 cc, at least about 20 cc, at least about 30 cc, at least about 40 cc, at least about 50 cc, at least about 60 cc, at least about 70 cc, at least about 80 cc, at least about 90 cc, at least about 100 cc, at least about 125 cc, at least about 150 cc or higher, as compared to an immunogen without the silk fibroin matrix. The glass-transition temperature and/or melting point of a vaccine can be determined, e.g., by differential scanning calorimetry as shown in Example 3.

The aqueous silk fibroin solution used for making a solid-state silk fibroin can be prepared using techniques known in the art. The concentration of silk fibroin in solutions used to embed or carry active agent can be suited to the particular active agent. Any concentration of silk fibroin solution may be used. In one embodiment, e.g. for vaccine stabilization, the concentrations of silk may be at least about 2%, at least about 4%, at least about 5%, at least about 6%, at least about 7%, at least about 8%, at least about 9%, at least about 10%, at least about 12%, at least about 14%, at least about 15%, at least about 16%, at least about 18%, or at least about 20% (w/v), inclusive. Suitable processes for preparing silk fibroin solution are disclosed, for example, in U.S. patent application Ser. No. 11/247,358; WO/2005/012606; and WO/2008/127401. The silk aqueous solution can then be processed into silk matrix such as silk films, conformal coatings or layers, or 3-dimentional scaffolds, or electrospun fibers for further processing into the silk reflectors. A micro-filtration step may be used herein. For example, the prepared silk fibroin solution may be processed further by centrifugation and syringe based micro-filtration before further processing into silk matrix.

Additional polymers, e.g., biocompatible and biodegradable polymers, can also be blended in the silk fibroin. For example, additional biopolymers, such as chitosan, exhibit desirable mechanical properties, can be processed in water, blended with silk fibroin, and form generally films. Other biopolymers, such as chitosan, collagen, gelatin, agarose, chitin, polyhydroxyalkanoates, pullan, starch (amylose amylopectin), cellulose, alginate, fibronectin, keratin, hyaluronic acid, pectin, polyaspartic acid, polylysin, pectin, dextrans, and related biopolymers, or a combination thereof, may be utilized in specific applications, and synthetic biodegradable polymers such as polyethylene oxide, polyethylene glycol, polylactic acid, polyglycolic acid, polycaprolactone, polyorthoester, polycaprolactone, polyfumarate, polyanhydrides, and related copolymers may also be selectively used.

A silk fibroin matrix can be in solution or in a solid state. The solid-state silk fibroin matrix can be in any material format, such as silk fibers, electrospun fibers, films, mats, 3-D scaffolds, dried gels, spheres (including microsphere and/or nanospheres), particles or composites of one or more different formats of silk materials, as described herein. In other embodiments, the solid-state silk fibroin is a particle.

In one embodiment, the solid-state silk fibroin is a silk film. For example, a silk fibroin film can be prepared by depositing an aqueous silk fibroin-containing solution (e.g., silk concentration of about 3% (w/v) to about 30% (w/v), or about 5% (w/v) to about 15% (w/v)) on a support substrate and allowing the silk fibroin solution to dry into a film. In this regard, the substrate coated with silk fibroin-based solution may be exposed in air for a period of time, such as 12 hours. Depositing the silk fibroin solution can be performed by, e.g., using a spin coating method, where the silk fibroin solution is spin coated onto the substrate to allow the fabrication of thin membranes of non-uniform in height; or simply by pouring silk fibroin solution over the top of the substrate. The properties of the silk fibroin film, such as thickness and content of other components, may be altered based on the concentration and/or the volume of the silk fibroin solution applied to the substrate, and the techniques used for processing the silk fibroin solution into silk film. For instance, the thickness of the silk film may be controlled by changing the concentration of the silk fibroin in the solution, or by using desired volumes of silk fibroin solution, resulting silk fibroin film with a thickness ranging from approximately 2 nm to 1 mm thick. In one embodiment, one can spin coat the silk fibroin onto a substrate to create films having thickness from about 2 nm to about 100 min using various concentrations of silk fibroin and spinning speeds.

In some embodiments, instead of drying the silk fibroin solution containing one or more active agents (e.g., immunogens) in gas such air or nitrogen, the active-agent containing silk fibroin solution can be subjected to lyophilization to form lyophilized silk fibroin matrix, e.g., lyophilized silk fibroin film. Subjecting the silk fibroin solution containing one or more active agents (e.g., immunogens such as vaccines) to lyophilization for drying not only improve the initial recovery of the active agent (e.g., immunogens such as vaccines) during the fabrication process, but it also surprisingly provides greater stabilization of the active agent (e.g., immunoagens such as vaccines) at elevated temperatures (e.g., at room temperature or above, or 37° C. or above, or at 45° C. or above) for an extended period of time, e.g., for at least about 1 weeks, at least about 2 weeks, at least about 3 weeks, at least about 4 weeks, at least about 2 months, at least about 3 months, at least about 4 months, at least about 5 months, at least about 6 months or longer.

In some embodiments, the solid-state silk fibroin can be a composite of one or more layers of silk fibroin. Each layer of silk fibroin can possess the same or different composition or properties. For instance, each layer of silk fibroin can possess the same or different concentration of silk fibroin, and/or each layer can possess the same or different mechanical and/or degradation properties. In one embodiment, the solid-state silk fibroin can be a multi-layered silk fibroin, e.g., which can be tuned to reflect specific wavelengths.

In some embodiments, the solid-state silk fibroin can be a silk hydrogel. Methods for making a silk hydrogel are known in the art. For example, a silk hydrogel can be produced by applying a shear stress to a silk fibroin solution (comprising one or more active agents such as immunogens, and silk fibroin at a concentration of about 0.5% (w/v) to about 20% (w/v), or about 1% (w/v) to about 15% (w/v), or about 2% (w/v) to about 10% (w/v)). In such embodiments, the weight ratio of the active agent(s) (e.g., immunogen(s)) to silk solution can range from about 1:10 to about 10:1. In one embodiment, the weight ratio of the active agent(s) (e.g., immunogen(s)) to silk solution can be around 1:1. See, e.g., International App. No.: WO 2011/005381, the content of which is incorporated herein by reference for methods of producing vortex-induced silk fibroin gelation for encapsulation and delivery. Without limitations, other methods for making a silk hydrogel with one or more active agents such as immunogens distributed herein can also be used, such as by sonication (e.g., U.S. Pat. App. No. U.S. 2010/0178304 and International App. No.: WO 2008/150861), or by pH adjustment (e.g., U.S. App. No.: US 2011/0171239). The contents of those patent applications are incorporated herein by reference.

In some embodiments, the solid-state silk fibroin can include a silk microsphere. Various methods of producing silk microspheres or nanospheres are known in the art. In some embodiments, the silk microparticles or nanoparticles can be produced by a polyvinyl alcohol (PVA) phase separation method as described in, e.g., International App. No. WO 2011/041395, the content of which is incorporated herein by reference. In such embodiments, the silk concentration used in the PVA phase separation method can range from about 0.5% (w/v) to about 20% (w/v), or about 1% (w/v) to about 15% (w/v), or about 3% (w/v) to about 10% (w/v). In one embodiment, the silk concentration used in the PVA phase separation method can be about 5% (w/v). In some embodiments, the weight ratio of active agent(s) (e.g., immunogen(s)) to silk solution can be about 1:300 to about 1:2000, or about 1:500 to about 1:1500. In one embodiment, the weight ratio of active agent(s) (e.g., immunogen(s)) to silk solution can be about 1:1000. Other methods for producing silk microspheres or nanospheres, e.g., described in U.S. App. No. U.S. 2010/0028451 and International App. No.: WO 2008/118133 (using lipid as a template for making silk microspheres or nanospheres), and in Wenk et al. J Control Release 2008; 132: 26-34 (using spraying method to produce silk microspheres or nanospheres) can be used for the purpose of making silk microparticles or nanoparticles encapsulating an active agent such as an immunogen described herein.

In some embodiments, the silk microspheres or nanospheres can be further embedded in a biopolymer, e.g., to prolong the release of an active agent such as an immunogen over a period of time. In some embodiments, the biopolymer can be a silk hydrogel to encapsulate the active agent (e.g., immunogen)-loaded silk microspheres or nanospheres. See, e.g., International App. No.: WO 2010/141133 for methods of producing silk fibroin scaffolds for antibiotic delivery.

In some embodiments, the solid-state silk fibroin compositions (storage-stable compositions described herein) can be subjected to post-treatment, e.g., to modify the degradation rate of the silk fibroin. Additional treatment can include, but are not limited to, organic solvent treatment, mechanical treatment, or electromagnetic treatment. By way of example, the degradation rate of the silk fibroin can be controlled, e.g., by modifying the amount of beta-sheet crystal, and/or crystal orientation. Accordingly, the amount of beta-sheet crystal, and/or crystal orientation in a silk fibroin can be controlled by contacting the silk fibroin with alcohol, e.g., methanol or ethanol, as established in the art. In some embodiments, the silk fibroin can be subjected to a mechanical force, e.g., stretching or shear stress to vary the amount beta-sheet crystal, and/or alignment of the crystal orientation. In some embodiments, the silk fibroin can be subjected to an electric filed or pressure. In some embodiments, the silk fibroin can be contacted with salt.

Without wishing to be bound by theory, the release rate of an active agent from a silk fibroin matrix can be controlled by the content of beta-sheet crystalline structures, silk concentration and/or porosity of the silk fibroin matrix. Methods for forming pores in a silk matrix are known in the art, e.g., porogen-leaching method, freeze-drying method, and/or gas-forming method. Such methods are described, e.g., in U.S. Pat. App. Nos.: US 2010/0279112, US 2010/0279112, and U.S. Pat. No. 7,842,780, the contents of which are incorporated herein by reference.

In some embodiments, the methods of preparing storage-stable compositions described herein can further comprise reducing the dried solid-state silk fibroin by a mechanical means to obtain micronized particles as defined herein. Exemplary mechanical means to obtain micronized particles include micronizing, pulverizing, crushing, grinding, freeze-drying or any combination thereof.

In accordance with the conventional practice, the compositions described herein are desirably processed under aseptic conditions using components which preliminarily have been rendered bacterially sterile. Sterility on storage can be maintained by incorporation of an antigen-compatible germicidal substance such as thimerosal.

Kits and Devices

Packages and kits comprising at least one storage-stable composition or preparation are also described herein. The packages can be prepared in various types of containers, which can be selected from the group consisting of a vial, an ampule, a capsule, a tube, a delivery device, a bottle, and a packet. In some embodiments, the delivery device is a syringe. In some embodiments, the syringe can be needle-less. The storage-stable composition contained in a package can be in a form of a hydrogel, gel-like particles, powder, microspheres, nanospheres, or any combinations thereof. In some embodiments, the storage-stable composition contained in a package can be lyophilized. In some embodiments, the storage-stable composition can be loaded in a syringe for injection.

Kits provided herein comprise a package described herein, and a pharmaceutically acceptable solution, e.g., PBS. In some embodiments, the kits can further comprise at least one delivery device for administering a composition or a preparation described herein to a subject. In other embodiments, the kits can further comprise a disinfectant. In certain embodiments, such packages, and kits described herein can be used for vaccination purposes.

As used herein, a "subject" means a human or animal. Usually the animal is a veliebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In certain embodiments of the aspects described herein, the subject is a mammal, e.g., a primate, e.g., a human. A subject can be male or female. Preferably, the subject is a mammal. The mammal can be a human, non-human primate, mouse, rat, dog, cat, horse, or cow, but are not limited to these examples. In addition, the methods and compositions described herein can be used to treat domesticated animals and/or pets.

Delivery devices pre-loaded with at least one composition or preparation described herein are also within the scope of various aspects described herein. Embodiments of a delivery device comprises at least one chamber with an outlet, wherein the at least one chamber comprises a pre-determined amount of the composition described herein, and the outlet provides an exit for the composition.

The term "chamber" as used herein refers to any structure configured to store and/or convey a composition described herein. The chamber can be of any shape or any size, depending on users' applications, needs, and/or preferences. An exemplary chamber includes, but is not limited to, a barrel, a tube, a cassette, and a depression, e.g., a microwell.

In some embodiments, the delivery device described herein can further comprise an actuator to control release of the composition through the outlet, thereby administering the composition therein to a subject. As used herein, the term "an actuator" is a mechanical device that can convert any kind of energy to move the composition through the outlet of the device. By way of example, an actuator can convert electrical energy to move or control release of the composition through the outlet. In some embodiments, an actuator can convert pressure to remove or control release composition through the outlet. For example, a plunger of a syringe converts force or pressure to release a composition from the barrel (chamber), thereby injecting the composition to a subject.

Examples of delivery devices described herein include, but are not limited to, a syringe, a dry powder injector, a nasal spray, a nebulizer, and an implant. In some embodiments, an implant can be a microchip, e.g., the ones described in U.S. Pat. Nos. 5,797,898; 6,669,683; 7,052,488; and 7,582,080. In some embodiments, the delivery devices can be used for vaccination. In such embodiments, vaccine delivery devices/systems can include, but are not limited to, the ones described in U.S. Patent Application Nos.: US 2004/0133160; US 2004/0096455; US 2005/0112135; US 2005/0123565; US 2009/0043280; and US 2009/0143724, as well as U.S. Pat. Nos. 5,346,481; and 5,900,238.

The term "pre-determined amount" is generally used in reference to an amount of a composition desired and/or determined by a user, e.g., depending on applications or treatment. In some embodiments, the term "pre-determined amount" refers to an amount of a composition effective to treat or prevent a disease or a disorder, e.g., increasing immunity to the disease; reducing, inhibiting or delaying at least one symptom of the disease; or producing an improvement in the disease, for example, beneficial or desired clinical results. For the purposes of various aspects described herein, beneficial or desired clinical results include, but are not limited to, alleviation of one or more symptoms, diminishment of extent of disease, stabilized (e.g., not worsening) state of disease, delay or slowing of disease progression, amelioration or palliation of the disease state, and remission (whether partial or total), whether detectable or undetectable. In some embodiments, treating can refer to prolonging survival as compared to expected survival if not receiving treatment. Thus, one of skill in the art realizes that a treatment may improve the disease condition, but may not be a complete cure for the disease. In reference to immunogenic or vaccine compositions, the term "pre-determined amount" can mean an amount of the composition effective to provide or increase immunity to a particular disease. A blood test or any methods known to a skilled artisan can be used to check immunity. Accordingly, in some embodiments, the delivery device comprises an effective dose of immunogenic or vaccine composition.

Embodiments of the various aspects described herein can be illustrated by the following numbered paragraphs.

1. A method comprising a step of: maintaining a composition, wherein the composition comprises a silk fibroin matrix and at least one active agent distributed therein, and wherein the active agent retains at least about 30% of its original bioactivity when the composition is (a) subjected to at least one freeze-thaw cycle, or (b) maintained for at least about 24 hours at a temperature above 0° C., or (c) both (a) and (b).
2. The method of paragraph 1, wherein the active agent retains at least about 50% of its original bioactivity.
3. The method of paragraph 1 or 2, wherein the active agent retains at least about 80% of its original bioactivity.
4. The method of any of paragraphs 1-3, wherein the composition is maintained for at least about 1 month.
5. The method of any of paragraphs 1-4, wherein the composition is maintained for at least about 6 months.
6. The method of any of paragraphs 1-5, wherein the composition is a film, a fiber, a particle, a gel, or a hydrogel.

The method of any of paragraphs 1-6, wherein the composition is lyophilized.

8. The method of any of paragraphs 1-7, wherein the composition is micronized.
9. The method of paragraph 8, wherein the micronized composition are nanoparticles or microparticles.
10. The method of paragraph 9, wherein the nanoparticles or microparticles have a size of about 10 nm to about 1000 µm.
11. The method of any of paragraphs 1-10, wherein the composition further comprises an additive.
12. The method of paragraph 11, wherein the additive is selected from a stabilizing agent, a pharmaceutically acceptable carrier or any combinations thereof.
13. The method of any of paragraphs 1-12, wherein the composition is maintained at a temperature of about 0° C. to above room temperature.
14. The method of paragraph 13, wherein the composition is maintained at a temperature of about room temperature to about 37° C.
15. The method of any of paragraphs 1-14, wherein the composition is maintained at a temperature greater than 37° C.
16. The method of any of paragraphs 1-15, wherein the composition is maintained under exposure to light.
17. The method of any of paragraphs 1-16, wherein the composition is maintained at a relative humidity of at least about 10%.
18. The method of any of paragraphs 1-17, wherein the active agent is selected from the group consisting of proteins, peptides, antigens, immunogens, vaccines, antibodies or portions thereof, antibody-like molecules, enzymes, nucleic acids, siRNA, shRNA, aptamers, viruses, bacteria, small molecules, cells, photosynthetic and energy-harvesting compounds, flavors, antibiotics, therapeutic agents, diagnostic agents, viral vectors, and anti-venom.
19. The method of any of paragraphs 1-18, wherein the active agent is an immunogen.
20. The method of paragraph 19, wherein the immunogen is selected from the group consisting of killed pathogens, live attenuated pathogens, protein subunits and conjugate thereof, inactivated toxins, and synthetic peptides, carbohydrates and antigens.
21. The method of paragraph 19 or 20, wherein the immunogen is derived from hepatitis B virus, *Haemophilus influenzae* Type B, poliovirus, *Neisseria meningitides* C, influenza, *Varicella*, or *Mycobacteria tuberculosis bacille* Calmette-Guerin, tetanus toxoid, diphtheria toxoid, and *Bordetella pertussis*.
22. The method of paragraph 19 or 20, wherein the immunogen is a combination immunogen selected from the group consisting of DTaP, DTwP, DTwP hepB, DTP hep B Hib, DTaP hep B Hib IPV, and any combinations thereof.
23. The method of paragraph 19 or 20, wherein the immunogen is live, attenuated virus.
24. The method of paragraph 23, wherein the live, attenuated virus is an enveloped virus.
25. The method of paragraph 24, wherein the enveloped virus is selected from the group consisting of Paramyxoviridae, Togaviridae, Orthomyxovilidae, Flaviviridae, Herpesviridae, Rhabdovirus, Retroviridae, and any combinations thereof.
26. The method of any of paragraphs 23-25, wherein the virus is varicella.
27. The method of any of paragraphs 23-25, wherein the virus is influenza.
28. The method of paragraph 23, wherein the live, attenuated virus causes measles, mumps, or rubella.
29. The method of paragraph 19 or 20, wherein the immunogen is a live, attenuated, non-enveloped virus.
30. The method of paragraph 29, wherein the non-enveloped virus is rotavirus, reovirus, hepatitis virus, rabies virus or poliovirus.
31. The method of paragraph 19, wherein the immunogen is a bacterium.
32. The method of paragraph 31, wherein the bacterium is *Mycobacteria tuberculosis bacille* Calmette-Guérin or *Bordetella pertussis*.
33. The method of paragraph 19, wherein the immunogen is a bacterial subunit.
34. The method of paragraph 33, wherein the bacterial subunit is derived from *Neisseria meningitides* type C, *Haemophilus influenzae* type B, *Streptococcus pneumoniae*, or Group B *streptococcus*.
35. The method of paragraph 33, wherein the bacterial subunit is a polysaccharide.
36. The method of paragraph 19, wherein the immunogen is a viral subunit.
37. The method of paragraph 36, wherein the viral subunit is derived from Hepatitis B virus or Human Papillomavirus.
38. The method of paragraph 19, wherein the immunogen is recombinant.
39. The method of paragraph 19, wherein the immunogen is a vaccine product selected from the group consisting of Anthrax vaccine (BioThrax); BCG (*Bacillus Calmette-Guérin*) (Tice, Mycobax); DTaP (Daptacel); DTaP (Infanrix); DTaP (Tripedia); DTaP/Hib (TriHIBit); DTaP-IPV (Kinrix); DTaP-HepB-IPV (Pediarix); DtaP-IPV/Hib (Pentacel); DT (diphtheria vaccine plus tetanus vaccine) (Sanofi); Hib vaccine (ACTHib); DT (Massachusetts); Hib (PedvaxHib); Hib/Hep B (Comvax); Hep A (Havrix), Hepatitis A vaccine; Hep A (Vaqta), Hepatitis A vaccine; Hep B (Engerix-B), Hepatitis B vaccine; Hep B (Recombivax), Hepatitis B vaccine; HepA/HepB vaccine (Twinrix); Human Papillomavirus (HPV) (Gardasil); Influenza vaccine (Afluria); Influenza vaccine (Fluarix); Influenza vaccine (Flulaval); Influenza vaccine (Fluvirin); Influenza vaccine (Fluzone); Influenza vaccine (FluMist); IPV (Ipol), Polio vaccine; Japanese encephalitis vaccine (JE-Vax); Japanese encephalitis vaccine (Ixiaro); Meningococcal vaccine (Menactra); MMR vaccine (MMR-II); MMRV vaccine (ProQuad); Pneumococcal vaccine (Pneumovax); Pneumococcal vaccine (Prevnar); Poliovirus inactivated (Poliovax), Polio vaccine; Rabies vaccine (Imovax); Rabies vaccine (RabAvert); Rotavirus vaccine (RotaTeq); Rotavirus vaccine (Rotarix); Td vaccine (Decavac); Td vaccine (Massachusetts); Tdap vaccine (Adacel); Tdap vaccine (Boostrix); Typhoid (inactivated-Typhim Vi), Typhus vaccine; Typhoid (oral-Ty21a), Typhus vaccine; Vaccinia (ACAM2000); *Varicella* vaccine (Vaiivax); Yellow fever vaccine (YF-Vax); Zoster vaccine (Zostavax); and any combinations thereof.
40. The method of any of paragraphs 1-39, wherein the ratio of the silk fibroin matrix to the active agent is about 1:1000 to about 1000:1.
41. A storage-stable composition comprising a silk fibroin matrix and an active agent distributed therein, wherein the active agent retains at least about 30% of its original bioactivity when the composition is (a) subjected to at least one freeze-thaw cycle, or (b) maintained for at least about 24 hours at a temperature above 0° C., or (c) both (a) and (b).
42. The composition of paragraph 41, wherein the active agent retains at least about 50% of its original bioactivity.
43. The composition of paragraph 41 or 42, wherein the active agent retains at least about 80% of its original bioactivity.
44. The composition of any of paragraphs 41-43, wherein the composition is maintained for at least about 1 month.
45. The composition of any of paragraphs 41-44, wherein the composition is maintained for at least about 6 months.
46. The composition of any of paragraphs 41-45, wherein the composition is a film, a fiber, a particle, a gel, or a hydrogel.
47. The composition of any of paragraphs 41-46, wherein the composition is lyophilized.
48. The composition of any of paragraphs 41-47, wherein the composition is micronized.
49. The composition of paragraph 48, wherein the micronized composition are nanoparticles or microparticles.
50. The composition of paragraph 49, wherein the nanoparticles or microparticles have a size of about 10 nm to about 1000 μm.
51. The composition of any of paragraphs 41-50, further comprising an additive distributed through the silk fibroin matrix.
52. The composition of paragraph 51, wherein the additive is selected from a stabilizing agent, a pharmaceutically acceptable carrier, or any combinations thereof.
53. The composition of any of paragraphs 41-52, wherein the composition is maintained at a temperature of about 0° C. to above room temperature.
54. The composition of any of paragraphs 41-53, wherein the composition is maintained at a temperature of about room temperature to about 37° C.
55. The composition of any of paragraphs 41-54, wherein the composition is maintained at a temperature greater than 37° C.
56. The composition of any of paragraphs 41-55, wherein the composition is maintained under exposure to light.
57. The composition of any of paragraphs 41-56, wherein the composition is maintained at a relative humidity of at least about 10%.
58. The composition of any of paragraph 41-57, wherein the active agent is selected from the group consisting of proteins, peptides, antigens, immunogens, vaccines, antibodies or portions thereof, antibody-like molecules, enzymes, nucleic acids, siRNA, shRNA, aptamers, viruses, bacteria, small molecules, cells, photosynthetic and energy-harvesting compounds, flavors, antibiotics, therapeutic agents, diagnostic agents, viral vectors, anti-venom, and any combinations thereof.
59. The composition of any of paragraphs 41-58, wherein the active agent is an immunogen.
60. The composition of paragraph 59, wherein the immunogen is selected from the group consisting of killed pathogens, live attenuated pathogens, protein subunits and conjugate thereof, inactivated toxins, and synthetic peptides, carbohydrates and antigens.
61. The composition of paragraph 59 or 60, wherein the immunogen is derived from hepatitis B virus, *Haemophilus influenzae* Type B, poliovirus, *Neisseria meningitides* C, influenza, *Varicella*, or *Mycobacteria tuberculosis bacille* Calmette-Guérin, tetanus toxoid, diphtheria toxoid, and *Bordetella pertussis*.
62. The composition of paragraph 59 or 60, wherein the immunogen is a combination immunogen selected from the group consisting of DTaP, DTwP, DTwP hepB, DTP hep B Hib, DTaP hep B Hib IPV, and any combinations thereof.
63. The composition of paragraph 59 or 60, wherein the immunogen is live, attenuated virus.
64. The composition of paragraph 63, wherein the live, attenuated virus is an enveloped virus.
65. The composition of paragraph 64, wherein the enveloped virus is selected from the group consisting of Paramyxoviridae, Togaviridae, Orthomyxoviridae, Flaviviridae, Herpesviridae, Rhabdovirus, Retroviridae, and any combinations thereof.
66. The composition of any of paragraphs 63-65, wherein the virus is varicella.
67. The composition of any of paragraphs 63-65, wherein the virus is influenza.
68. The composition of paragraph 63, wherein the live, attenuated virus causes measles, mumps, or rubella.
69. The composition of paragraph 59 or 60, wherein the immunogen is a live, attenuated, non-enveloped virus
70. The composition of paragraph 69, wherein the non-enveloped virus is rotavirus, reovirus, hepatitis virus, rabies virus or poliovirus.
71. The composition of paragraph 59, wherein the immunogen is a bacterium.
72. The composition of paragraph 71, wherein the bacterium is *Mycobacteria tuberculosis bacille* Calmette-Guérin or *Bordetella pertussis*.
73. The composition of paragraph 59, wherein the immunogen is a bacterial subunit.
74. The composition of paragraph 73, wherein the bacterial subunit is derived from *Neisseria meningitides* type C, *Haemophilus influenzae* type B, *Streptococcus pneumoniae*, or Group B *streptococcus*.

75. The composition of paragraph 73, wherein the bacterial subunit is a polysaccharide.

76. The composition of paragraph 59, wherein the immunogen is a viral subunit.

77. The composition of paragraph 76, wherein the viral subunit is derived from Hepatitis B virus or Human Papillomavirus.

78. The composition of paragraph 59, wherein the immunogen is recombinant.

79. The composition of paragraph 59, wherein the immunogen is a vaccine product selected from the group consisting of Anthrax vaccine (BioThrax); BCG (*Bacillus* Calmette-Guerin) (Tice, Mycobax); DTaP (Daptacel); DTaP (Infanrix); DTaP (Tripedia); DTaP/Hib (TriHIBit); DTaP-IPV (Kinrix); DTaP-HepB-IPV (Pediarix); DtaP-IPV/Hib (Pentacel); DT (diphtheria vaccine plus tetanus vaccine) (Sanofi); Hib vaccine (ACTHib); DT (Massachusetts); Hib (PedvaxHib); Hib/Hep B (Comvax); Hep A (Havrix), Hepatitis A vaccine; Hep A (Vaqta), Hepatitis A vaccine; Hep B (Engerix-B), Hepatitis B vaccine; Hep B (Recombivax), Hepatitis B vaccine; HepA/HepB vaccine (Twinrix); Human Papillomavirus (HPV) (Gardasil); Influenza vaccine (Afluria); Influenza vaccine (Fluarix); Influenza vaccine (Flulaval); Influenza vaccine (Fluvirin); Influenza vaccine (Fluzone); Influenza vaccine (FluMist); IPV (Ipol), Polio vaccine; Japanese encephalitis vaccine (JE-Vax); Japanese encephalitis vaccine (Ixiaro); Meningococcal vaccine (Menactra); MMR vaccine (MMR-II); MMRV vaccine (ProQuad); Pneumococcal vaccine (Pneumovax); Pneumococcal vaccine (Prevnar); Poliovirus inactivated (Poliovax), Polio vaccine; Rabies vaccine (Imovax); Rabies vaccine (RabAvert); Rotavirus vaccine (RotaTeq); Rotavirus vaccine (Rotarix); Td vaccine (Decavac); Td vaccine (Massachusetts); Tdap vaccine (Adacel); Tdap vaccine (Boostrix); Typhoid (inactivated-Typhim Vi), Typhus vaccine; Typhoid (oral-Ty21a), Typhus vaccine; Vaccinia (ACAM2000); *Varicella* vaccine (Varivax); Yellow fever vaccine (YF-Vax); Zoster vaccine (Zostavax); and any combinations thereof.

80. The composition of any of paragraphs 41-79, wherein the ratio of the silk fibroin matrix to the active agent is about 1:1000 to about 1000:1.

81. A method for preparing a storage-stable composition of any of paragraphs 41 to 80, the method comprising the steps of:
  a. providing a silk fibroin solution comprising at least one active agent; and
  b. drying the silk fibroin solution of step (a) to form a solid-state silk fibroin, thereby obtaining a composition in which the at least one active agent retains at least about 30% of its original bioactivity upon storage.

82. The method of paragraph 81, wherein the drying is lyophilization.

83. The method of paragraph 81, wherein the drying is air-dry.

84. The method of any of paragraphs 81-83, further comprising lyophilizing the solid-state silk fibroin from step (b).

85. The method of any of paragraphs 81-84, further comprising post-treatment of the composition.

86. The method of paragraph 85, wherein the post-treatment alters the crystallinity of the composition.

87. The method of paragraph 85 or 86, wherein the post-treatment is contacting the composition with methanol or ethanol.

88. The method of any of paragraphs 85-87, wherein the post-treatment is subjecting the composition to shear stress.

89. The method of any of paragraphs 85-88, wherein the post-treatment is subjecting the composition to an electric field.

90. The method of any of paragraphs 85-89, wherein the post-treatment is subjecting the composition to pressure.

91. The method of any of paragraphs 85-90, wherein the post-treatment is contacting the composition with salt.

92. The method of any of paragraphs 81-91, further comprising reducing the solid-state silk fibroin of step (b) by a mechanical means to obtain micronized particles.

93. The method of paragraph 92, wherein the mechanical means is selected from micronizing, pulverizing, crushing, grinding, freeze-drying or any combinations thereof.

94. The method of paragraph 92 or 93, wherein the micronized particles have a size of about 10 nm to about 1000 μm.

95. The method of any of paragraphs 81-94, wherein the at least one active agent retains at least about 80% of its original bioactivity upon storage.

96. The method of any of paragraphs 81-95, wherein the storage is over a period of at least about 6 months.

97. The method of any of paragraphs 81-96, wherein the storage is at a temperature of about room temperature to about 37° C.

98. The method of any of paragraphs 81-97, wherein the storage is at a temperature greater than 37° C.

99. A method comprising a step of maintaining an immunogenic composition, wherein the composition comprises a silk fibroin matrix and at least one immunogen distributed therein, and wherein the immunogen retains at least about 30% of its original immunogenicity when the composition is (a) subjected to at least one freeze-thaw cycle, or (b) maintained for at least about 24 hours at a temperature above 0° C., or (c) both (a) and (b).

100. The method of paragraph 99, wherein the immunogen retains at least about 50% of its original immunogenicity.

101. The method of paragraph 99 or 100, wherein the immunogen retains at least about 80% of its original immunogenicity.

102. The method of any of paragraphs 99-101, wherein the composition is maintained for at least about 1 month.

103. The method of any of paragraphs 99-102, wherein the composition is maintained for at least about 6 months.

104. The method of any of paragraphs 99-103, wherein the composition is a film, a fiber, a particle, a gel, or a hydrogel.

105. The method of any of paragraphs 99-104, wherein the composition is lyophilized.

106. The method of any of paragraphs 99-105, wherein the composition is micronized.

107. The method of paragraph 106, wherein the micronized composition are nanoparticles or microparticles.

108. The method of paragraph 107, wherein the nanoparticles or microparticles have a size of about 10 nm to about 1000 μm.

109. The method of any of paragraphs 99-108, wherein the composition further comprises an additive distributed through the silk fibroin matrix.
110. The method of paragraph 109, wherein the additive is selected from the group consisting of a stabilizing agent, a pharmaceutically acceptable carrier, and any combinations thereof.
111. The method of paragraph 110, wherein the stabilizing agent is selected from the group consisting of a saccharide, a sugar alcohol, an ion, a surfactant, and any combinations thereof.
112. The method of paragraph 111, wherein the saccharide is sucrose.
113. The method of any of paragraphs 99-112, wherein the composition is maintained at a temperature of about 0° C. to above room temperature.
114. The method of any of paragraphs 99-113, wherein the composition is maintained at a temperature of about room temperature to about 37° C.
115. The method of any of paragraphs 99-114, wherein the composition is maintained at a temperature greater than 37° C.
116. The method of any of paragraphs 99-115, wherein the composition is maintained under exposure to light.
117. The method of any of paragraphs 99-116, wherein the composition is maintained at a relative humidity of at least about 10%.
118. The method of any of paragraphs 99-117, wherein the immunogen is selected from the group consisting of killed pathogens, live attenuated pathogens, protein subunits and conjugate thereof, inactivated toxins, synthetic peptides, carbohydrates, antigens, and any combinations thereof.
119. The method of any of paragraphs 99-118, wherein the immunogen is derived from hepatitis B virus, *Haemophilus influenzae* Type B, poliovirus, *Neisseria meningitides* C, influenza, *Varicella*, or *Mycobacteria tuberculosis bacille* Calmette-Guérin, tetanus toxoid, diphtheria toxoid, and *Bordetella pertussis*.
120. The method of any of paragraphs 99-118, wherein the immunogen is a combination immunogen selected from the group consisting of DTaP, DTwP, DTwP hepB, DTP hep B Hib, DTaP hep B Hib IPV, and any combinations thereof.
121. The method of any of paragraphs 99-118, wherein the immunogen is live, attenuated virus.
122. The method of paragraph 121, wherein the live, attenuated virus is an enveloped virus.
123. The method of paragraph 122, wherein the enveloped virus is selected from the group consisting of Paramyxoviridae, Togaviridae, Orthomyxoviridae, Flaviviridae, Herpesviridae, Rhabdovirus, Retroviridae, and any combinations thereof.
124. The method of paragraph 121-123, wherein the virus is varicella.
125. The method of paragraph 121-123, wherein the virus is influenza.
126. The method of paragraph 121, wherein the live, attenuated virus causes measles, mumps, or rubella.
127. The method of any of paragraphs 99-118, wherein the immunogen is a live, attenuated, non-enveloped virus.
128. The method of paragraph 127, wherein the non-enveloped virus is rotavirus, reovirus, hepatitis virus, rabies virus or poliovirus.
129. The method of any of paragraphs 99-118, wherein the immunogen is a bacterium.
130. The method of paragraph 129, wherein the bacterium is *Mycobacteria tuberculosis* bacille Calmette-Guérin or *Bordetella pertussis*.
131. The method of any of paragraphs 99-118, wherein the immunogen is a bacterial subunit.
132. The method of paragraph 131, wherein the bacterial subunit is derived from *Neisseria meningitides* type C, *Haemophilus influenzae* type B, *Streptococcus pneumoniae*, or Group B *streptococcus*.
133. The method of paragraph 131, wherein the bacterial subunit is a polysaccharide.
134. The method of any of paragraphs 99-118, wherein the immunogen is a viral subunit.
135. The method of paragraph 134, wherein the viral subunit is derived from Hepatitis B virus or Human Papillomavirus.
136. The method of any of paragraphs 99-118, wherein the immunogen is recombinant.
137. The method of any of paragraphs 99-118, wherein the immunogen is a vaccine product selected from the group consisting of Anthrax vaccine (BioThrax); BCG (*Bacillus* Calmette-Guerin) (Tice, Mycobax); DTaP (Daptacel); DTaP (Infanrix); DTaP (Tripedia); DTaP/Hib (TriHIBit); DTaP-IPV (Kinrix); DTaP-HepB-IPV (Pediarix); DtaP-IPV/Hib (Pentacel); DT (diphtheria vaccine plus tetanus vaccine) (Sanofi); Hib vaccine (ACTHib); DT (Massachusetts); Hib (PedvaxHib); Hib/Hep B (Comvax); Hep A (Havrix), Hepatitis A vaccine; Hep A (Vaqta), Hepatitis A vaccine; Hep B (Engerix-B), Hepatitis B vaccine; Hep B (Recombivax), Hepatitis B vaccine; HepA/HepB vaccine (Twinrix); Human Papillomavirus (HPV) (Gardasil); Influenza vaccine (Afluria); Influenza vaccine (Fluarix); Influenza vaccine (Flulaval); Influenza vaccine (Fluvirin); Influenza vaccine (Fluzone); Influenza vaccine (FluMist); IPV (Ipol), Polio vaccine; Japanese encephalitis vaccine (JE-Vax); Japanese encephalitis vaccine (Ixiaro); Meningococcal vaccine (Menactra); MMR vaccine (MMR-II); MMRV vaccine (ProQuad); Pneumococcal vaccine (Pneumovax); Pneumococcal vaccine (Prevnar); Poliovirus inactivated (Poliovax), Polio vaccine; Rabies vaccine (Imovax); Rabies vaccine (RabAvert); Rotavirus vaccine (RotaTeq); Rotavirus vaccine (Rotarix); Td vaccine (Decavac); Td vaccine (Massachusetts); Tdap vaccine (Adacel); Tdap vaccine (Boostrix); Typhoid (inactivated-Typhim Vi), Typhus vaccine; Typhoid (oral-Ty21a), Typhus vaccine; Vaccinia (ACAM2000); *Varicella* vaccine (Varivax); Yellow fever vaccine (YF-Vax); Zoster vaccine (Zostavax); and any combinations thereof.
138. The method of any of paragraphs 99-137, wherein the ratio of the silk fibroin matrix to the immunogen is about 1:1000 to about 1000:1.
139. A storage-stable immunogenic composition comprising a silk fibroin matrix and an immunogen distributed therein, wherein the immunogen retains at least about 30% of its original immunogenicity when the composition is (a) subjected to at least one freeze-thaw cycle, or (b) maintained for at least about 24 hours at a temperature above 0° C., or (c) both (a) and (b).
140. The composition of paragraph 139, wherein the immunogen retains at least about 50% of its original immunogenicity.
141. The composition of paragraph 139 or 140, wherein the immunogen retains at least about 80% of its original immunogenicity.

142. The composition of any of paragraphs 139-141, wherein the composition is maintained for at least about 1 month.

143. The composition of any of paragraphs 139-142, wherein the composition is maintained for at least about 6 months.

144. The composition of any of paragraphs 139-143, wherein the composition is a film, a fiber, a particle, a gel or a hydrogel.

145. The composition of any of paragraphs 139-144, wherein the composition is lyophilized.

146. The composition of any of paragraphs 139-145, wherein the composition is micronized.

147. The composition of paragraph 146, wherein the micronized composition are nanoparticles or microparticles.

148. The composition of paragraph 147, wherein the nanoparticles or microparticles have a size of about 10 nm to about 1000 μm.

149. The composition of any of paragraphs 139-148, further comprising an additive distributed through the silk fibroin matrix.

150. The composition of paragraph 149, wherein the additive is selected from the group consisting of a stabilizing agent, a pharmaceutically acceptable carrier, and any combinations thereof.

151. The composition of paragraph 150, wherein the stabilizing agent is selected from the group consisting of a saccharide, a sugar alcohol, an ion, a surfactant, and any combinations thereof.

152. The composition of paragraph 151, wherein the saccharide is sucrose.

153. The composition of any of paragraphs 139-152, wherein the composition is maintained at a temperature of about 0° C. to above room temperature.

154. The composition of any of paragraphs 139-153, wherein the composition is maintained at a temperature of about room temperature to about 37° C.

155. The composition of any of paragraphs 139-154, wherein the composition is maintained at a temperature greater than 37° C.

156. The composition of any of paragraphs 139-155, wherein the composition is maintained under exposure to light.

157. The composition of any of paragraphs 139-156, wherein the composition is maintained at a relative humidity of at least about 10%.

158. The composition of any of paragraphs 139-157, wherein the immunogen is selected from the group consisting of killed pathogens, live attenuated pathogens, protein subunits and conjugate thereof, inactivated toxins, synthetic peptides, carbohydrates, antigens and any combinations thereof.

159. The composition of any of paragraphs 139-158, wherein the immunogen is derived from hepatitis B virus, *Haemophilus influenzae* Type B, poliovirus, *Neisseria meningitides* C, influenza, *Varicella*, or *Mycobacteria tuberculosis bacille* Calmette-Guérin, tetanus toxoid, diphtheria toxoid, and *Bordetella pertussis*.

160. The composition of any of paragraphs 139-158, wherein the immunogen is a combination immunogen selected from the group consisting of DTaP, DTwP, DTwP hepB, DTP hep B Hib, DTaP hep B Hib IPV, and any combinations thereof.

161. The composition of any of paragraphs 139-158, wherein the immunogen is live, attenuated virus.

162. The composition of paragraph 161, wherein the live, attenuated virus is an enveloped virus.

163. The composition of paragraph 162, wherein the enveloped virus is selected from the group consisting of Paramyxoviridae, Togaviridae, Orthomyxoviridae, Flaviviridae, Herpesviridae, Rhabdovirus, Retroviridae, and any combinations thereof.

164. The composition of paragraph 161-163, wherein the virus is varicella.

165. The composition of paragraph 161-163, wherein the virus is influenza.

166. The composition of paragraph 161, wherein the live, attenuated virus causes measles, mumps, or rubella.

167. The composition of any of paragraphs 139-158, wherein the immunogen is a live, attenuated, non-enveloped virus.

168. The composition of paragraph 167, wherein the non-enveloped virus is rotavirus, reovirus, hepatitis virus, rabies virus or poliovirus.

169. The composition of any of paragraphs 139-158, wherein the immunogen is a bacterium.

170. The composition of paragraph 169, wherein the bacterium is *Mycobacteria tuberculosis bacille* Calmette-Guérin or *Bordetella pertussis*.

171. The composition of any of paragraphs 139-158, wherein the immunogen is a bacterial subunit.

172. The composition of paragraph 171, wherein the bacterial subunit is derived from *Neisseria meningitides* type C, *Haemophilus influenzae* type B, *Streptococcus pneumoniae*, or Group B *streptococcus*.

173. The composition of paragraph 171, wherein the bacterial subunit is a polysaccharide.

174. The composition of any of paragraphs 139-158, wherein the immunogen is a viral subunit.

175. The composition of paragraph 174, wherein the viral subunit is derived from Hepatitis B virus or Human Papillomavirus.

176. The composition of any of paragraphs 139-158, wherein the immunogen is recombinant.

177. The composition of any of paragraphs 139-158, wherein the immunogen is a vaccine product selected from the group consisting of Anthrax vaccine (BioThrax); BCG (*Bacillus* Calmette-Guérin) (Tice, Mycobax); DTaP (Daptacel); DTaP (Infanrix); DTaP (Tripedia); DTaP/Hib (TriHIBit); DTaP-IPV (Kinrix); DTaP-HepB-IPV (Pediarix); DtaP-IPV/Hib (Pentacel); DT (diphtheria vaccine plus tetanus vaccine) (Sanofi); Hib vaccine (ACTHib); DT (Massachusetts); Hib (PedvaxHib); Hib/Hep B (Comvax); Hep A (Havrix), Hepatitis A vaccine; Hep A (Vaqta), Hepatitis A vaccine; Hep B (Engerix-B), Hepatitis B vaccine; Hep B (Recombivax), Hepatitis B vaccine; HepA/HepB vaccine (Twinrix); Human Papillomavirus (HPV) (Gardasil); Influenza vaccine (Afluria); Influenza vaccine (Fluarix); Influenza vaccine (Flulaval); Influenza vaccine (Fluvirin); Influenza vaccine (Fluzone); Influenza vaccine (FluMist); IPV (lpol), Polio vaccine; Japanese encephalitis vaccine (JE-Vax); Japanese encephalitis vaccine (Ixiaro); Meningococcal vaccine (Menactra); MMR vaccine (MMR-II); MMRV vaccine (ProQuad); Pneumococcal vaccine (Pneumovax); Pneumococcal vaccine (Prevnar); Poliovirus inactivated (Poliovax), Polio vaccine; Rabies vaccine (Imovax); Rabies vaccine (RabAvert); Rotavirus vaccine (RotaTeq); Rotavirus vaccine (Rotarix); Td vaccine (Decavac); Td vaccine (Massachusetts); Tdap vaccine (Adacel); Tdap vaccine (Boostrix); Typhoid (inactivated-Typhim Vi), Typhus vaccine; Typhoid (oral-Ty21a), Typhus vaccine; Vaccinia (ACAM2000); *Varicella* vaccine (Varivax); Yellow fever vaccine (YF-Vax); Zoster vaccine (Zostavax); and any combinations thereof.

178. The composition of any of paragraphs 139-177, wherein the ratio of the silk fibroin matrix to the immunogen is about 1:1000 to about 1000:1.

179. A method for preparing a storage-stable immunogenic composition of any of paragraphs 139 to 178, the method comprising the steps of:
  a. providing a silk fibroin solution comprising at least one immunogen; and
  b. drying the silk fibroin solution of step (a) to form a solid-state silk fibroin, thereby obtaining an immunogenic composition in which the at least one immunogen retains at least about 30% of its original immunogenicity upon storage.

180. The method of paragraph 179, wherein the drying is lyophilization.

181. The method of paragraph 179, wherein the drying is air-dry.

182. The method of any of paragraphs 179-181, further comprising lyophilizing the solid-state silk fibroin from step (b).

183. The method of any of paragraphs 179-182, further comprising post-treatment of the composition.

184. The method of paragraph 183, wherein the post-treatment alters the crystallinity of the composition.

185. The method of paragraph 183 or 184, wherein the post-treatment is contacting the composition with methanol or ethanol.

186. The method of any of paragraphs 183-185, wherein the post-treatment is subjecting the composition to shear stress.

187. The method of any of paragraphs 183-186, wherein the post-treatment is subjecting the composition to an electric field.

188. The method of any of paragraphs 183-187, wherein the post-treatment is subjecting the composition to pressure.

189. The method of any of paragraphs 183-188, wherein the post-treatment is contacting the composition with salt.

190. The method of any of paragraphs 179-189, further comprising reducing the solid-state silk fibroin of step (b) by a mechanical means to obtain micronized particles.

191. The method of paragraph 190, wherein the mechanical means is selected from micronizing, pulverizing, crushing, grinding, freeze-drying or any combination thereof.

192. The method of paragraph 190 or 191, wherein the micronized particles have a size of about 10 nm to about 1000 μm.

193. The method of any of paragraphs 179-192, wherein the at least one immunogen retains at least about 80% of its original immunogenicity upon storage.

194. The method of any of paragraphs 179-193, wherein the storage is over a period of at least 6 months.

195. The method of any of paragraphs 179-194, wherein the storage is at a temperature of about room temperature to about 37° C.

196. The method of any of paragraphs 179-195, wherein the storage is at a temperature greater than 37° C.

197. An immunogenic composition comprising a silk fibroin matrix and at least one live, attenuated virus distributed therein; wherein the live, attenuated virus retains at least about 30% of its original infectivity when the composition is (a) subjected to at least one freeze-thaw cycle, or (b) maintained for at least 24 hours at a temperature above 0° C.

198. The composition of paragraph 197, wherein the virus retains at least about 50% of its original infective stability.

199. The composition of paragraph 197 or 198, wherein the virus retains at least about 80% of its original infective stability.

200. The composition of any of paragraphs 197-199, wherein the composition is maintained for at least about 6 months.

201. The composition of any of paragraphs 197-200, wherein the composition is maintained at a temperature of about room temperature to about 37° C.

202. The composition of any of paragraphs 197-201, wherein the composition is maintained at a temperature greater than 37° C.

203. The composition of any of paragraphs 197-202, wherein the composition is lyophilized.

204. The composition of any of paragraphs 197-203, wherein the live, attenuated virus is an enveloped virus.

205. The composition of paragraph 204, wherein the enveloped virus is selected from the group consisting of Paramyxoviridae, Togaviridae, Orthomyxoviridae, Flaviviridae, Retroviridae, Herpesviridae, Rhabdovirus, and any combinations thereof.

206. The composition of paragraph 204 or 205, wherein the enveloped virus is varicella, measles virus, mumps virus, German measles virus, respiratory syncytial virus, yellow fever virus, or influenza virus.

207. The composition of any of paragraphs 197-203, wherein the live, attenuated virus is a non-enveloped virus.

208. The composition of paragraph 207, wherein said non-enveloped virus is rotavirus.

209. The composition of any of paragraphs 197-208, further comprising an additive.

210. The composition of paragraph 209, wherein the additive is selected from the group consisting of a stabilizing agent, a pharmaceutically acceptable carrier, and any combinations thereof.

211. The composition of paragraph 210, wherein the stabilizing agent is selected from the group consisting of a saccharide, a sugar alcohol, an ion, a surfactant, and any combinations thereof.

212. The composition of paragraph 211, wherein said saccharide is sucrose.

213. A cell-free, stabilized virus preparation comprising a silk fibroin matrix and infective virus distributed therein, wherein the virus retains at least about 30% of its original infectivity when the preparation is (a) subjected to at least one freeze-thaw cycle, or (b) maintained for at least about 24 hours at a temperature above 0° C., or (c) both (a) and (b).

214. The preparation of paragraph 213, wherein the virus and silk fibroin matrix are lyophilized.

215. The preparation of paragraph 213 or 214, wherein the virus retains at least about 80% of its original infectivity.

216. The preparation of any of paragraphs 213-215, wherein the preparation is maintained for at least about 6 months.

217. The preparation of any of paragraphs 213-216, wherein the preparation is maintained at a temperature of about room temperature to about 37° C.

218. The preparation of any of paragraphs 213-217, wherein the preparation is maintained at a temperature greater than 37° C.
219. The preparation of any of paragraphs 213-218, wherein the virus is an enveloped virus.
220. The preparation of any of paragraphs 213-218, wherein the virus is respiratory syncytial virus.
221. The preparation of any of paragraphs 213-218, wherein the virus is a non-enveloped virus.
222. The preparation of any of paragraphs 213-218, wherein the virus is a bacteriophage.
223. The preparation of any of paragraphs 213-218, wherein the virus is a recombinant virus.
224. The preparation of any of paragraphs 213-218, wherein the virus is a viral vector.
225. The preparation of paragraph 224, wherein the viral vector is selected from the group consisting of a retroviral vector, a lentiviral vector, an adenoviral vector, an adeno-associated viral vector, and any combinations thereof.
226. A preparation comprising at least one composition of any of paragraphs 41-80, 139-178, or 197-212.
227. The preparation of paragraph 226, wherein the preparation is selected from a group consisting of a tablet, a lozenge, a suspension, a free-flowing powder, an aerosol, a capsule, and any combinations thereof.
228. The preparation of any of paragraphs 226-227, further comprising a pharmaceutically acceptable carrier.
229. A package comprising at least one composition of any of paragraphs 41-80, 139-178, or 197-212, or a preparation of any of paragraphs 213-225 or 226-228.
230. The package of paragraph 229, wherein the container is selected from a group consisting of a vial, an ampule, a capsule, a tube, a syringe, a bottle, a packet, and any combinations thereof.
231. The package of paragraph 230, wherein the syringe is needleless.
232. A kit comprising the package of any of paragraphs 229-231, and a pharmaceutically acceptable solution.
233. The kit of paragraph 232, further comprising at least one syringe.
234. The kit of paragraph 232 or 233, further comprising a disinfectant.
235. A delivery device comprising: at least one chamber with an outlet, wherein the at least one chamber comprises a pre-determined amount of the composition of any of paragraphs 41-80, 139-178 or 197-212, and the outlet provides an exit for the composition.
236. The device of paragraph 235, wherein the delivery device is selected from the group consisting of a syringe, a dry powder injector, a nasal spray, a nebulizer, an implant, and any combinations thereof.
237. The device of paragraph 235, wherein the implant is a microchip.
238. The device of any of paragraphs 235-237, further comprising an actuator to control release of the composition through the outlet.

To the extent not already indicated, it will be understood by those of ordinary skill in the art that any one of the various embodiments herein described and illustrated may be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Example 1. Stability of MMR Vaccine in Silk Fibroin

Figure 8A:
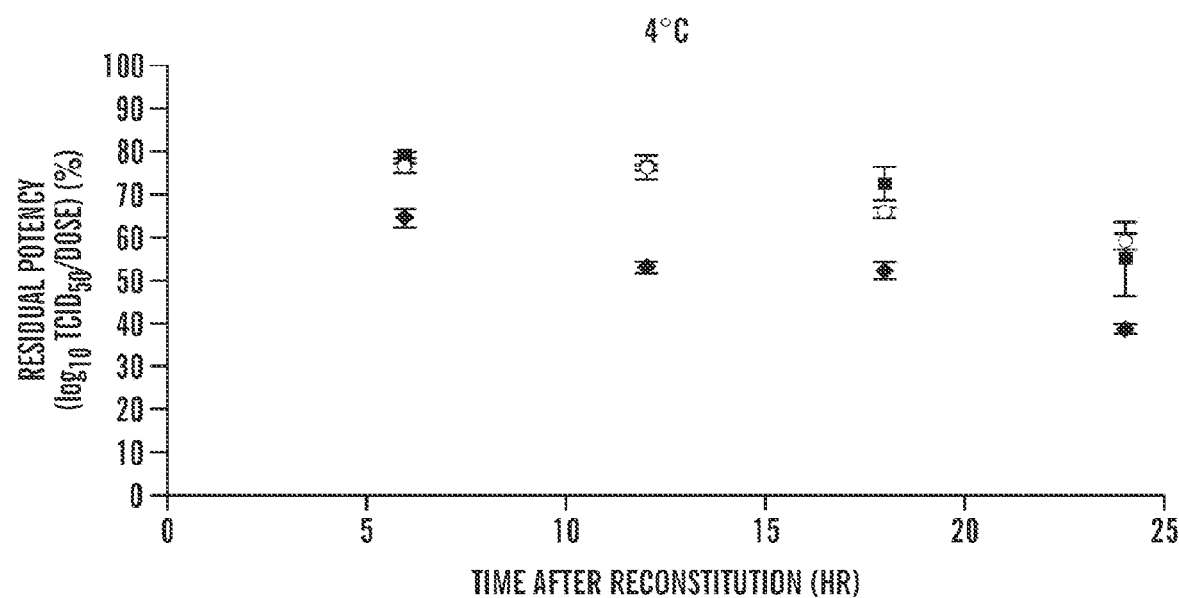
Figure 8B:
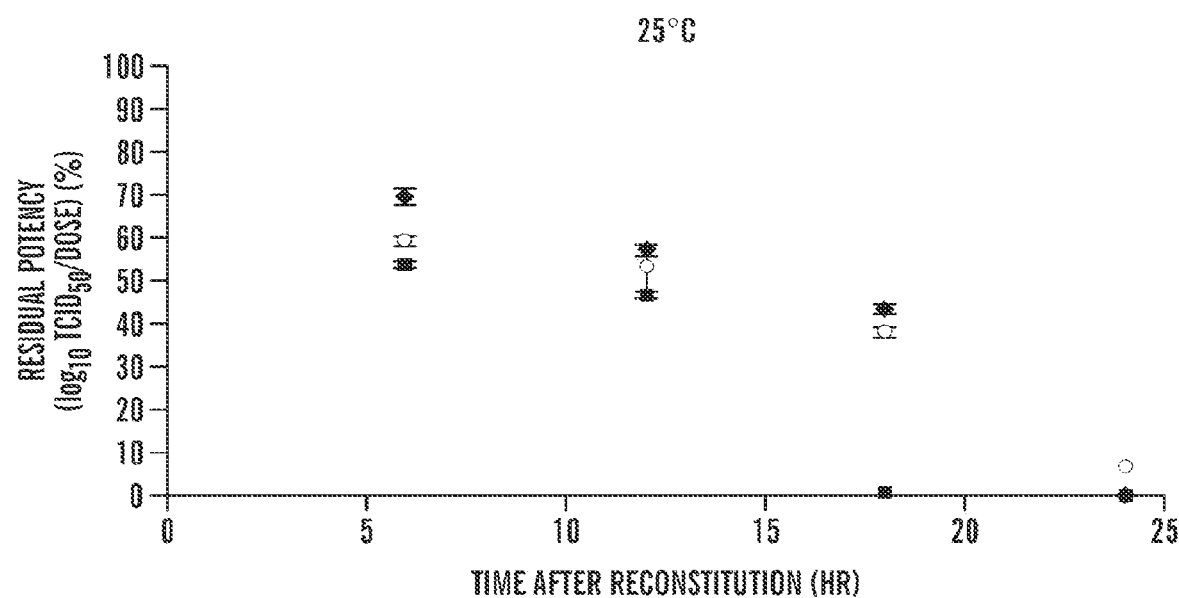
Figure 8C:
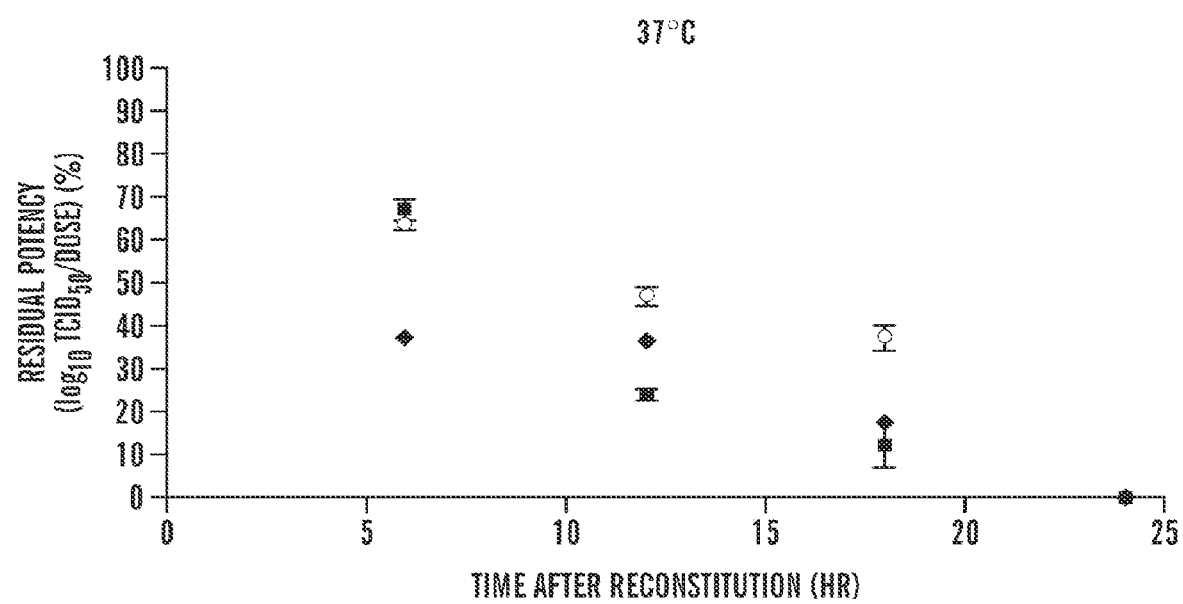
Figure 9A:
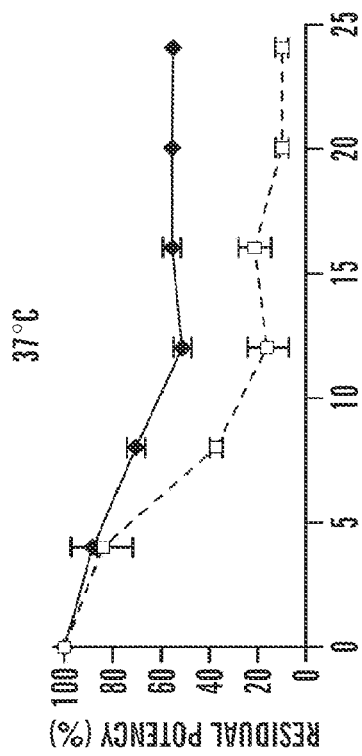
Figure 9B:
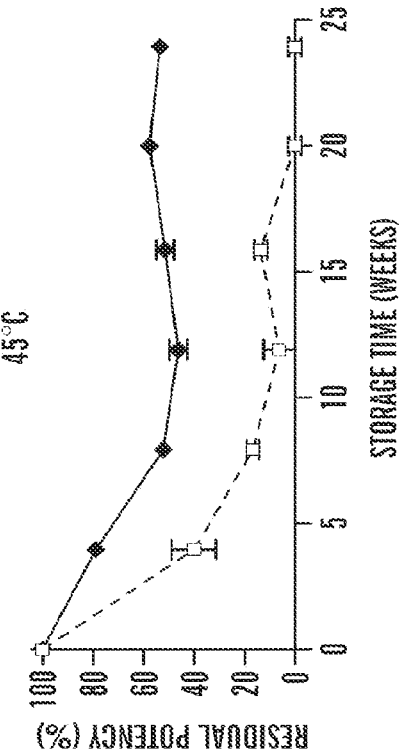
Figure 9C:
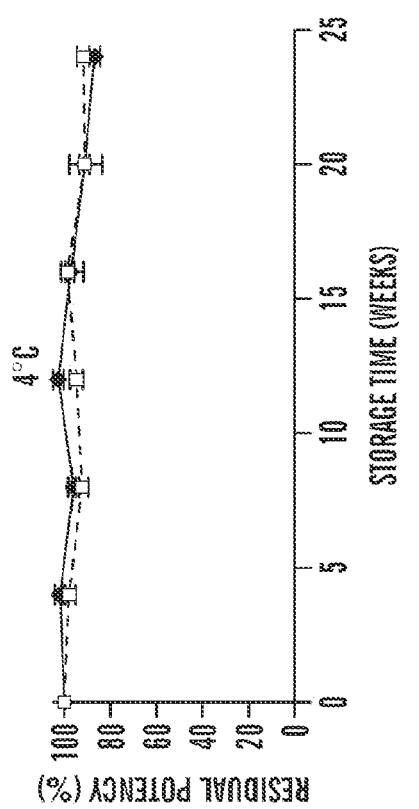
Figure 9D:
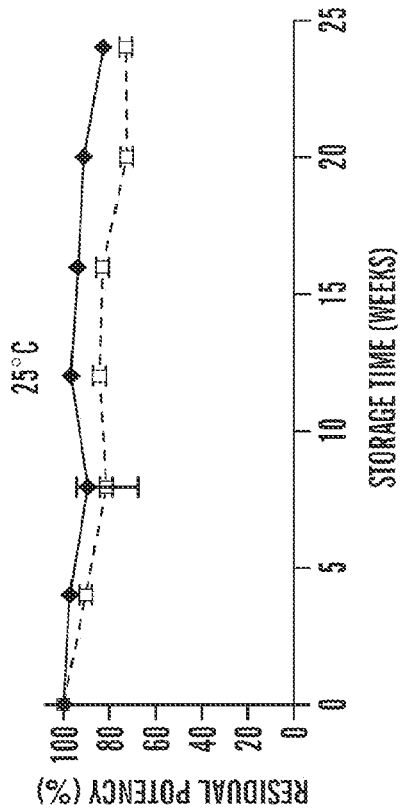
Figure 10A:
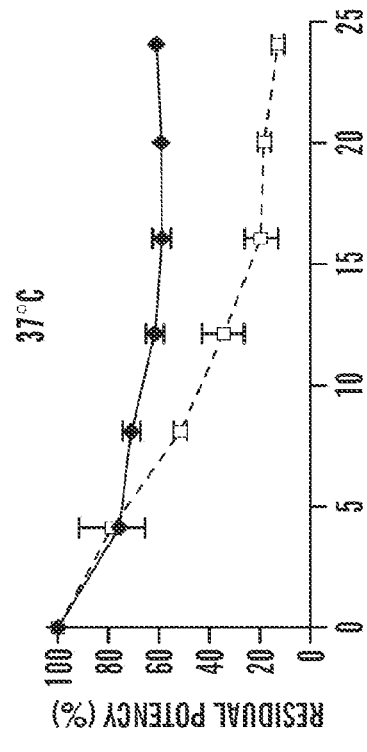
Figure 10C:
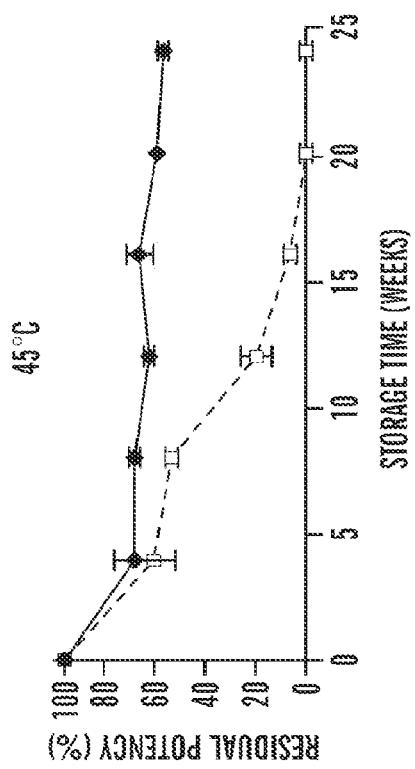
Figure 10B:
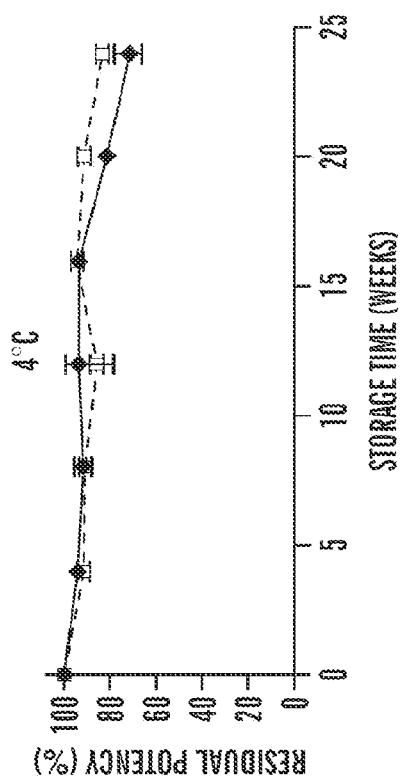
Figure 10D:
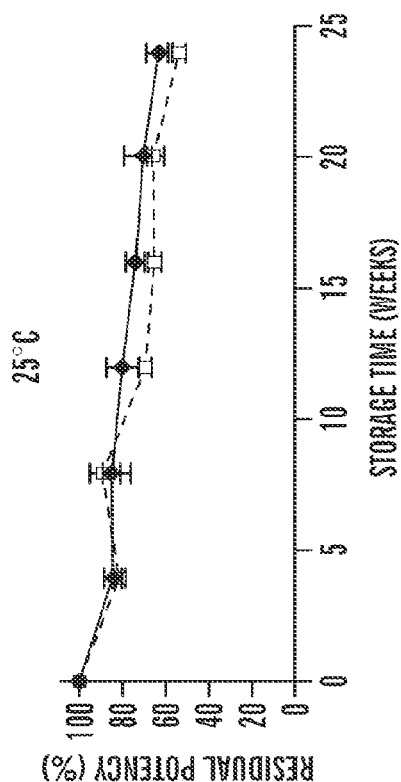
Figure 11A:
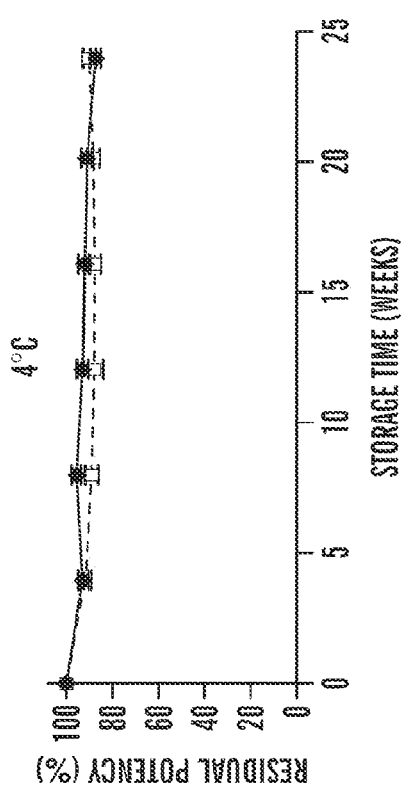
Figure 11B:
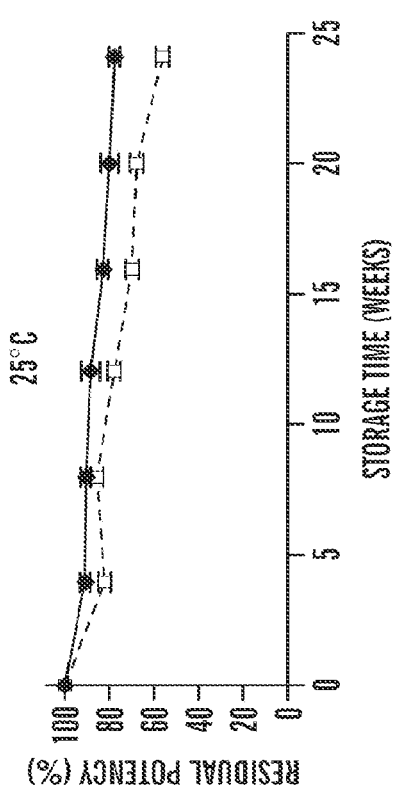
Figure 11C:
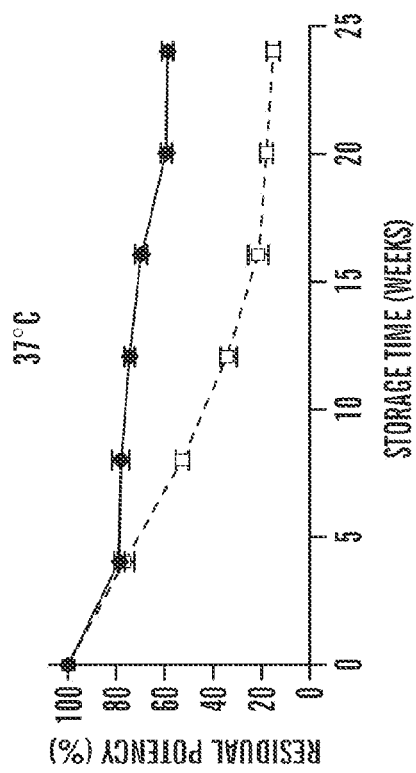
Figure 11D:
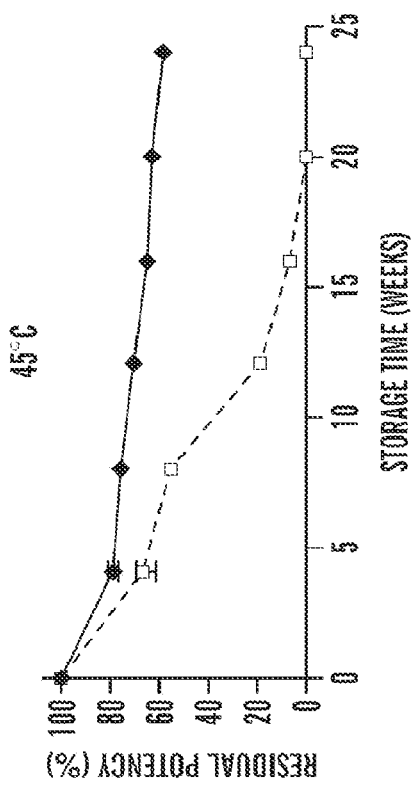
Figure 12A:
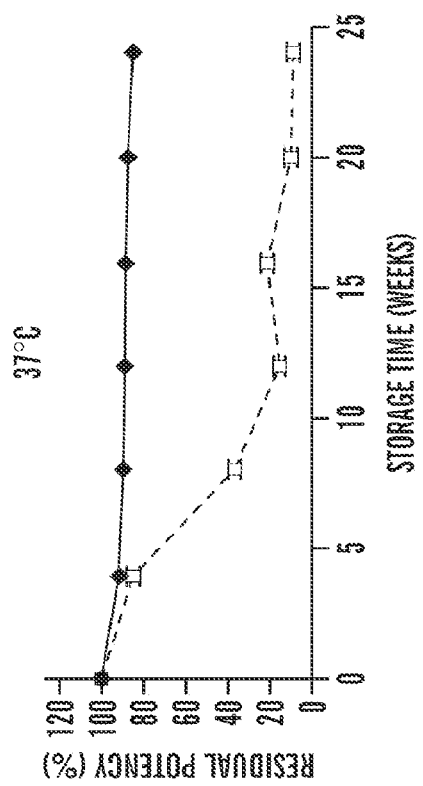
Figure 12B:
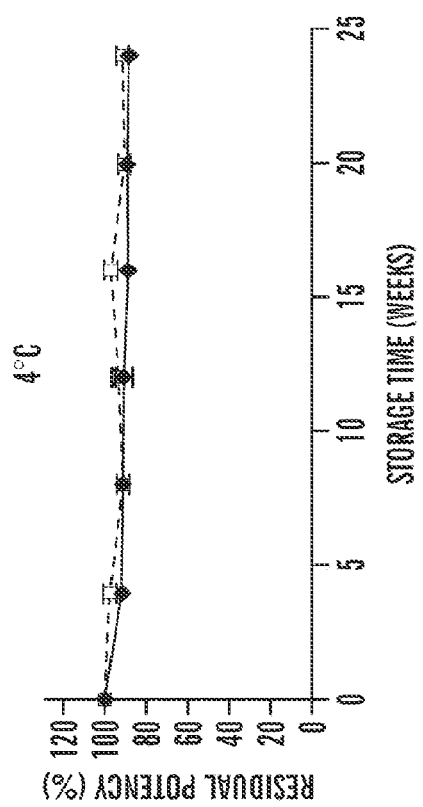
Figure 12C:
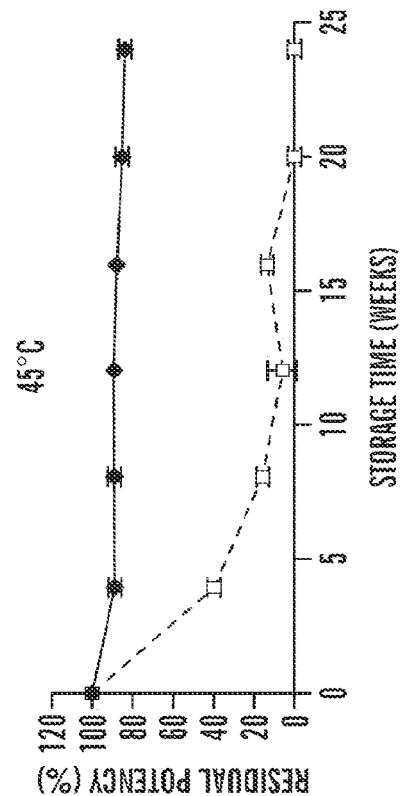
Figure 12D:
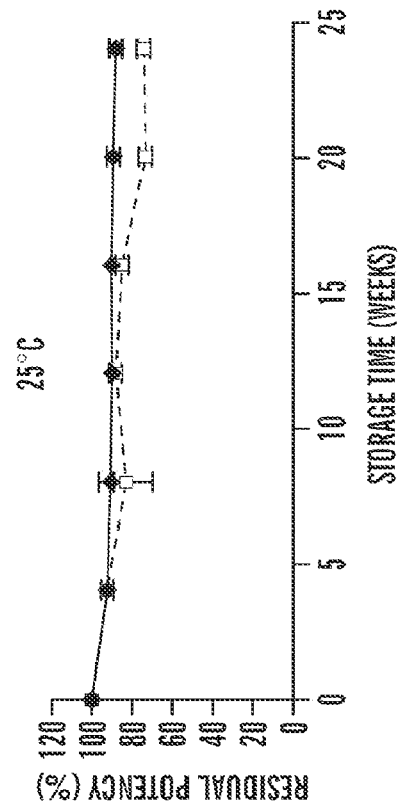
Figure 13A:
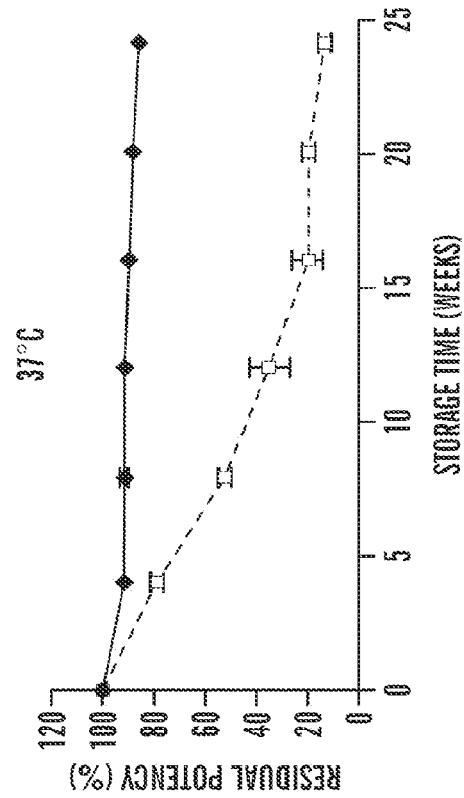
Figure 13B:
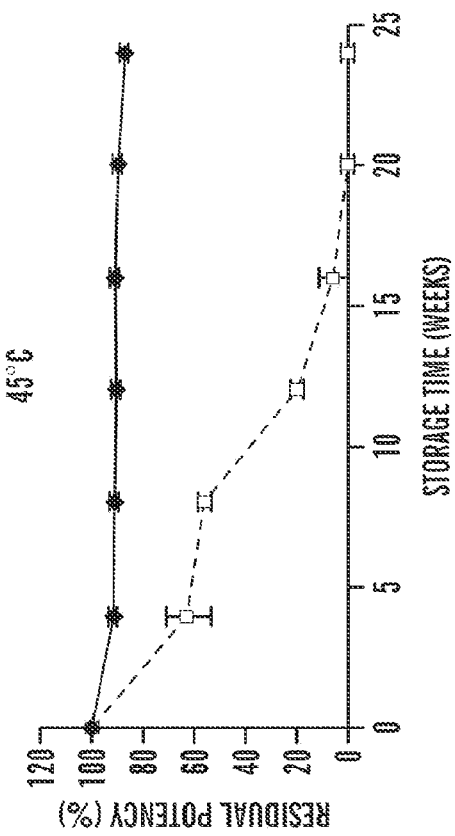
Figure 13C:
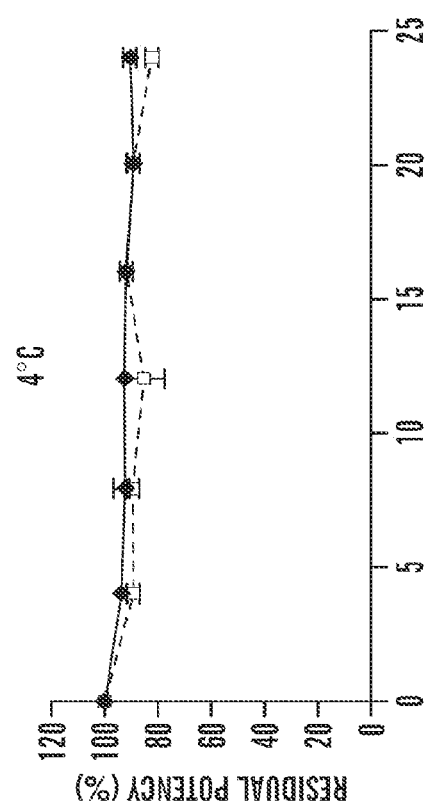
Figure 13D:
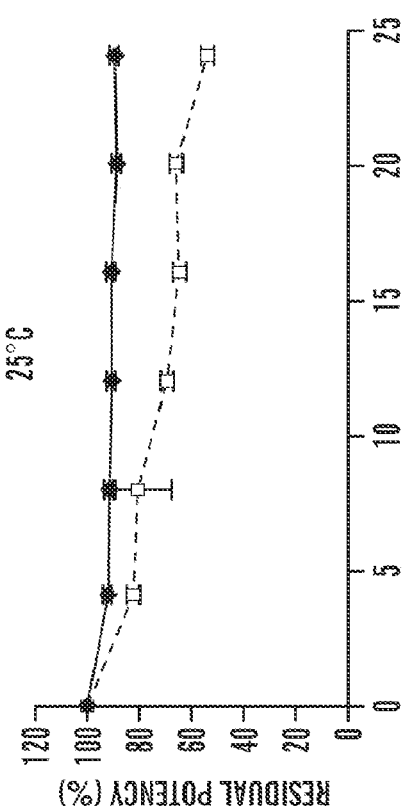
Figure 14A:
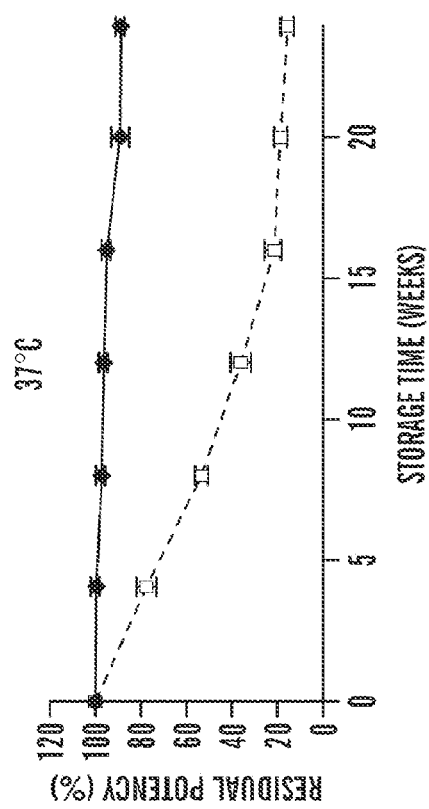
Figure 14B:
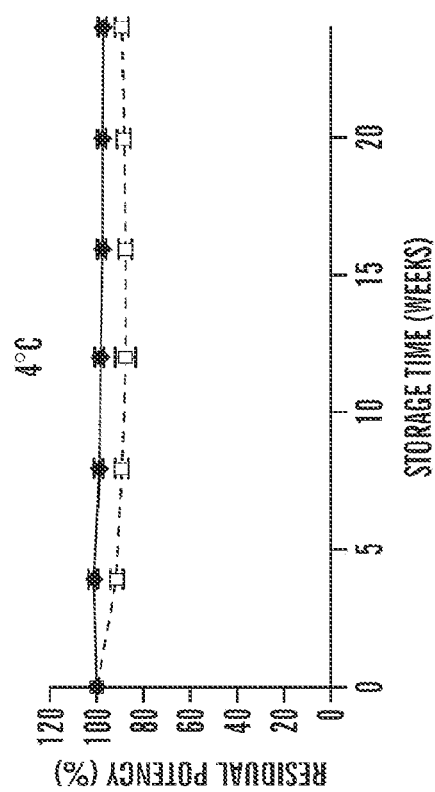
Figure 14C:
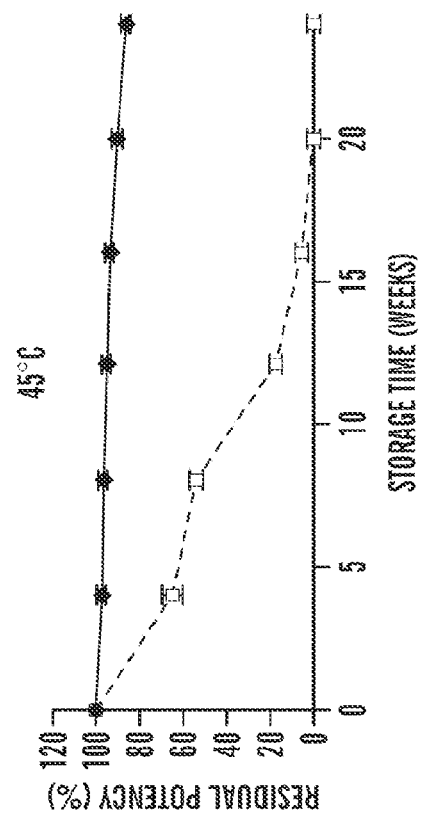
Figure 14D:
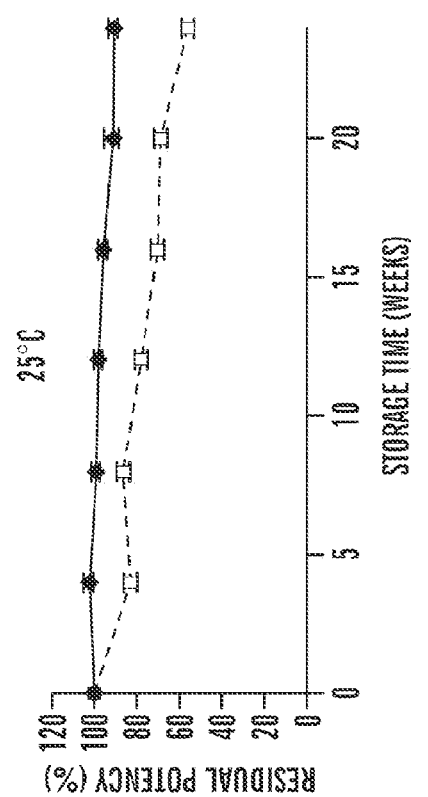
Figure 15A:
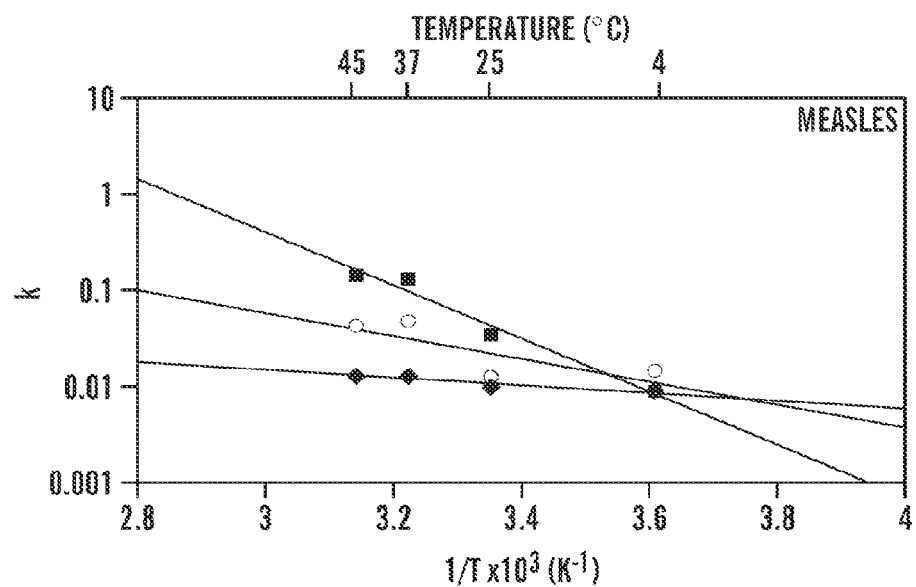
Figure 15B:
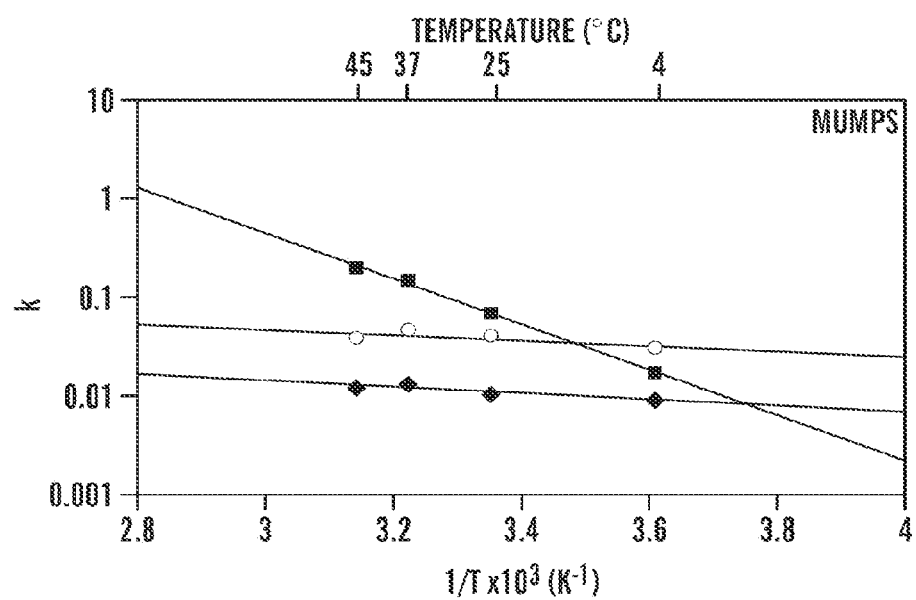
Figure 15C:
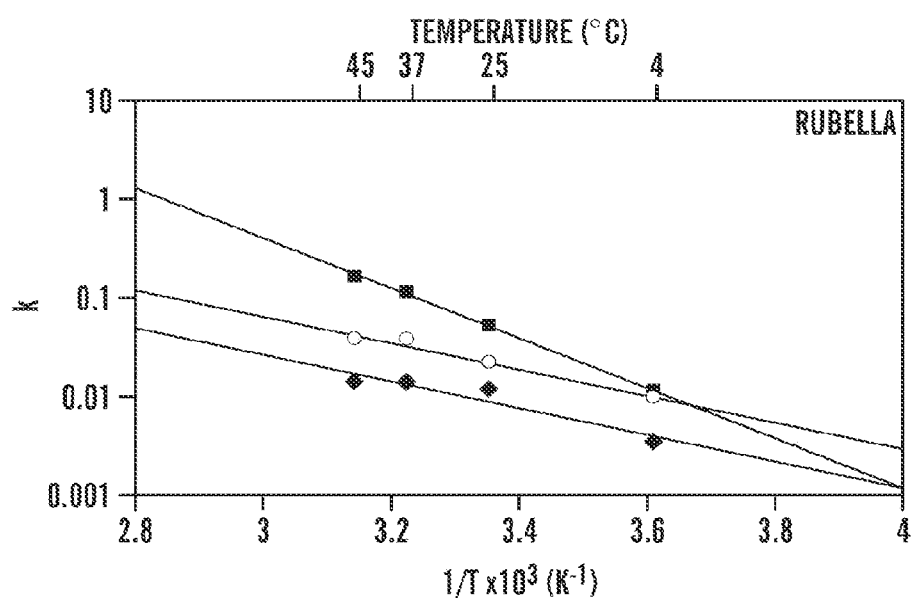

A commercial batch of trivalent vaccine, MMR® II (measles, mumps and rubella virus vaccine live) (Merck & Co., INC., USA) was used. This lyophilized live virus vaccine contains the Enders' attenuated Edmonston measles, the Jeryl Lynn mumps, and the Wistar R A 27/3 rubella viruses. Prior to use, the vaccine is reconstituted in the provided diluent and each 0.5 mL dose contains no less than 1,000 $TC1D_{50}$ (tissue culture infectious doses) of measles virus; 12,500 $TCID_{50}$ of mumps virus; and 1,000 $TCID_{50}$ of rubella virus. Manufacture conditions state that the vaccine must be used within 8 hours of reconstitution and stored at 4° C. or otherwise be discarded. Each dose of the vaccine is calculated to contain sorbitol (14.5 mg), sodium phosphate, sucrose (1.9 mg), sodium chloride, hydrolyzed gelatin (14.5 mg), recombinant human albumin (≤0.3 mg), fetal bovine serum (<1 ppm), other buffer and media ingredients and approximately 25 mcg of neomycin. The product contains no preservative. Before reconstitution, the lyophilized vaccine is a light yellow compact crystalline plug.

A mixture of sterilized 9% (w/v) silk solution and reconstituted MMR vaccine was prepared at a concentration of 1:1 by weight ratio of MMR to silk solution. Films were then cast onto a Teflon-coated surface. The films were allowed to dry in a sterile hood for 24 hr at room temperature (RT). A sample of reconstituted vaccine in solution for 24 hr was also prepared for comparison.

A standard curve was generated by reconstituting the vaccine, considered as the 1 $\log_{10}$ dilution, and the vaccine solution was then serially diluted in 0.5 $\log_{10}$ steps from 1.5 $\log_{10}$ to 3.5 $\log_{10}$. The silk films were redissolved in an aliquot of water that diluted the final concentration of vaccine in the solution to 1.5 $\log_{10}$. Vero cells (African green monkey kidney cells; ATCC, Manassas, VA) were grown to confluence, trypsinized, counted, and adjusted to 50,000 cells/mL and plated in a 24-well plate. Next, 50 μL of the vaccine dilution, redissolved silk film, and 24 hr-stored reconstituted vaccine were added to a well of Vero cells, in triplicate. The virus was allowed to replicate in the cell for 3 days, then the RNA from the infected cells isolated, converted to cDNA and quantitated using qPCR. A log-linear relationship exists between the amount of target RNA and the PCR cycle where the fluorescence raises above the background (threshold cycle, Ct). The more viable the viruses that are present in the sample, the lower the Ct value.

The results of the qPCR infectivity assay show a linear relationship between the increase of vaccine dilution and the greater the Ct value (FIG. 1). The assay produced expected results as the low vaccine dilution contained a greater quantity of viable viruses, therefore producing a lower Ct value. Using this result as a standard curve, the results for the silk-encapsulated vaccine sample and the reconstituted vaccine sample can be quantified by extrapolating the final $\log_{10}$ dilution from their Ct values.

The $\log_{10}$ dilution values were then converted into potency values of $\log_{10}$ $TCID_{50}$/dose. The $\log_{10}$ $TCID_{50}$/dose values of the MMR-silk films were then related to the $\log_{10}$ $TCID_{50}$/dose of the original dilution at which they were casted (1.5 log$_{10}$ dilution), producing the residual potency. The reconstituted control vaccine stored at RT for 24 hours produced no Ct values, indicating that it had lost nearly, if not all, its potency. The initial potencies recovered from the MMR-silk films for measles, mumps and rubella were 75.89%, 58.04% and 62.48%, respectively (Table 1).

TABLE 1

Initial potency recovery of 1:1 (w/w) MMR-silk films

| | Initial Potency Recovery (log10 TCID50/dose) (%) |
|---|---|
| Measles | 75.89 |
| Mumps | 58.04 |
| Rubella | 62.48 |

This is a substantial improvement over the reconstituted control vaccine stored at room temperature for the same period of time, for which residual potency was below the lower limit of detection. The initial loss of potency in the silk-embedded vaccine was likely caused by reconstituting the lyophilized vaccine during the preparation of the films rather than the effect of interactions of the vaccine with the silk. To show that the loss of activity most likely occurred while the MMR-silk was still in solution before completely drying into films, aliquots of lyophilized vaccine were reconstituted in water for 24, 18, 12, and 6 hr at room temperature prior to cell inoculation (FIG. 2).

As seen in FIG. 2, the vaccine potency decreases significantly the longer it remains in solution. Vaccine samples in solution for 24 hr prior to cell inoculation exhibited no residual potency for any of the viral components. Once the films were dried and stored, the silk exhibited a stabilizing effect on the vaccine. As seen in FIG. 3, after 3 months of storage at room temperature, the silk films retained 96%, 92% and 80% potency for the measles, mumps and rubella virus, respectively. The results indicate that MMR vaccines stored in only unprocessed silk films are capable of extending the potency of the commercially prepared lyophilized vaccine at RT.

Example 2. Addition of Additives

Whether the addition of stabilizing additives further increases the thermostability of the virus was examined. Oral polio virus vaccine (OPV), also a live attenuated vaccine, has been widely studied and was commercially prepared with the addition of $MgCl_2$ stabilizer. Studies on the effects of stabilizing additives OPV have been conducted and previously tested stabilizers include sucrose, magnesium sulfate and magnesium chloride (Mirchamsy et al., 1978; Rapp et al., 1965). MMR-silk films were then prepared from solutions of MMR, silk, and stabilizer. The initial recovery of MMR-films stabilized with 1M $MgCl_2$, 1M $MgSO_4$ and 70% sucrose is shown in FIG. 4. Although $MgCl_2$ is an excellent stabilizer for OPV, it had negatively stabilizing effects on measles, mumps, and rubella. $MgSO_4$ provided the best stabilization of the measles component of the vaccine but little effect on mumps and had negative effects on rubella. Sucrose, however, acted as a stabilizer for all three components of the MMR vaccine. Furthermore, the initial recovery of the viral components stabilized in sucrose shows an improvement over the initial recovery of MMR-silk only films (Table 1). Also, reconstitution of the vaccine in 70% sucrose solution in RT (FIG. 5) showed higher retained viral potency over 24 hr than the vaccine reconstituted in water at RT (FIG. 2). Compared to MMR vaccine reconstituted in water, vaccine reconstituted in 70% sucrose also provided better stability at 4° C. and 37° C. (FIG. 6). Using stabilizing additives such as sucrose may minimize the initial loss of vaccine activity during the film preparation. The sucrose can stabilize the vaccine during the film drying process while the MMR and silk are still in solution.

Example 3. Long Term Stabilization of Measles, Mumps and Rubella Vaccine

We show that vaccine-entrapped in silk films and lyophilized silk films are significantly extended in terms of half-life at storage temperatures as high as 45° C. In the presence of silk the degradation rate of viral proteins is reduced. Biophysical characterization has demonstrated that the silk provides structural stability to the vaccine by reducing residual moisture during storage and increasing the melting point of the viral proteins. Thus, we present a vaccine stabilizing system capable of extending vaccine potency without the need for refrigeration. The silk can be molded into a variety of delivery systems including films, hydrogels, microspheres and microneedles, capable of being tailored for specific stabilization and delivery needs. This material system has may be used ex vivo or in vivo as delivery vehicles due to the biocompatibility and FDA-approved history of silk use in biomedical devices.

Residual Vaccine Activity after Immobilization in Silk Films

The silk films were prepared with a weight ratio of vaccine to silk of 1:1. Initial recovered vaccine potency was determined directly after the films were prepared to determine how much vaccine infectivity was lost during the film fabrication process. In order to incorporate the vaccine into the silk solution, the lyophilized vaccine must be reconstituted. The lyophilized vaccine was reconstituted immediately prior to cell inoculation. Once the freeze-dried vaccine has been reconstituted, potency decreases rapidly (Galazka, 1998; WHO 2006) and according the manufacturer's specifications, the MMR vaccine must be used within 8 hours of reconstitution or otherwise discarded. Once completely dried, the films, containing the same amount of lyophilized vaccine, were dissolved in sterile water and the solution was added to the Vero cells for potency testing. The potency results of the silk films were compared to the potency of the lyophilized vaccine to establish an initial recovered potency. The initial residual potency observed from the MMR-silk films are summarized in Table 2 with 84.7%, 73.9%, and 87.0% residual potency of the measles, mumps, and rubella components, respectively.

TABLE 2

Comparison of the Initial recovered viral potency of vaccine-entrapped silk films and lyophilized silk films

| Vaccine-silk form | Viral Component | Initial Recovered Potency (%) |
|---|---|---|
| MMR-silk film | Measles | 84.7 ± 6.40 |
| | Mumps | 73.9 ± 2.24 |
| | Rubella | 87.0 ± 2.23 |
| Lyophilized MMR-silk film | Measles | 94.7 ± 0.34 |
| | Mumps | 89.6 ± 1.30 |
| | Rubella | 98.4 ± 0.35 |

Enough vaccine entrapped silk films were fabricated with this method of air-drying and stored for a 6 month study to assess long-term stability at four different temperatures (4° C., 25° C., 37° C. and 45° C.). However, we hypothesized that the majority of the loss of viral potency observed with the films occurred while the MMR-silk was in solution for the preparation process. To verify this hypothesis, lyophilized vaccine was reconstituted in the diluents provided by the manufacturer and the solutions were stored at 4° C., 25° C. and 37° C. (FIG. 8A-8C). Potency measurements were taken after 6 hours, 12 hours, 18 hours and 24 hours after reconstitution. As predicted, the vaccine rapidly lost potency within hours in solution and storage in higher temperatures resulted in a more rapid decline in potency. Compared to the drying time of the films, at 12 hours in solution at 4° C. 53.4%, 73.4%, 76.3% residual potency remains for the measles, mumps and rubella components, respectively. At 12 hours at 25° C., only 57.8%, 53.1%, 46.6% residual potency of the measles, mumps, rubella remained, respectively. A more dramatic decline was observed for vaccine reconstituted for 12 hours at 37° C. as only 36.5%, 46.6%, and 23.9% of the measles, mumps and rubella potency was recovered, respectively. Based on these results, we postulated that reducing the time that the initial vaccine was in solution would improve recovery. Therefore, lyophilized MMR-silk films were prepared to shorten the MMR-silk solution stage. The lyophilization process significantly improved the long-term thermal stability of the vaccine in the silk films. As shown in Table 2, compared to the initial potency recovered from the air-dried silk films, the lyophilized films improved the recovery of measles, mumps, and rubella to 94.7%, 89.6%, 98.4%, respectively Thermostability of Vaccine-Encapsulated Silk Films Vaccine stability was quantitatively expressed as the residual potency observed from the films after storage. Residual potency was measured and compared with the initial residual potency (Table 2) to demonstrate vaccine stability. Measuring the residual potency of all the viral components of the vaccine stored in silk films over six months, with the exception of storage at 4° C., the general trend showed that the silk films enhanced stabilization of the measles, mumps, and rubella viral particles by displaying higher residual potencies when compared to the manufacturer's lyophilized vaccine stored at the same temperature. FIGS. 9A-9D show the comparison of residual potency of the measles component of the vaccine for silk films and lyophilized MMR vaccine powder stored for six months at 4° C., 25° C., 37° C. and 45° C. With the exception of storage at 4° C., the silk films showed greater residual potency of the vaccine. Even at 4° C., the residual potency of the silk films was similar that of the MMR powder. While the residual potency of the powder did not fluctuate, the silk films displayed greater variance in measured potency at this temperature. For the first 3 months the silk films outperformed the powder with greater recovered residual potency. In the last 3 months the silk films displayed a slight decrease in residual potency while that of the powder remained relatively constant. At the end of the six month study, the residual potency of the measles component of the MMR vaccine stored in silk films was 87.2% compared to 92.2% for the powder. The silk films, however, show improved measles residual potency when stored at 25° C., 37° C. and 45° C. Stored at 25° C., the silk films showed greater recovered potency at each time point and at the end of the six months displayed 83.9% recovered potency compared to 74.5% for the powder.

The stabilization provided by the silk was even more evident for films and powder stored at elevated temperatures, 37° C. and 45° C. At 37° C., the silk films showed a dramatic improvement in stability of the measles infectivity through the course of six months, resulting in 56.5% potency recovered compared to 9.9% from the powder. In the case of films and powder stored at 45° C., the measles component of the vaccine lost all potency after 20 weeks in storage while the silk films retained 53.5% activity after 24 weeks. Similar trends were shown for both the mumps (FIG. 10A-10D) and rubella components (FIG. 11A-11D). Again, similar to the results for the measles component, the silk films displayed more stabilization of the mumps component at 37° C. and 45° C. At both temperatures the silk films displayed a slight drop in residual activity during the first month in storage, but beyond the first month the decrease in residual potency was much slower than the decrease in vaccine activity of the stored powder. At the conclusion of the study, the silk films stored at 37° C. retained 61.3% of the mumps infectivity while the powder retained 13.0%. After 6 months of storage at 45° C., the silk films recovered 59.6% of the mumps potency while the powder lost all potency after 20 weeks. The rubella component displayed similar trends in potency. For silk films stored at 4° C., 25° C., 37° C. and 45° C., 88.4%, 78.4%, 60.3%, and 58.3% residual potency was recovered, respectively. With the exception of powders stored at 4° C., these results showed that the silk provided enhanced stabilization and maintenance of potency over the powder. The residual potency of the powder at 4° C., 25° C., 37° C. and 45° C. was 89.4%, 56.3%, 15.3% and 0%, respectively.

While the lyophilized silk films were initially prepared to improve the initial recovery of vaccine lost during the film fabrication process, they provided even greater stabilization of the vaccines at elevated temperature. The residual potency of the measles, mumps, and rubella components stored in the lyophilized silk films are shown in FIGS. 12A-12D, 13A-13D, and 14A-14D, respectively. Regardless of the storage temperature, the lyophilized films provided comparable levels of stabilization to all components of the vaccine. While the lyophilized silk films showed improved stabilization and residual potency recovered over all the temperatures, the level of stabilization was more dramatic at the higher temperatures. After 6 months of storage, the lyophilized silk films retained 85.2% and 85.1% of the residual measles potency at 37° C. and 45° C., respectively. Similarly, 86.2%, and 86.0% of the mumps potency remained after 6 months when stored at 37° C. and 45° C., respectively. The rubella component appeared to be most stabilized by the lyophilized silk films as 88.2% of the viral potency remained after 6 months storage at 37° C., while storage at 45° C. still resulted in retention of 87.5% of the viral potency.

Evaluation of Thermostability by Kinetics of Degradation

Figure 16A:
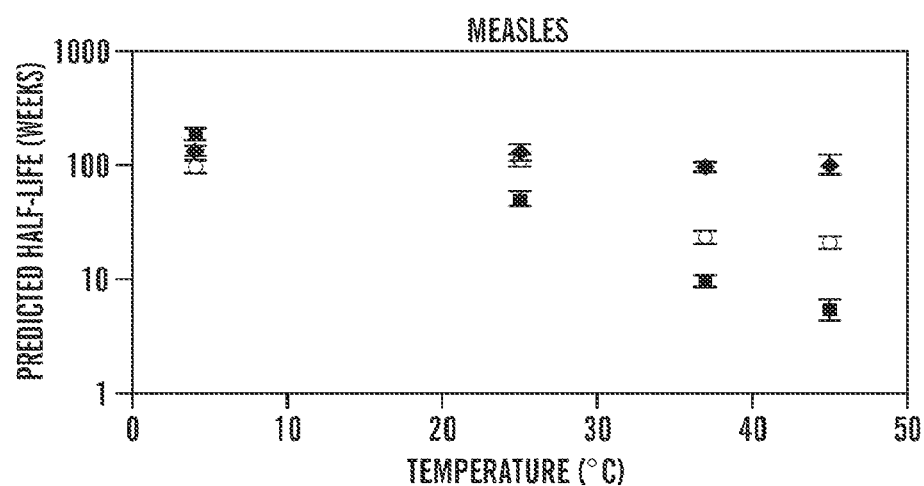
Figure 16B:
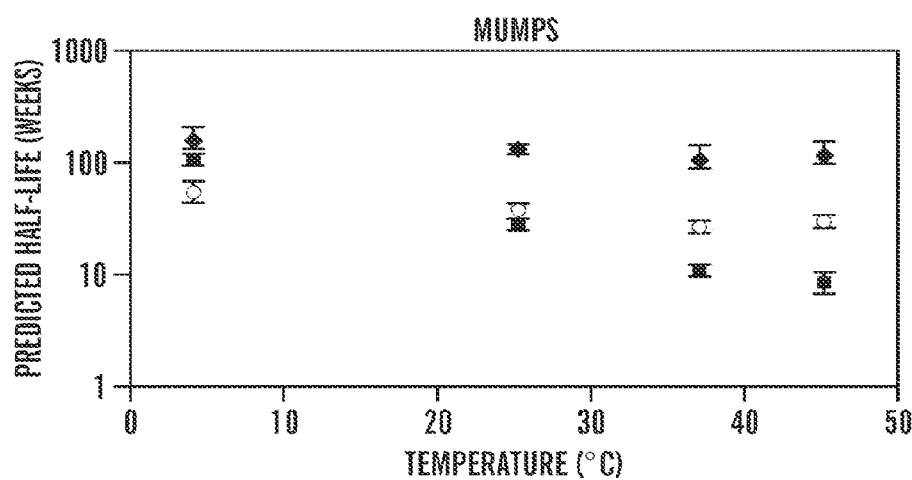
Figure 16C:
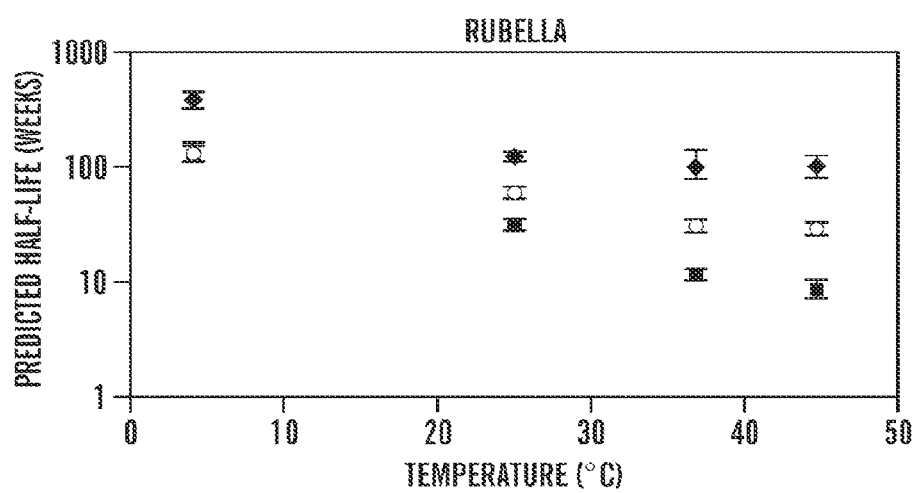

The degradation rate, $k_{obs}$, for each temperature was calculated by linear regression of the $\log_{10}$ drop of virus titer against the exposure time in weeks. The slopes of the resulting curves represent the degradation rates. The virus half-lives ($t_{1/2}$) at each temperature and the corresponding 95% confidence interval were then calculated from the $k_{obs}$ and their standard errors. The virus half-life is the predicted half-life or time required for the average potency to decrease to 50% of the initial value. The estimated degradation rates and corresponding half-lives for each viral component and vaccine encapsulation method are summarized in Table 3 and the half-lives are plotted against temperature in FIG. 16A-16C. The degradation rates of the three systems over the range of temperatures tested also fitted well on the Arrhenius plot (FIG. 14A-15C). As seen from the plot, the values for the slope of the powder vaccine form were consistently higher than both the silk systems, indicating the rates of degradation of the powder increased faster with an increase in storage temperature.

TABLE 3

Summary of degradation rates and predicted half-lives of the vaccine powder, and silk film- and lyophilized silk film-encapsulated vaccines

| Vaccine System | | Degradation rate, $k_{obs}$ (log10 TCID50/weeks) | Predicted Half-life, $t^{1/2}$ (weeks) (Lower, Upper Limit) |
|---|---|---|---|
| Measles Temperature (C.°) | | | |
| 4 | Powder | 0.009 ± 0.0005 | 178.6 weeks (169.2; 197.4) |
|   | Films | 0.0136 ± 0.0025 | 96.6 weeks (81.6, 126.6) |
|   | Lyophilized Films | 0.009 ± 0.0001 | 135.3 weeks (133.8, 138.3) |
| 25 | Powder | 0.0331 ± 0.0037 | 47.1 weeks (42.4, 56.6) |
|   | Films | 0.0123 ± 0.0002 | 100.8 weeks (99.1, 104.0) |
|   | Lyophilized Films | 0.0098 ± 0.0013 | 123.8 weeks (109.8, 151.8) |
| 37 | Powder | 0.1287 ± 0.0004 | 9.4 weeks (9.4, 9.5) |
|   | Films | 0.0458 ± 0.0034 | 21.9 weeks (20.4, 25.0) |
|   | Lyophilized Films | 0.0131 ± 0.0008 | 93.8 weeks (88.4, 104.6) |
| 45 | Powder | 0.139 ± 0.0261 | 5.1 weeks (4.3, 6.7) |
|   | Films | 0.0401 ± 0.0010 | 19.8 weeks (19.4, 20.8) |
|   | Lyophilized Films | 0.0128 ± 0.0019 | 94.9 weeks (82.6, 119.4) |
| Mumps Temperature (C.°) | | | |
| 4 | Powder | 0.0173 ± 0.0005 | 102.3 weeks (99.4, 108.0) |
|   | Films | 0.0302 ± 0.005 | 51.3 weeks (44.0, 65.9) |
|   | Lyophilized Films | 0.0091 ± 0.0018 | 152.1 weeks (127.0, 202.3) |
| 25 | Powder | 0.0677 ± 0.0001 | 26.5 weeks (26.5, 26.6) |
|   | Films | 0.0408 ± 0.0056 | 34.3 weeks (30.2, 42.6) |
|   | Lyophilized Films | 0.0106 ± 0.0005 | 129.3 weeks (123.5, 140.4) |
| 37 | Powder | 0.1435 ± 0.0052 | 10.7 weeks (10.3, 11.5) |
|   | Films | 0.0439 ± 0.001 | 25.7 weeks (25.1, −26.8) |
|   | Lyophilized Films | 0.0129 ± 0.0025 | 106.0 weeks (88.8, 140.4) |
| 45 | Powder | 0.1967 ± 0.0357 | 8.2 weeks (6.9, 10.7) |
|   | Films | 0.0384 ± 0.0021 | 28.6 weeks (27.1, 31.6) |
|   | Lyophilized Films | 0.0121 ± 0.0027 | 111.9 weeks (91.5, 152.7) |
| Rubella Temperature (C.°) | | | |
| 4 | Powder | 0.0119 ± 0.0022 | 124.5 weeks (105.1, 163.3) |
|   | Films | 0.0101 ± 0.0012 | 123.6 weeks (110.5, 149.9) |
|   | Lyophilized Films | 0.0036 ± 0.0001 | 383.7 weeks (373.3, 404.4) |
| 25 | Powder | 0.0521 ± 0.0021 | 29.5 weeks (28.3, 31.8) |
|   | Films | 0.022 ± 0.0024 | 56.8 weeks (51.2, 68.0) |
|   | Lyophilized Films | 0.0121 ± 0.0012 | 117.3 weeks (106.7, 138.5) |
| 37 | Powder | 0.1192 ± 0.0006 | 10.9 weeks (10.8, 11.0) |
|   | Films | 0.0387 ± 0.0004 | 28.9 weeks (28.6, 29.5) |
|   | Lyophilized Films | 0.0144 ± 0.0037 | 99.3 weeks (79.0, 139.8) |
| 45 | Powder | 0.1681 ± 0.0298 | 8.2 weeks (6.9, 10.6) |
|   | Films | 0.0387 ± 0.0003 | 27.3 weeks (27.1, 27.7) |
|   | Lyophilized Films | 0.0144 ± 0.0025 | 97.1 weeks (82.8, 125.9) |

With the exception of samples stored at 4° C., the silk- and lyophilized silk-encapsulated vaccine systems exhibited lower degradation rates over the powder vaccine at 25° C., 37° C. and 45° C. for the measles, mumps and rubella components. The decreased degradation rates correspond to an increase in predicted half-lives. From the Table, the trends appear similar for all the viral components and show that at elevated temperatures, the silk films increased the half-lives of the vaccine over the powder formulation with the lyophilized silk films showing dramatic improvements of vaccine half-lives over both the powder and silk films. Furthermore, as the storage temperature was increased, the degradation rates and predicted half-lives significantly increased and decreased, respectively, for both the powder and silk film formulations. The lyophilized silk film samples, however, maintained slow degradation rates across all the tested storage temperatures. Evaluating the change in rate of degradation of the measles component from 4° C. to 45° C., the powder vaccine exhibited a 1,444% increase in degradation rate from 0.0136±0.0025 to 0.0401±0.0010 $log_{10}$ $TCID_{50}$/weeks, while the MMR-silk film and lyophilized MMR-silk film had a 195% increase from 0.0.139±0.0261 to 0.009±0.0005 $log_{10}TCID_{50}$/weeks and 42% increase from 0.0128±0.0019 to 0.009±0.0001 $log_{10}$ $TCID_{50}$/weeks in degradation rate over the temperature range, respectively. The mumps and rubella components exhibit similar trends. With the exception of storage at 4° C., in the powder vaccine data shows a predicted measles half-life of 178.6 weeks, greater than the 96.6 weeks for the silk films and the 135.3 weeks of the lyophilized silk films, the silk films and lyophilized silk films displayed a much more dramatic increase in half-life of the virus at elevated temperatures. The difference was especially evident in the predicted half-life of the virus at 37° C. and 45° C. At 35° C., the 21.9 weeks half-life of the silk films was a significant improvement of the 9.4 weeks provided by the powder but the lyophilized silk films dramatically increased the half-life to 93.8 weeks. Storage at 45° C. provided similar results as the powder, silk films and lyophilized silk films showed half-lives of 5.1, 19.8, and 94.9 weeks, respectively.

Figure 17:
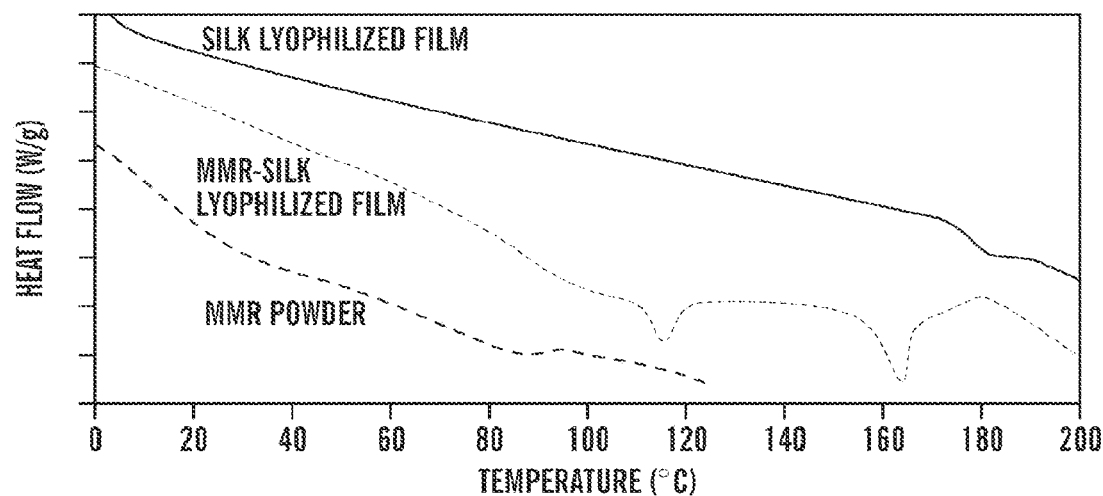

The temperature dependence of the vaccine degradation rates was further evaluated using regression analysis. From plot of drop of virus titer against time (not shown) for the powder, silk film and lyophilized silk film systems, the data can be reasonably approximated by a straight line, exhibiting pseudo zero-order behavior. The plot of virus titer drop against time corresponds to and exhibits similar trends to the residual potency curves. As seen from the plot, a linear response of change in viral concentration suggests that the degradation mechanism follows zero-order kinetics. Though upon closer inspection of the data, the linearity of the drop of virus titer against time decreases at long time intervals. These data suggest that the degradation rate may deviate from zero-order behavior and decrease over longer periods of time. The kinetic model of the degradation of the vaccine over time is therefore considered a pseudo zero-order model. Pseudo reaction orders are encountered in drug stability studies as only the change in concentration of the active pharmaceutical ingredient is usually monitored over time, while other reactants and buffer components are in large excess though not analyzed (Zhou et al., 2009). Hence, a first-order reaction can appear to be a zero-order reaction, or pseudo zero-order. In zero-order reactions, the rate of the reaction does not depend on the concentration of the reactant and is constant. The zero-order rate equation is as follows $$-\frac{dC}{dt} = k_{obs}$$

And the data obtained at each temperature was fitted using the following equation:

$$\frac{C_t}{C_0} = -k_{obs}t$$

where Ct is the measured potency in $\log_{10}$ $TCID_{50}$ at time t, $C_0$ is the measured potency at time zero, $k_{obs}$ is the degradation rate determined by linear regression and tis the time of storage in weeks. The predicted half-life, $t_{1/2}$, is the time required for the average potency to decrease to 50% of the initial value. The half-life for each temperature was estimated by the equation $$t_{1/2} = \frac{C_0}{2k_{obs}}$$

Thermal degradation rates of the three vaccine systems should follow the Arrhenius law expression with respect to absolute temperature as shown in the following equation:

$$k(T)=Ae^{-E1RT}$$

where k is the thermal degradation rate, A is the preexponential factor, E is the activation energy, R is the gas constant and Tis the absolute temperature. A plot of degradation rates against the reciprocal of absolutely temperature can show the temperature-dependent degradation trends over large temperature ranges. The Arrhenius plots show that the powder vaccine has the steepest slope, indicating a greater dependence of degradation on temperature than both of the silk systems. By comparison, the more shallow slopes of the silk systems demonstrate that the silk greatly reduces the degradation rate of the vaccine at elevated temperatures and is capable of maintaining vaccine potency at high ambient temperatures. As seen in the comparison of half-lives of the three vaccine systems, the improved half-lives of the silk systems become more evident and dramatic as the storage temperature increases.

Effect of Processing Conditions on Residual Moisture of Vaccine Systems

The MMR vaccine is supplied in freeze-dried form and the presence of stabilizers in the vaccine to reduce the moisture content have greatly improved their thermal stability (Galazka et al., 1998). The shelf life of lyophilized vaccines is dependent on both adherence to the cold chain and maintenance of low residual moisture content. As the storage temperature increases, so does the amount of water present in the air. The MMR-silk films were fabricated and air-dried at ambient conditions therefore had a higher initial residual moisture than both the lyophilized MMR powder and the lyophilized MMR-silk films. The residual moisture of the MMR-silk films calculated immediately after determination of a dried state was determined to be 4.42%±0.65. The residual moisture of the MMR powder and lyophilized MMR-silk films were calculated to be 2.39%±0.23 and 1.89%±0.13, respectively. With the exception of MMR-silk films, storage of the lyophilized vaccine systems after six months at 4° C. produced very little change in residual moisture. In fact, the residual moisture of the lyophilized films stored for six months at all the temperature points exhibited very little aberration from the initially measured value, displaying only a net increase of 6.9% in residual moisture from the initial value to the highest recorded value at 45° C. Due to the processing conditions, the MMR-silk films had higher residual moisture, but the net increase to the highest residual moisture value recorded at six months of storage at 45° C. was only 30.1% compared to the 61.5% increase shown in the MMR powder system. The residual moisture content of the vaccine systems corresponded to the residual potency. At the elevated temperatures, the MMR powder exhibited greater losses in potency than the silk films, correlating well with the greater increase in residual moisture. Similarly, the minimal increase of residual moisture of the lyophilized MMR-silk films resulted in a greater retention of viral potency.

TABLE 4

Comparison of the residual moistures of the MMR powder, MMR-silk films and lyophilized MMR-silk films at specific storage conditions.

| Vaccine System | Storage Condition | Residual Moisture (%) |
|---|---|---|
| MMR Powder | At t = O (Initial Condition) | 2.39 ± 0.23 |
| | After 6 months in 4° C. | 2.37 ± 0.15 |
| | After 6 months in 25° C. | 2.73 ± 0.54 |
| | After 6 months in 37° C. | 3.52 ± 0.35 |
| | After 6 months in 45° C. | 3.86 ± 0.28 |
| Lyophilized MMR-silk films | At t = O (Initial Condition) | 1.89 ± 0.13 |
| | After 6 months in 4° C. | 1.81 ± 0.20 |
| | After 6 months in 25° C. | 1.97 ± 0.43 |
| | After 6 months in 37° C. | 1.83 ± 0.35 |
| | After 6 months in 45° C. | 2.02 ± 0.52 |
| MMR-silk films | At t = O (Initial Condition) | 4.42 ± 0.65 |
| | After 6 months in 4° C. | 5.26 ± 0.51 |
| | After 6 months in 25° C. | 5.47 ± 0.53 |
| | After 6 months in 37° C. | 5.53 ± 0.70 |
| | After 6 months in 45° C. | 5.75 ± 0.91 |

Structural Characterization of Vaccine-Silk Systems

To investigate how the silk provided enhanced thermostability to the vaccines, physical measurements using calorimetry and light scattering were studied. DSC (FIG. 17) was used to demonstrate that the silk encapsulant provided stabilization to the vaccine by an increase in the glass transition (Tg) of the vaccine. Solid-state DSC of lyophilized silk films showed a Tg at 178° C. The DSC thermogram of the MMR powder showed a Tg at 68.9° C. while the lyophilized MMR-silk films showed a Tg at 89.2° C. as well as two peaks at 116.6° C. and 164.8° C. that could indicate a Tm, melting temperature, and Td, degradation temperature. It is unclear whether the shift in Tg was due to structural stabilization by the silk or the interaction between silk and the various excipients present in the vaccine sample. The vaccine was then purified to remove the added excipients. The resulting solution contained purified viral particles suspended in sterile, nuclease-free water. As the viral sample is a liquid solution, nano-DSC was run on these samples. The nano-DSC thermogram (FIG. 18) of the purified viral particles in water showed a Tm at 16.8° C., indicating the viral proteins were undergoing a conformational change. The solution of purified viral particles in silk showed an elevated Tm at 68.3° C. While the range of the nano-DSC does not extend far enough to show the Tg of the silk, a thermogram of silk solution is still shown to illustrate that neither of the Tg values can be attributed to a change in the silk structure. To investigate whether the Tm corresponded to viral particle denaturation due to aggregation, the size of the viral particles was examined by DLS (FIG. 19). The average mean effective diameter of a naked viral particle is around 250 mm. This is consistent with reported values of measles, mumps and rubella (Russell et al., 1967; Hall and Martin, 1973). The results indicated that the purified virus solution showed an increase in mean effective diameter around 16° C., indicating the presence of protein aggregation. The DLS of the viral particles in silk solution, on the other hand, did not show an increase in the mean effective diameter until around 70° C., showing protein aggregation at a more elevated temperature. The results of the DLS correspond well with the results of the nano-DSC as the aggregation detected by light scattering occur within the temperature range of the protein unfolding measured by DSC.

Vaccine Release from Silk Films, Lyophilized Silk Film, Silk Hydrogels and Silk Microspheres.

In order to demonstrate that silk provides not only stabilization of the vaccine but also control over vaccine release kinetics, release studies were conducted with a variety of silk formulations. Each silk formulation (film, lyophilized film, hydrogel and microsphere) contained the same initial amount of vaccine. Cumulative release profiles of the vaccine-encapsulated silk film and lyophilized silk films are shown in FIG. 20A-20B. In vitro release studies for these two systems were conducted with single films placed between two blocks of gelatin hydrogels, allowing for the release of vaccine as the silk films dissolved into the hydrogels. Vaccine-entrapped silk films prepared from 8% (w/v) silk solution exhibited a slight burst release, typical of diffusional release. At the last collection of 6 hours, nearly all the encapsulated vaccine was released as 92.43% of the vaccine was recovered and active. The silk films prepared with 4% (w/v) exhibited a similar release profile, only the burst release was faster as the mass released neared complete release more rapidly. The lyophilized silk films showed a more pronounced burst effect as the 8% silk films released 44% and the 4% films released 56% of the loaded MMR within 10 minutes of placement in the hydrogel. The lyophilized silk films released nearly all the MMR loaded within 90 minutes. The silk hydrogels and microsphere preparations exhibited a much slower release by comparison, on the order of days (FIG. 21A-21B). The 4% and 8% silk hydrogels extended the release of vaccine to 8 days. Furthermore, the 16% silk hydrogels were able to extend the release further as only 73.53% of the vaccine was released by day 8. Vaccine release from silk microspheres showed greater potential as an extended and sustained release system. Similarly, increasing the silk concentration of the microspheres slowed the release rate; the 16% silk microspheres released 65.35% of the loaded vaccine by day 8. The relative linearity of the release from the 16% silk microspheres is also of interest as the regression coefficient ($R^2$) for the curve was 0.988, indicating nearly zero-order release.

Biophysical characterization of the measles, mumps, and rubella vaccine through use of calorimetry and light-scattering allowed for a description of the physical stabilization of the virus as a function of elevated temperature during vaccine storage. Due to the temperature-sensitivity of the vaccines, the process of distribution and storing vaccines is fragile as these issues often come with considerable logistical cost (Zweig, 2006). It is known that the immobilization of bioactive molecules such as enzymes leads to an increase in stability while improving handling. Immobilization is important as is maintaining constant environmental conditions in order to protect bioactive molecules against changes in pH, temperature or ionic strength (Kumakura, 1995). The chemistry, structure and assembly of silk generates a unique nano-scale environment and makes this protein polymer an attractive candidate for the stabilization of bioactive molecules over extended periods of time (Jin and Kaplan, 2003). Without chemical processing, silk can be used to entrap bioactive molecules in the amiphilic, self-assembly domains from aqueous solution.

MMR® II, a live attenuated measles, mumps, and rubella vaccine, is provided as a lyophilized preparation to be reconstituted at time of use. Prior to reconstitution, the vaccine must be stored at 2 to 8° C. and will be stable for 24 months, and once reconstituted must be used within 8 hours. The WHO requirement for heat stability of measles, mumps and rubella vaccines employs two indices of stability: 1) the vaccine should retain at least 1,000 live virus particles in each human dose after incubation at 37° C. for seven days; and 2) the virus titre should not have decreased by more than 1 $\log_{10}$ during storage (WHO, 1982; WHO 1994). Live viruses vaccines, unlike other vaccine forms, depend on their immunogenicity to establish an appropriate immune response, which requires the retention of a sufficient numbers of live viral particles. Storage of these thermally labile viral particles requires the addition of stabilizers. Each dose of MMR® II is stabilized in 14.5 mg sorbitol, sodium phosphate, 1.9 mg sucrose, sodium chloride, 14.5 mg hydrolyzed gelatin, S0.3 mg recombinant human albumin, <1 ppm fetal bovine serum, other buffer and media ingredients and approximately 25 µg of neomycin.

Excessive exposure to temperatures above recommended storage conditions can damage vaccines in a number of ways, most notably alteration of the tertiary structure of the viral proteins, reducing viral infectivity and thereby decreasing vaccine potency (Chen and Kristensen, 2009). Changes in protein structure can lead to aggregation and altered cellular uptake, affecting vaccine activity (Brandau et al., 2003; Manning et al., 1989; Middaugh, 1996). Measles and mumps belong to the Paramyxovirus family, characterized as an enveloped virus containing the nucleocapsid that encloses the single-stranded negative-sense viral RNA surrounded by fusion (F) and haemagglutinin (H) glycoproteins expressed on the surface of the virus (FIG. 22A) (Kingston et al., 2008; Woelk et al., 2002). Similarly, rubella belongs to the Togavirus family and is an enveloped virus with two virus-specific glycoproteins E1 and E2 that surround a icosahedral nucleocapsid enclosing single-stranded positive-sense viral RNA (Dorsett et al., 1985; Nakhasi et al., 1991).

The method of infection of paramyxoviruses involve the attachment of the virus to the CD46 and CD150 receptors of host cells by interaction between both the haemagglutinin (H) glycoprotein and fusion (F) glycoprotein (FIG. 22C) (Wild et al., 1991; Malvoisin and Wild, 1993; Moss and Griffin, 2006). Fusion of the virus and cell allow for viral entry and release of viral nucleic material into the cell. The main cause of viral inactivation is disruption of viral surface proteins and stresses such as elevated temperatures can induce conformational changes in the viral proteins (Rexroad et al., 2006; Ausar et al., 2006). These conformational changes may affect the stability of the virus by inducing viral particle aggregation that prevents cell binding and uptake, thus leading to virus inactivation (FIG. 22D) (Ohtake et al., 2010). Developing a vaccine formulation that is resistant to heat damage and improving thermostability of the vaccine would have major benefits including extending the shelf-life, decreasing the loss of vaccines and reducing dependency on cold-chain requirements.

The improvement in vaccine stability provided by silk protein was more pronounced at the elevated temperatures of 37° C. and 45° C., while the stability was comparable or slightly better than the manufactured powder form stored at 4° C. and 25° C. The lyophilized vaccine is stabilized with a variety of excipients that according to the manufacturer should remain stable and active for at least two years. Vaccine spoilage, however, occurs when the cold chain is broken and the vaccine is stored above refrigeration temperature. In such cases, silk would provide sufficient stability to the vaccine to maintain stability over a range of environmental conditions. Lyophilization of the MMR-silk films improved initial vaccine potency recovered as the longer the viral particles remained in the hydrated state, the more likely they are to be exposed to degradative reactions such as hydrolysis and deamidation that may contribute to instability (Li, 1994). The continued enhanced stabilization provided by the lyophilized silk films over six months in storage could also be due in part to the conditions of storage for the lyophilized films. While the regular silk films were stored in Eppendorf tubes, the lyophilized films were stored in vacuum-sealed vials with low residual moisture content.

Evaluation of the experimental potency data by kinetic models of unfolding and degradation serves to illustrate the projected accelerated stability of the different vaccine systems under select temperatures while also relating the potency data to the temperature-induced conformational changes to be explained by the biophysical characterizations. Under accelerated stability study conditions, the intrinsic stability of protein pharmaceuticals is often decreased dramatically. At elevated temperatures, protein unfolding rates increase and most chemical interactions involved in destabilization of the protein are accelerated as compared to at lower temperatures (Creighton, 1990). Accelerating the degradation process via storage at elevated temperatures allows for the assessment of silk as a suitable candidate stabilizer to inhibit the inactivation process. Examination of the potency data suggested that the degradation observed by the three vaccine systems could be fitted to a zero-order kinetic system. Observation of a concentration-time profile of zero-, first-, and second-order reactions show that zero-order kinetics always predict the greatest degree of composition as a function of time amongst the three. Therefore, when predicting the order of a reaction, assumption of a zero-order kinetic model will predict the maximum amount of degradation that could occur at some future time (Zhou et al, 2009). Therefore, in assuming the degradation of the MMR virus is pseudo zero-order, using zero-order kinetics to model the degradation profile, we predicted the most conservative estimates for the half-life of the vaccine-encapsulated silk film and lyophilized silk film systems.

The general trend observed for all three virus components was that both types of the silk films decreased the degradation rates of the viruses and the lyophilized silk systems exhibited the lowest degradation rates, and thus largest half-lives, amongst the three systems, while the powder form of the vaccine degraded the fastest at all the temperature points tested. Deviation from this trend was observed in the 4° C. samples as the powder vaccines show a lower degradation rate with a high predicted half-life over the non-lyophilized silk films. A possible explanation for the results is that the powder vaccine has the advantage of lyophilized preparation over the regular silk films. During the film preparation, additional moisture was introduced to the encapsulated vaccine that increases the intermolecular mobility and chances for degradation within the silk films compared to the manufacturer-provided vaccine powder. Undoubtedly, the silk films provide increased stability at elevated temperatures even with the handicap of additional moisture. However, the lyophilized vaccine powder has been formulated to remain stable at the optimum temperature range of 2 to 8° C. This advantage of lyophilization could also explain the success of the lyophilized silk films at stabilizing the vaccine as they provide the stability offered by both the silk and lyophilization.

In addition to the kinetic studies performed using the potency data, biophysical characterizations using calorimetry and light scattering were conducted to corroborate the results. Due to the high glass transition temperature of silk fibroin, 178° C., silk protein is thermodynamically stable once self-assembled into the β-sheet conformation. These features provide an environment to stabilize the vaccine. The vaccine-silk solution consisted of vaccine molecules in native form and the silk fibroin mainly present in random coils. Once the films are cast, there is some conversion of the fibroin into β-sheets, which contain hydrophobic regions, while the random coils contain the more hydrophilic regions. The vaccines seem to be stabilized in this environment, possibly due to interactions with the fibroin chains or the constraints on chain mobility (FIG. 21B). The sold-state DSC (FIG. 17) showed a Tg of the MMR powder at 68.9° C. This value, however, can be misleading as it may not reflect the Tg and corresponding structural change of the viral particles themselves but rather an averaged value from the contributions of the various protein excipients and stabilizers already present in the MMR powder vaccine formulation. MMR-silk film showed a Tg at 89.2° C., indicating a shift in the Tg of the vaccine due to the presence of the silk. The thermogram of the lyophilized MMR-silk film, however, also showed the presence of two exothermic peaks at 116.6° C. and 164.8° C. The peak at 116.6° C. was mostly likely a Tm, indicative of protein unfolding, while the second peak was degradation, Td. It cannot be determined whether the unfolding and degradation contributed to the viral proteins or the various excipients present in the vaccine formulation. It is, therefore, difficult to conclusively say that the increase in Tg of the vaccine in the presence of silk was directly contributing to the structural stability of the viral particles.

In order to clarify the situation, the vaccine was purified to remove excipients. Since the result of the purification is a liquid preparation, the viral particles are in a less stable environment. Therefore, the viral particle solution was stored at −80° C. until used. The Tm by nano-DSC appeared when a protein unfolds, exposing the hydrophobic and hydrophilic regions to the aqueous buffer solution. Adjacent hydrophobic protein molecules will aggregate to shield these regions from the surrounding aqueous solution. Because the unfolded state of proteins have more surface area than the native state, the degree of preferential exclusion offered by the stabilizing agent of silk from the less structured state would raise the chemical potential of this stabilized form even above that of the native state (Brandau et al, 2003). This increased stability can be reflected in the increase of the midpoint of the unfolding transition of the proteins, Tm. The elevated Tm of the vaccine-encapsulated silk solution is due to structural stabilization provided by the silk to prevent viral protein denaturation and aggregation. The Tm value at 16.8° C. is likely due to the unfolding of the viral surface glycoproteins (F and N of measles and mumps and E1 and E2 of rubella) due to the elevated heat applied to the viral particles. This denaturation most likely leads to the aggregation of the viral particles (FIG. 22D), preventing them from binding and fusing with the animal cells (FIG. 22C), leading to loss of infectivity of the viral particles and vaccine as a whole. This associated aggregation is shown on the DSC thermogram as the sharp change in heat flow immediately following the Tm. It appears the aggregation, an exothermic process, is a direct result of the endothermic unfolding of the protein. The broadness of the Tm peaks is most likely a result of the combined contribution of the unfolding of several proteins present in the sample. Furthermore, the protein aggregation may also contribute to the broad peaks by overlapping with the denaturational endothem (Packer et al., 2002). The infectivity of MMR is dependent on the conformational stability of the viral proteins (Kissman et al, 2008). The increase in Tm by the presence of silk molecules indicates that the silk provided structural stability to the viral proteins that shielded them from thermal denaturation. The interaction between the viral particles and the silk hydrophobic regions, as well as limited chain mobility, might prevent viral protein aggregation (FIG. 22B), thereby preserving viral and vaccine infectivity.

Unfolding of a protein is usually associated with an increase in its hydrodynamic size as the partial or fully unfolded proteins states are unstable and form aggregates (Roberts, 2007). The results of the light scattering indicated that the naked viral particles aggregated at a much lower temperature than a solution of viral particles in silk. The onset of particle aggregation as verified by DLS occurs around the same temperature of protein unfolding as shown by DSC, indicating the protein unfolding directly resulted in aggregation. The DLS results corroborate the results of the DSC that the silk provides structural stability to the viral particles, particularly to the viral surface glycoproteins, preventing intermolecular collisions and thus minimizing aggregation at elevated temperatures.

Humidity can also have a significant effect on vaccine products as the excess water introduced to the system can lead to increase in mobility and corresponding reactivity of the viral proteins (Waterman and Adami, 2005). The residual moisture analysis of the films reveal that over the course of the stability testing the increase in residual moisture, especially in the high temperature ranges, is most likely due to the lack of moisture-controlled environment provided by the Eppendorf tubes. While the MMR powder and lyophilized MMR-silk films were stored in low humidity conditions as they are extremely hygroscopic, provided by the lyophilization vials and stopper, and sealed in a nitrogen-rich environment, the MMR-silk films were stored in Eppendorf tubes that would allow greater chances for absorption of the atmospheric humidity into the containers than the vacuum-sealed vials. The increased water activity in the Eppendorf tubes is also due to the amount of initial water associated with the silk films, already at a higher level than both the powder and lyophilized films, and the initial packaging relative humidity. The increase in residual moisture exhibited in the silk films at elevated temperatures could also be explained by possible water desorption from the silk, that though allowed to air dry still contain trace amounts of intermolecularly bound water molecules within the silk matrices (Hu et al., 2007). Moreover, for the silk films stored at room temperature, the variability of the atmospheric humidity dictated by the weather patterns would affect the relative humidity inside the Eppendorf tubes.

Though the effect of residual moisture on the vaccine was taken into consideration, the silk films were stored in Eppendorf tubes simply to show that with minimal processing conditions and with no special storage consideration, vaccine-entrapped silk films are able to display enhance stability at elevated temperatures over commercially available lyophilized vaccines tested at the same temperatures. The mobility increase due to moisture and temperature would explain how the lyophilized silk films exhibited such dramatic increases in stability of the regular silk films. The lyophilization process and low moisture storage of the lyophilized films significantly limited the mobility of the viral proteins at high temperatures, causing the viral proteins to be resistant to thermally-induced unfolding and the associated aggregation. Even though the absolute residual moisture of the silk films is higher than that of the MMR powder, the percent increase of the residual moisture in the powder over the tested temperature range is greater than that observed in the silk films. The increase in temperature appears to have had a greater impact in the temperature-induced moisture in the powder than the silk films. It would appear the silk provided an inhibition of molecular mobility during storage to prevent protein unfolding and subsequent aggregation whereas the increased water activity in powder resulting from temperature-induced moisture, without the conformational stability provided by the silk, increased viral protein aggregation.

Release studies were carried on a variety of vaccine-entrapped silk delivery vehicles to show that silk was able to stabilize the vaccine and control release kinetics. Vaccine-loaded silk films and lyophilized silk films were untreated and water-soluble. They have the potential to be molded into delivery formats such as microneedles, a safe and pain-free alternative to transdermal drug delivery over hypodermic needles (Tsioris et al., 2011). Conceivably, a patch could be applied to the skin and the vaccine-loaded silk microneedles would puncture the skin, the silk needles would dissolve and release the vaccine subcutaneously. The release profile of the silk films show promise toward this goal. The release studies for the silk films and lyophilized silk films were conducted in a gelatin hydrogel due to a consistency analogous to tissue (Wightmas et al., 2007). The silk films cast from 4% and 8% silk displayed similar release profiles (FIG. 20A-20B), showing an initial burst of release followed by a decreased rate of release. The 4% silk film exhibited a more rapid release due to the lower concentration of silk protein, allowing the vaccine to diffuse faster from the matrix while also allowing the film to dissolve more rapidly. As the silk concentration increased to 8%, the release rate slowed due to the increased β-sheet content of the film, forming a more rigid matrix and slowing the diffusion of vaccine into the hydrogel. The release profiles of the lyophilized silk films showed a more pronounced initial burst effect. Rather than the vaccine quickly diffusing from the silk upon initial contact with the hydrogel, the initial burst from the lyophilized films was most likely due to the rapid dissolution of the lyophilized films. The subsequent release was likely due to the diffusion of the vaccine from the undissolved film. For the same reason as the silk films, the 4% lyophilized silk films exhibited a faster release profile than the 8%. While the time scale of silk film release was on the order hours, 96.85% of the encapsulated MMR was released by 90 minutes.

Vaccine-silk delivery vehicles were also fabricated in insoluble formats of silk hydrogels and microspheres. These forms could be incorporated into injectable vaccine delivery that forms a subcutaneous vaccine depot able to slowly release the vaccine over an extended period of time. The hydrogels and microspheres released the vaccine over a period of days. The slower drug release can be explained by diffusion of the vaccine, limited by the increased β-sheet content of the hydrogels and microspheres. Also, as the concentration of the hydrogels and microspheres was increased, the linearity of release of improved, corresponding to a decrease in release rate. Increasing the silk concentration of the hydrogels resulted in a decrease in vaccine release rate. Increasing the silk concentration of the MMR-silk microspheres, however, slowed the release rate and the release rates became more linear, approaching zero-order. The 8% microspheres had a regression coefficient ($R^2$) of 0.95 and the 16% silk had a value of 0.988. The increased linearity of vaccine release from microspheres could be due to the small volumes that generate a smaller diffusion gradient for the vaccine particles to cross into the bulk phase.

These results indicate that these silk entrapped vaccine systems can be fabricated to provide thermal stability for vaccines at elevated temperatures, while also functioning as a controlled and sustained vaccine delivery system. Entrapment of MMR vaccine in lyophilized silk films showed enhanced stability at elevated temperatures outside the recommended cold-chain for a period of time well beyond that of the manufacturer's vaccines. The choice of silk as a encapsulating polymer also supports the safety of the implantable or injectable vaccine-silk system since silk is a biocompatible, biodegradable and FDA-approved biomaterial (Altman et al, 2003; Horan et al, 2005).

Vaccine-encapsulated silk films and lyophilized silk films provide a highly effective carrier for the long-term thermostabilization of the measles, mumps and rubella vaccine. Both silk film systems were able to increase the half-lives of all three viral components of the vaccine compared to the manufacturer supplied vaccines at 25° C., 37° C. and 45° C. The silk reduces the temperature-induced viral protein unfolding and subsequent aggregation by reducing the residual moisture of the samples during storage at elevated temperatures and also providing structural stability to the vaccine to elevate the temperature at which the viral proteins denature. Furthermore, the silk carriers can be fabricated into different delivery vehicles capable of tailoring the release kinetics of the vaccine. This silk carrier system provides a novel vaccine delivery system easily fabricated without special processing considerations and capable of maintaining the potency of the vaccine without the need for strict adherence to the cold chain.

Example 3 Methods

Trivalent vaccine. For potency estimation, we used a commercial source of trivalent measles, mumps, rubella vaccine MMR® II (Merck & Co., Inc., USA), a sterile lyophilized live virus vaccine containing the Enders' attenuated Edmonston measles, the Jeryl Lynn mumps and Wistar RA 27/3 rubella. Prior to use, the vaccine was reconstituted in diluent and each 0.5 mL dose contained no less than 1,000 $TCID_{50}$ (tissue culture infectious dose) of measles virus; 12,500 $TCID_{50}$ of mumps virus; and 1,000 $TCID_{50}$ of rubella virus. Manufacturer conditions state that the vaccine must be used within 8 hours of reconstitution and stored at 4° C. or otherwise be discarded. Each 0.5 mL dose contains sorbitol (14.5 mg), sodium phosphate, sucrose (1.9 mg), sodium chloride, hydrolyzed gelatin (14.5 mg), recombinant human albumin (<0.3 mg), fetal bovine serum (<1 ppm), other buffer and media ingredients and approximately 25 µg of neomycin.

Silk Fibroin Purification.

Silk fibroin aqueous solutions were prepared as previously described (Wang et al., 2008). Cocoons of B. mori silkworm silk were boiled for 30 minutes in an aqueous solution of 0.02 M $Na_2CO_3$ and then thoroughly rinsed with dl water to extract the sericin. After drying, the silk was dissolved in a 9.3 M LiBr solution at 60° C. for 4-6 hours and then dialyzed in distilled water using Slide-a-Lyzer dialysis cassettes (MWCO 3,500, Pierce) for 48 hours. The solution was centrifuged to remove silk aggregates and other insoluble residues. The final concentration of silk fibroin was approximately 9% (w/v). The solutions were then autoclaved for sterility.

Virus Purification.

Lyophilized vaccine powder was reconstituted in sterile water and loaded into 0.5 kDa dialysis tubing (Sigma Aldrich) and dialyzed against a 0.15M NaCl solution to remove the excipients from the vaccine solution. The recovered vaccine solution was then run through a PD-10 desalting column (GE Healthcare) to remove excess salt. The spin protocol was followed per manufacturer specifications. The recovered purified viral particle solution was collected and stored in an Eppendorf tube at −80° C. until use.

Vaccine Entrapment in Silk Films.

Figure 1:
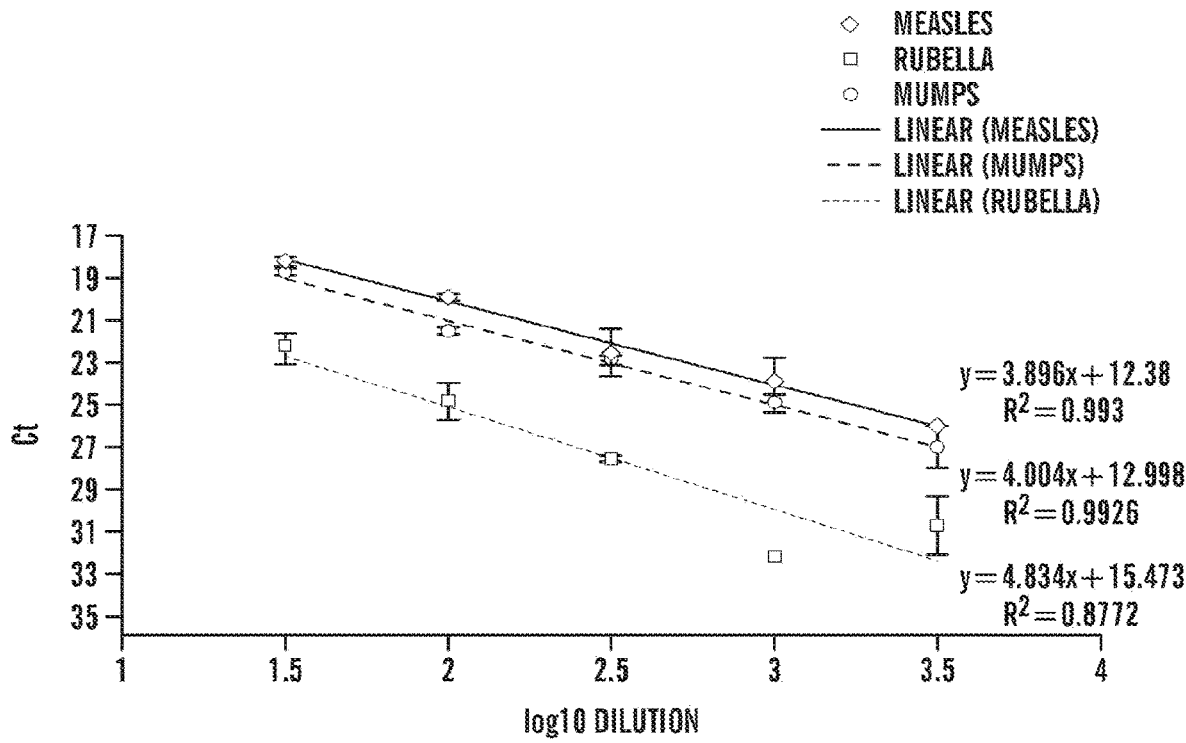
FIG. 1 shows the linear relationship between the $\log_{10}$ dilution of the vaccine sample and the Ct values for measles, mumps and rubella. N=3, error bars represent standard deviations.
Figure 2:
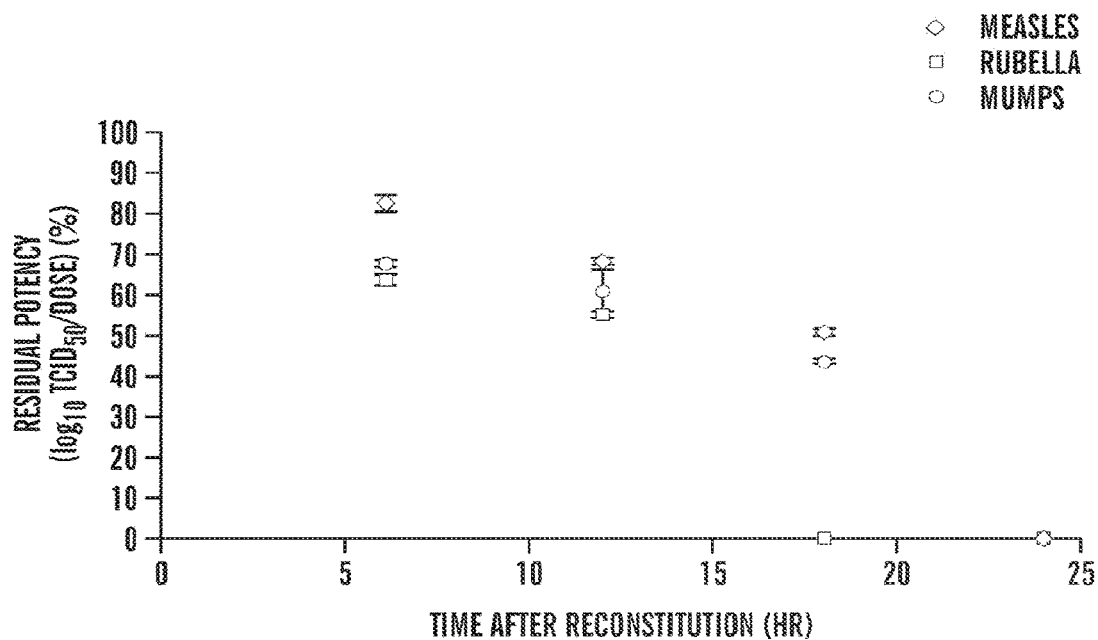
FIG. 2 shows results of reconstituted MMR vaccine at 24, 18, 12 and 6 hours in water prior to cell inoculation stored at 25° C. protected from light. N=3, error bars represent standard deviations.
Figure 3:
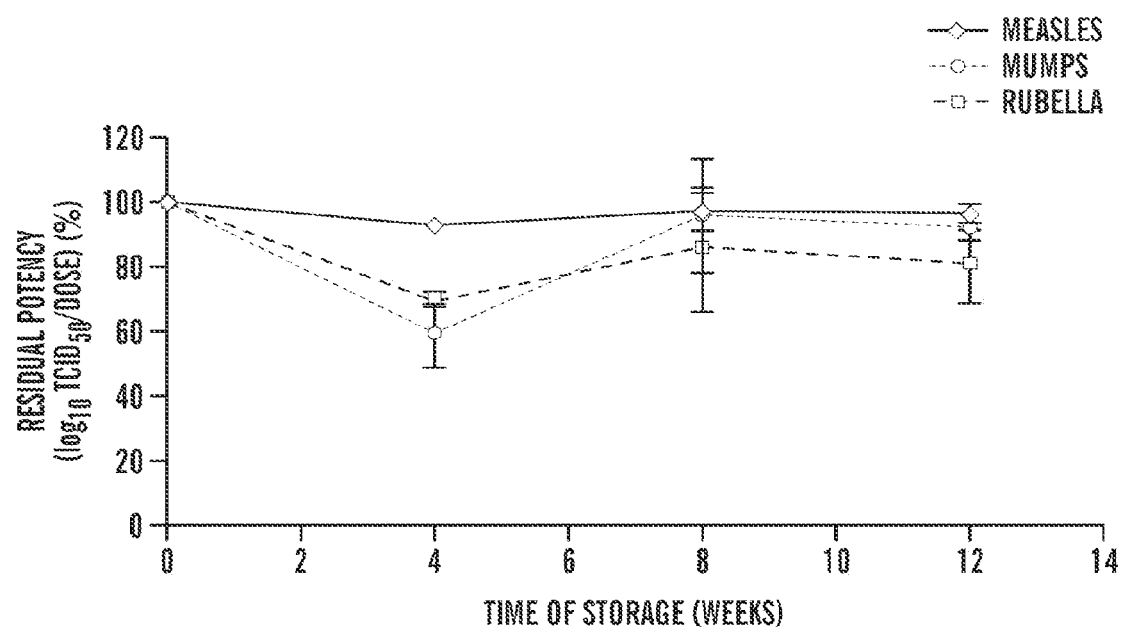
FIG. 3 shows the stability of measles, mumps and rubella virus stored in 9% (w/v) silk films over 3 months. N=3, error bars represent standard deviations.
Figure 4:
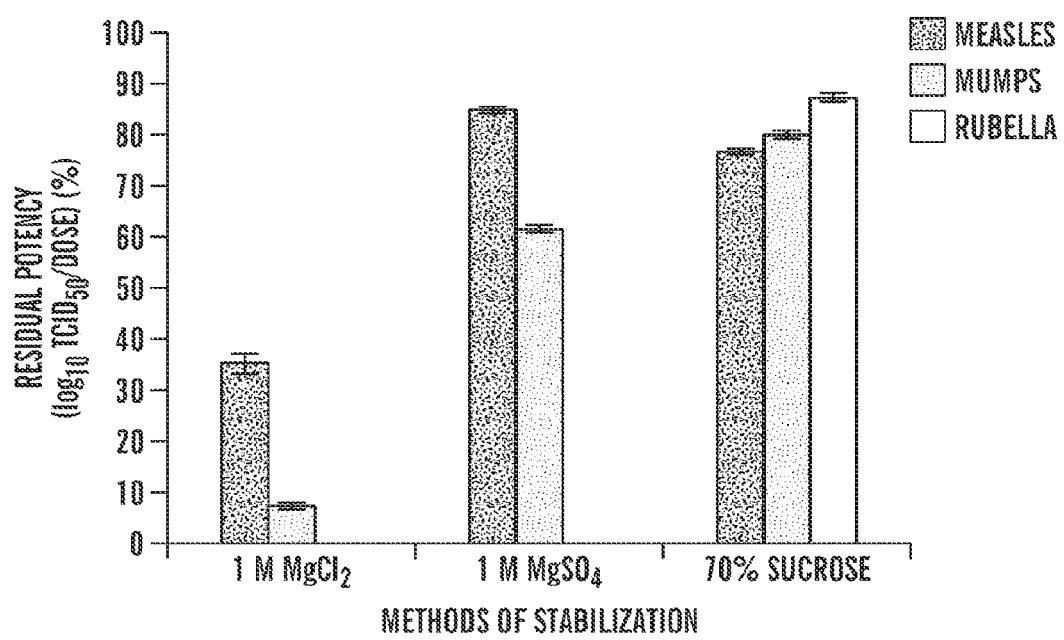
Figure 5:
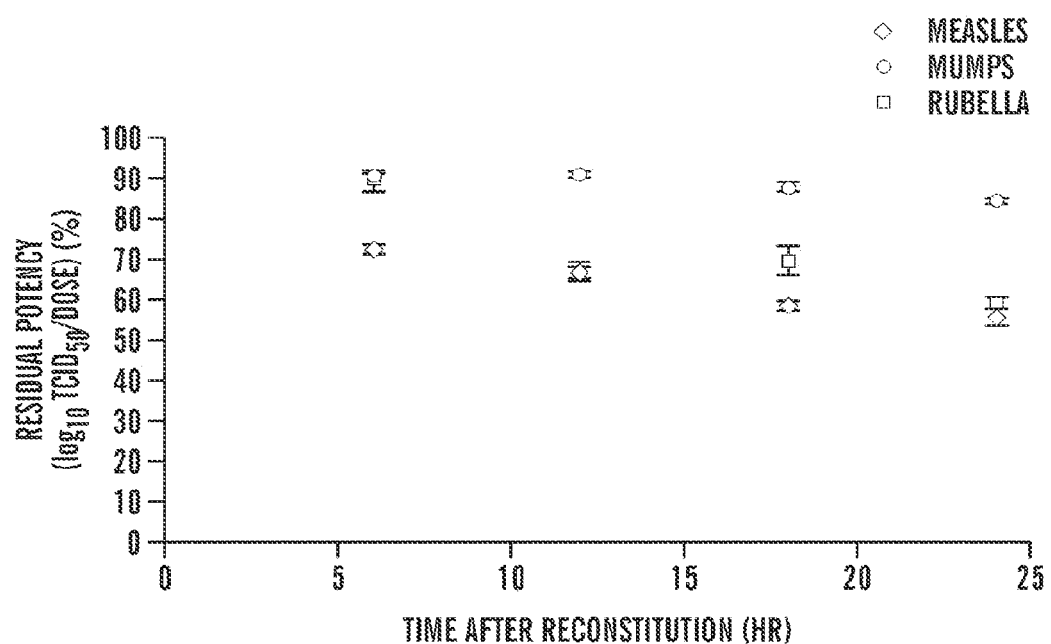
Figure 6A:
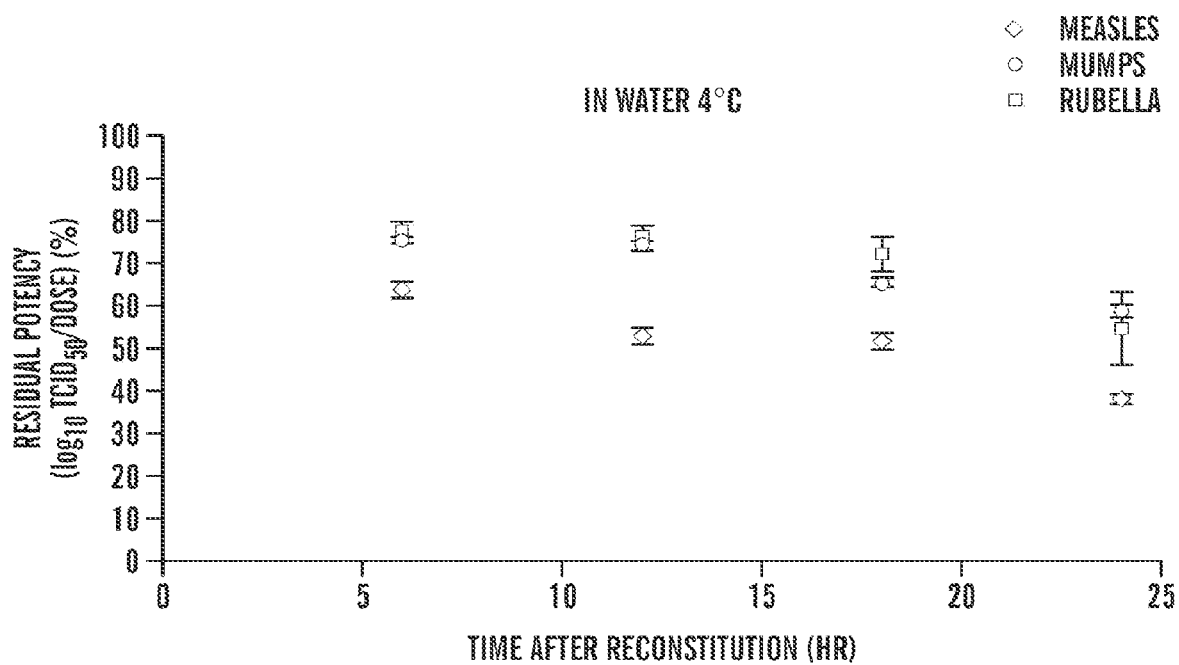
Figure 6B:
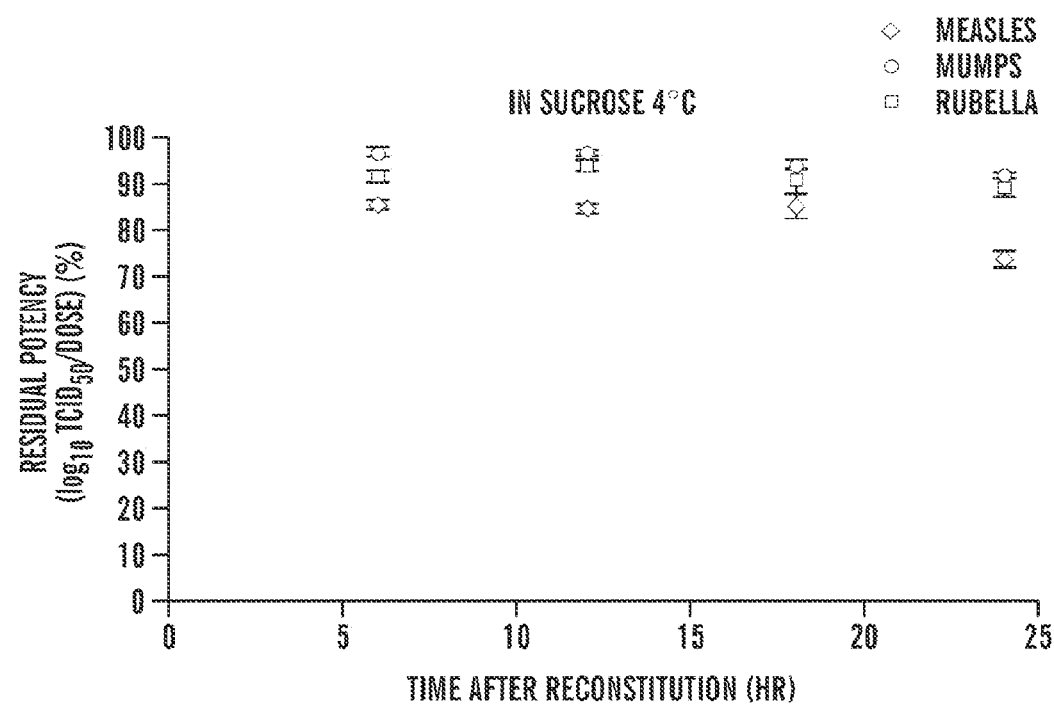
Figure 6C:
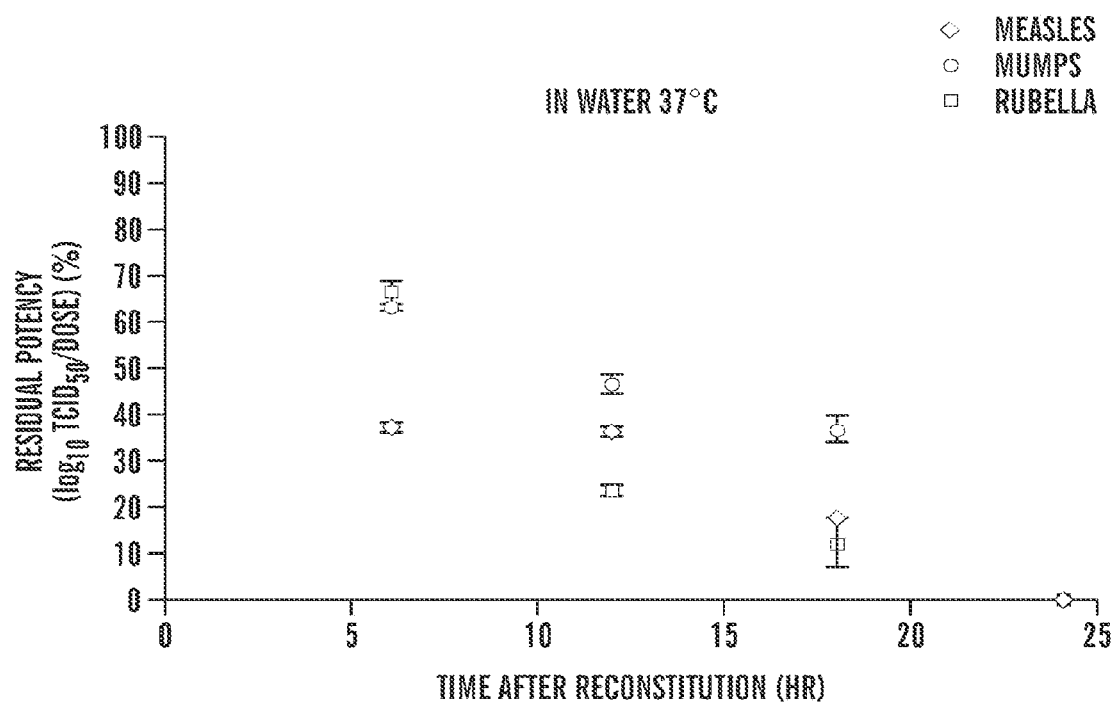
Figure 6D:
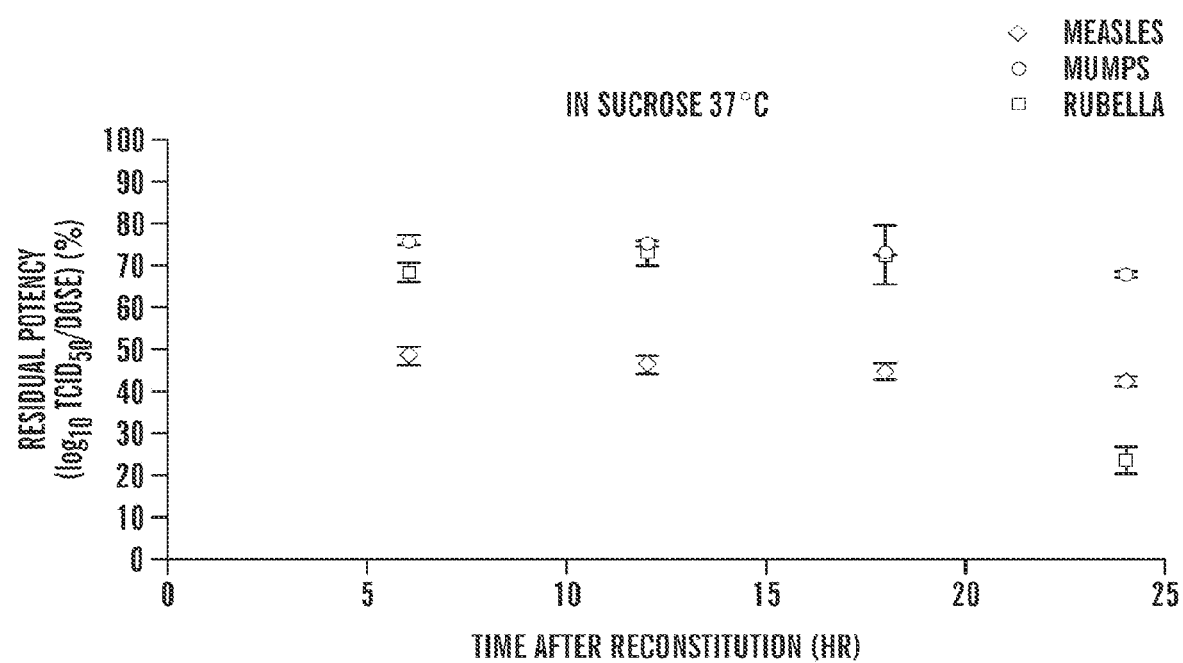
Figure 7:
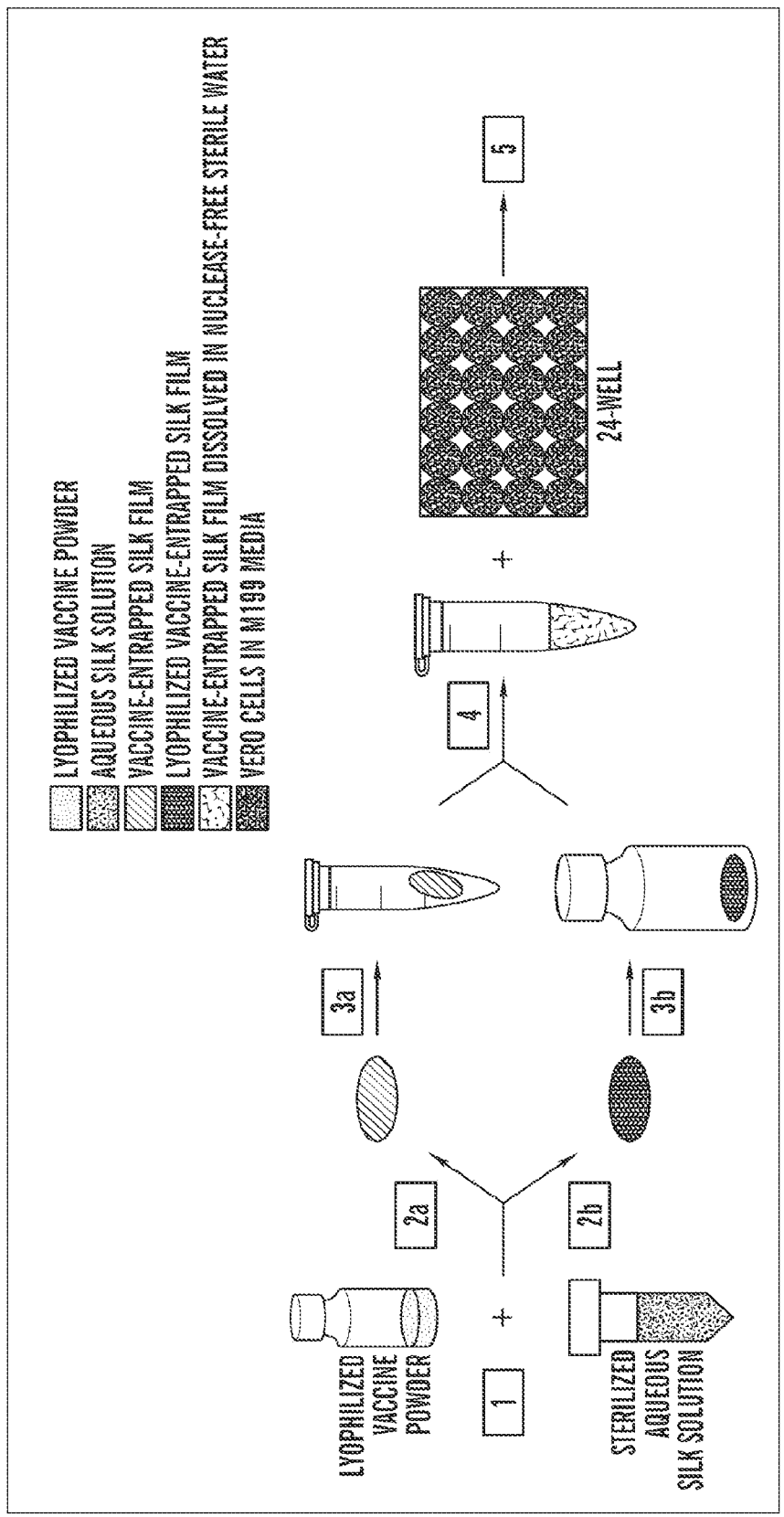

The process for vaccine-encapsulated silk film fabrication is illustrated in FIG. 7. A mixture of sterilized 9% (w/v) silk solution and lyophilized MMR vaccine were prepared at a concentration of 1:1 by weight ratio of MMR to silk solution. Films were then cast onto a Teflon-coated surface. The films were allowed to dry in a sterile hood for 12 hours at room temperature, protected from light. Individual films were placed in Eppendorf tubes, under ambient conditions, and stored at 4° C., 25° C., 37° C. and 45° C. for stability studies.

Lyophilization of Vaccine-Entrapped Silk Films.

MMR-silk solutions (1:1 weight ratio) were aliquoted into 96-well plates and freeze dried using a VirTis 25L Genesis SQ Super XL-70 Freeze Dryer. The samples were frozen at −45° C. for 480 minutes. The primary drying occurred at −20° C. for 2,400 minutes and secondary drying at 35° C. for 620 minutes. The samples were held at −45° C. until they were removed from the lyophilizer. The films were then removed from the well plates and transferred to 5 cc glass serum vials. Five mm lyophilization stoppers were applied to the vials under nitrogen and vacuum conditions in a MBRAUN LABmaster glovebox (Garching, Germany) and a 5 mm crimper was used to tighten the 5 mm alum seal on the vials. The vials were stored at 4° C., 25° C., 37° C., and 45° C. for stability studies. The vials, stoppers, seals and crimper were supplied by VWR (Bridgeport, NJ).

Vaccine Entrapment in Silk Hydrogels.

The silk solution was adjusted to concentrations of 2-5 wt % and then autoclaved for sterility. Then 1 mL of the silk solution was transferred into an autoclaved 2 mL Fisher glass vial, and the solution was mixed in the glass vial for 7 minutes at 3,200 rpm using a Fisher vortexer. The turbid solution was collected and transferred into 2 mL Eppendorf tubes, the vaccine was gently mixed into the solution at a 1:1 wt. ratio solution. The vaccine-silk solution was incubated in the Eppendorf tube at room temperature until gelation. The gels were then refrigerated for longer term storage.

Vaccine Entrapment in Silk Microspheres.

The production of vaccine-loaded microspheres from silk/PVA blends used the procedure described by Wang et al. (2010). Vaccine powder was added to a 5 wt % silk solution to reach a weight ratio of 1:1000. This solution was gently blended with a 5% (w/v) PVA (polyvinyl alcohol, mol wt 30,000-70,000, Sigma Aldrich) stock solution. Using a consistent weight ratio of 1:4, a 5% (w/v) silk-PVA solution was prepared by mixing 1 mL of 5 wt % silk solution with 4 mL of 5 wt % PVA solution. The silk solution was autoclaved for sterility. After mixing, the solution was stirred for 2 hours at room temperature. Then the 5% (w/v) solution was transferred to a 35 mm Petri dish. The solution was allowed to dry overnight in a fume hood. The dried films were dissolved in 30 mL of ultrapure water with 10 minutes of gentle shaking at room temperature and then centrifuge at 16,000 rpm for 20 minutes at 4° C. The supernatant was discarded and the pellet resuspended in 30 mL ultrapure water and centrifuged again. The final pellet was suspended in 2 mL of ultrapure water.

Quantitative Real-Time RT-PCR Infectivity Assay.

A standard curve was generated by serially diluting a solution of the only the vaccine reconstituted in sterile water. The reconstituted vaccine, considered as the 1 $\log_{10}$ dilution, and was serially diluted in 0.5 $\log_{10}$ steps from 1.5 $\log_{10}$ to 3.5 $\log_{10}$ The MMR-silk films (containing 1 $\log_{10}$ dilution of vaccine) were redissolved in an aliquot of water and the solution was added directly to the cultured cells. Vero cells (African green monkey kidney cells) (ATCC, Manassas, VA) were cultured in M199 medium with 25 mM hepes and L-glutamine (Sigma-Aldrich, St. Louis, MO), 1% penicillin/streptomycin (Invitrogen Life Technologies, Carlsbad, USA) and 5% fetal calf serum (Invitrogen). The cells were trypsinized, counted and adjusted to 50,000 cells/mL and plated in 24-well plates. Next, 50 µL of the vaccine dilution and redissolved silk film were added to a well of Vero cells in triplicate. The virus was allowed to replicate in the cells for 3 days, then the RNA from the infected cells was isolated, converted to cDNA and quantitated using qPCR. A log-linear relationship exists between the amount of target RNA and the PCR cycle where the fluorescence raises above the background (threshold cycle, Ct). The more viable the viruses that are present in the sample, the quicker and fewer cycles it takes for the fluorescence of the PCR product to be above background and therefore, the lower the Ct value. To account for variable cell growth, each time an assay is run, a standard curve was generated by serially diluting a vaccine solution containing the same amount of vaccine loaded in the MMR-silk films. Viral infectivity was measured right after the initial film preparation to establish baseline activity (time 0). Measurements at subsequent time points were compared to the time 0 value to establish residual potency. The initial recovered potency from silk films, viral activity immediately after casting film, was determined by comparison of viral infectivity measured from the MMR-silk films to the infectivity of a solution of vaccine alone, containing the same concentration of vaccine as loaded in the silk films. Residual potency in the MMR-silk films was calculated by the viral infectivity measured at the certain time point compared to the initial recovered potency and the residual potency of the vaccine powder in storage was measure by comparison of viral activity compared to the infectivity of the vaccine solution used to determine the initial recovered potency from silk films. As controls, viral activities were also measure for the silk films with no vaccines loaded.

RNA was isolated from the Vero cells using TRizol reagent (Invitrogen) and chloroform. The RNA was purified using the Qiagen RNEasy kit (Qiagen, Valencia, CA). Reverse transcription was performed in the purified RNA to synthesize cDNA using the High Capacity cDNA Reverse Transcription kit (Applied Biosystems, Foster City, CA). Real time RT-PCR was performed on a Strategene Mx3000P QPCR System (Strategene, La Jolla, CA). PCR reaction were carried out in 50 µL mixture volumes containing TaqMan Universal PCR Mater Mix (1×) (Applied Biosystems, Foster City, CA), 0.9 µM of each PCR primer and 0.25 µM of the probe with 5 µL of the cDNA sample. For measles detection, a 114 bp fragment (nt 584-697) was amplified with forward primer (5'-CCCTGAGGGATTCAACATGAT-TCT-3') (SEQ ID NO:1), reverse primer (5'-ATC-CACCTTCTTAG CTCCGAATC-3') (SEQ ID NO:2) and probe (5' FAM-TCTTGCTCGCAAAGGCGGTTACGG-BHQ1 3') (SEQ ID NO:3) (Hubschen et al., 2008). For rubella detection, forward primer (5'-TGATACCCA-GACCTGTGTTCAC-3') (SEQ ID NO:4), reverse primer (5'-GGTCGATGAGG ACGTGTAGG-3') (SEQ ID NO:5) and probe (5' JOE-GATCACCCAGCACTCCACGCAA-BHQ1 3') (SEQ ID NO:6) were used to amplify a 129 bp region (nt 195-323) (Hubschen et al., 2008). For detection of a 134 bp region of the mumps virus, forward primer (5'-CATAGGAGATATGTGGGG-3') (SEQ ID NO:7), reverse primer (5'-GTCTTCGCCAACGATG GTGATGATTG-3') (SEQ ID NO:8) and probe (5' JOE-CCATGCAGGCGGT-CACATTCCGACAA CTGC-TAMRA 3') (SEQ ID NO:9) were used (Kuhar et al., 2004). All primers and probes were obtained from Sigma-Aldrich (St. Louis, MO). PCR reaction conditions were 2 min at 50° C., 10 min at 95° C., and then 50 cycles at 95° C. for 15 s and 60° C. for 1 min.

In Vitro Vaccine Release.

In vitro vaccine release studies were carried out at 37° C. The release studies for the silk films and lyophilized silk films were carried out in a gelatin hydrogel model. The gelatin hydrogel was prepared by mixing 4.5 g of Knox™ original unflavored gelatin powder with 40 mL of boiled DI water to obtain a 0.112 g/mL hydrogel. The solution was poured into a 35 mm Petri dish and allowed to cool. To begin a release study, a film was placed between two slabs of the hydrogel. Once a time point was reached, the film was removed from the gel to stop the release. The hydrogels were then digested in 400 µL of 1 mg/mL collagenase (Sigma Aldrich) for 2 hours at 37° C. Subsequently, the MMR released was quantified by the Vero cell infectivity assay.

The in vitro release of the silk hydrogels and microspheres were carried out in 2 mL Eppendorf tubes. Each hydrogel or microsphere solution was placed in an Eppendorf tube with the addition of 1.5 mL of sterile PBS. At each time point, the PBS inside the Eppendorf tube was removed and transferred to another Eppendorf tube and stored at −80° C. Fresh PBS was then added to the tubes to replenish the supply. Once all the samples were taken at the set time points, the solutions were run through the Vero cell infectivity assay to quantify the amount of MMR released. The release values were reported as cumulative MMR released.
Residual Moisture Determination.

Residual moisture of the lyophilized vaccine powder, MMR-silk films, and lyophilized MMR-silk films was measured by the thermo-gravimetric method, modified from Worrall et al., 2001, that estimates the mean weight of three samples of each vaccine system after drying for one hour at 80° C. The weight of water lost from the dried vaccine system is expressed as a percentage.

Differential Scanning Calorimetry (DSC).

Five mg of were encapsulated in Al pans and heated in a TA Instrument Q100 DSC (New Castle, DE) with a purged dry nitrogen gas flow of 50 mL/min. Tg was recorded as the onset temperature of the discontinuity curve of the heat flow versus temperature. All measurements were made at 10° C./min. The samples were initially equilibrated at −20° C. for 5 minutes and then heated to 200° C., held at 200° C. for 5 minutes, followed by cooling to 20° C. Nano-DSC measurements were taken on a CSC Model 6100 Nano II Differential Scanning calorimeter (Lindon, UT). Samples were prepared at a concentration of 1 mg/mL. The scanning rate was set at 1° C./min for both the heating and cooling runs from O to 100° C.

Dynamic Light Scattering (DLS).

The size of the measles, mumps and rubella viral particles as a function of temperature was monitored by DLS. A 400 µL aliquot of 2 mg/mL sample solution was filtered through a 0.45 µm syringe filter (GE, Fairfield, CT). DLS was conducted using the DynaPro DLS system (Wyatt Technology, Santa Barbara, CA) with parameters set at 60 sec acquisition time, 10 number of acquisition and laser power of 75 mW. A 100 µL aliquot of the sample was transferred into an RNAse-free, DNAse-free, protein-free UVette Eppendorf cuvette to be inserted into the DLS. The effective hydrodynamic diameter was calculated from the diffusion coefficient by the Stokes-Einstein equation using the method of cumulants (Koppel, 1972).

Example 3 References

Adu, F. D., Adedeji, A. A., Esan, J. S. and Odusanya, O. G. (1996). Live viral vaccine potency: an index for assessing the cold chain system. *Public Health*. 110: 325-330.

Altman, G. H., Diaz, F., Jukuba, C., Calabro, T., Horan, R. L., Chen, J., Richmond, J., and Kaplan, D. L. (2003). Silk-based biomaterials. *Biomaterials*. 24: 401-416.

Arora, A., Prausnitz, M. and Mitragotli, S. (2008). Microscale devices for transdermal drug delivery. *International Journal of Pharmaceutics*. 364: 227-236.

Arya, S. C. (2001). Stabilization of vaccines: to be or not to be. *Vaccine*. 19: 595-597.

Ausar, S. F., Hudson, T. R., Hudson, M. H., Vedvick, T. S. and Middaugh, C. R. (2006). Conformational stability and disassembly of Norwalk virus like particles: effect of pH and temperature. *Journal of Biological Chemistry*. 281: 19478-19488.

Beauchamp, J. and Mansoor, 0. (1992). Temperature and the storage of vaccines. *New Zealand Medical Journal*. 105: 135.

Bishai, D. M. (1992). Vaccine storage practices in pediatric offices. *Pediatrics*. 89: 193-196.

Brandau, D. T., Jones, L. S., Wiethoff, C. M., Rexroad, J. and Middaugh, C. R. (2003). Minireview: Thermal Stability of Vaccines. *Journal of Pharmaceutical Sciences*. 92(2): 218-231.

Chen, D. and Kristensen, D. (2009). Opportunities and challenges of developing thermostable vaccines. *Expert Review of Vaccines*. 8.5: 547-558.

Cheriyan, E. (1993). Monitoring the vaccine cold chain. *Archives of disease in childhood*. 69: 600-601.

Cheyne, J. (1989). Vaccine delivery management. *Reviews of infectious diseases*. 11: S617-S622.

Colinet G., Rossignol, J. and Peetermans, J. (1982). A study of the stability of a bivalent measles-mumps vaccine. *Journal of biological standardization*. 10: 341-346.

Creighton, T. E. (1990). Protein folding. *Biochemical Journal*. 270: 1-16.

Dorsett, P. H., Miller, D. C., Green, K. Y. and Byrd, F. I. (1985). Structure and function of the rubella virus proteins. *Reviews of Infectious Diseases*. 7(1): S150-S156.

Evans, M. and Pope, M. (1995). Vaccine handling and storage in general practice. *Health Trends*. 27: 124-126.

Galazka, A., Milstien, J., and Zaffran, M. (1998). Thermostability of Vaccines. In: Global Programme for Vaccines and Immunization. World Health Organization, Geneva.

Hall, W. W. and Martin, S. J. (1973). Purification and Characterization of Measles Virus. *Journal of General Virology*. 19: 175-188.

Health Protection Agency. (2007). Foreign travel associated illness, England, Wales, and Northern Ireland. 2007 Report. [Online]. Accessed at hpa.org.uk/Publications/InfectiousDiseases/TravelHealth/0708Foreigntravelassociatedillness2007/.

Hofmann, S., Wong Po Foo, C. T., Rossetti, F., Textor, M., Vunjak-Novakovic, G., Kaplan, D. L., Merkle, H. P. and Meinel I. (2006). Silk fibroin as an organic polymer for controlled drug delivery. *Journal of Controlled Release*. 111: 219-227.

Horan, R. I., Antle, K., Collette, A. I., Wang, Y., Huang, J. and Moreau, J. E. In vitro degradation of silk fibroin. *Biomaterials*. 26: 3385-3393.

Hu, X., Kaplan, D. L. and Cebe, P. (2007). Effect of water on the thermal properties of silk fibroin. *Thermochimica Acta*. 461: 137-144.

Hubschen, J. M., Kremer, J. R., de Landtsheer, S., and Muller, C. P. (2008). A multiplex TaqMan PCR assay for the detection of measles and rubella virus. *Journal of Virological Methods*. 149: 246-250.

Jin, H. J. and Kaplan, D. L. (2003). Mechanism of silk processing in insects and spiders. *Nature*. 424: 1057-1061.

Kingston, R. L., Gay, L. S., Baase, W. S. and Matthews, B. W. (2008). Structure of the nucleocapsid-binding domain from the mumps virus polymerase; An example of protein folding induced by crystallization. *Journal of Molecular Biology*. 379(4): 719-731.

Kissman, J., Ausar, S. F., Rudolph, A., Braun, C., Cape, S. P., Sievers, R. E., Federspiel, J., Joshi, S. B. and Middaugh C. R. (2008). Stabilization of measles virus for vaccine formulation. *Human Vaccines*. 4(5): 350-359.

Koppel, D. E. (1972). Analysis of macromolecular polydispersity in intensity correlation spectroscopy: The method of cumulants. *Jounral of Chemical Physics*. 57(11): 4814-4820.

Kuhar, A., Yapar, M., Besirbellioglu, B., Avci, Y., and Guney, C. (2004). Rapid and quantitative detection of mumps virus RNA by one-step real-time RT-PCR. *Diagnostic Microbiology and Infectious Disease*. 49: 83-88.

Kumakura, M. (1995). Effect of heat treatment on enzyme entrapped into polymer gels. *Journal of Molecular Catalysis B: Enzymatic*. L1-L6.

Lee, S., Schoneich, C., and Borchardt, R. T. (1994). Chemical instability of protein pharmaceuticals: mechanisms of oxidation and strategies of stabilization. *Biotechnology and Bioengineering.* 48: 490-500.

Liddle, J. L. M. and Harris, M. F. (1995). How general practitioners store vaccines. A survey in south-western Sydney. *The Medical Journal of Australia.* 162: 366-368.

Malvoisin, E. and Wild T. F. (1993). Measles virus glycoproteins: studies on the structure and interaction of the haemagglutinin and fusion proteins. *Journal of General Virology.* 74: 2365-2372.

Manning, M. D. and Borchardt, P. K. (1989). Stability of pharmaceutical proteins. *Pharmaceutical Research.* 6:903-918.

McAleer, W. J., Markus, H. Z., McLean, A. A., Buynak, E. B. and Hilleman, M. R. (1980). Stability on storage at various temperatures of live measles, mumps and rubella virus vaccines in new stabilizer.

Middaugh, C. R. (1996). Formulation and delivery of biopharmaceuticals. *Journal of Pharmaceutical Sciences.* 85:1259-1260.

Moss, W. J. and Griffin, D. E. (2006). Global measles elimination. *Nature Review Microbiology.* 4: 900-908.

Nakhasi, H. L., Cao, X., Rouault, T. A. and Liu, T. (1991). Specific binding of host cell proteins to the 3'-terminal stem-loop structure of rubella virus negative-strand RNA. *Journal of Virology.* 5961-5967.

Ohtake, S., Arakawa, T. and Koyama, A. H. (2010). Arginine as a Synergistic Virucidal Agent. *Molecules.* 15: 1408-1424.

Packer, L., Colowick, S. P. and Kaplan, N. O. (2002). Methods in enzymology. Ed. Packer, L. Academic Press, California, USA. Volume 349.

Pritchard, E., Szybala, C., Boison, D., and Kaplan, D. L. (2010). Silk fibroin encapsulated powder reservoirs for sustained release of adenosine. *Journal of Controlled Release.* 144 (2): 159-167.

Rexroad, J., Evans, R. K. and Middaugh, C. R. (2006). Effect of pH and ionic strength on the physical stability of adenovirus type 5. *Journal of Pharmaceutical Sciences.* 95: 1469, 1479.

Roberts, C. J. (2007). Non-Native Protein Aggregation Kinetics. *Biotechnology and Bioengineering.* 98 (5): 927-938.

Russell, B., Selzer, G. and Goetze, H. (1967). The Particle size of rubella virus. *Journal of General Virology.* 1: 305-310.

Schalk, J. A. C., de Vries, C. G. J. C. A, and Jongen, P. M. J. M. (2005). Potency estimation of measles, mumps and rubella trivalent vaccines with quantitative PCR infectivity assay. *Biologicals.* 33: 71-79

Tsioris, K., Raja, W. K., Pritchard, E. M., Panilaitis, B., Kaplan, D. L. and Omenetto, F. G. (2011). Fabrication of silk microneedles for controlled-release drug delivery. *Advanced Functional Materials.* Published online: Dec. 2, 2011.

Vepari, C. and Kaplan, D. L. (2007). Silk as a biomaterial. *Progress in Polymer Science.* 32 (8-9): 991-1007.

Wang, X., Yucel, T., Lu, Q., Hu, X. and Kaplan, D. L. (2010). Silk nanospheres and microspheres from silk/pva blend films for drug delivery. *Biomaterials.* 31: 1025-1035.

Wang, X., Zhang, X, Castellot, J., Herman, I., Iafrati, M. and Kaplan, D. L. (2008). Controlled release from multilayer silk biomaterial coatings to modulate vascular cell responses. *Biomaterials.* 29: 894-903.

Watemran, K. and Adami, R. C. (2005). Accelerated aging: Prediction of chemical stability of pharmaceuticals. *International Journal of Pharmaceutics.* 293: 101-125.

Wightman, G., Beard, J. and Allison, R. (2007). An investigation into the behaviors of air rifle pellets in ballistic gel and their interaction with bone. *Forensic Science International.* 200 (1-3): 41-49.

WHO. (1982). Report of Expert Committee on Biological Standardization. Thirty-second report. Requirement for measles vaccine (live). Addendum 1981, Geneva, World Health Organization. (Technical Report Series no. 673, Annex 6).

WHO. (1994). Report of Expert Committee on Biological Standardization. Requirements for measles, mumps and rubella vaccines and combined vaccines (live). Geneva, World Health Organization. (Technical Report Series, No. 840, Annex 39).

WHO (2006). Temperature sensitivity of vaccines. WHO publications. [Online]. The reference can be accessed at whqlibdoc.who.int/hq/2006/WHO_IVB_06.10_eng.pdf WHO. (2011). Measles. Media centre fact sheet No 286. October 2011. [Online]. The reference can be accessed at who.int/mediacentre/factsheets/fs286/en/

WHO, UNAIDA, World Bank, UNESCO, UNFPA (2000). Health: a key to prosperity. In: Success Stories in Developing Countries. World Health Organization, Geneva.

Wild, T. F., Malvoisin, E. and Buckland, R. (1991). Measles virus: both the haemagglutinin and fusion glycoproteins are required for fusion. *Journal of General Virology.* 72: 439-442.

Woelk, C. H., Pybus, O. G., Jin, L., Brown, D. W. G. and Holmes, E. C. (2002). Increased positive selection pressure in persistent (SSPE) versus acute measles virus infections. *Journal of General Virology.* 83: 1419-1430.

Wolfson, L. J., Gasse, F., Lee-Martin, S., Lydon, P., Magan, A., Tibouti, A., Johns, B., Hutubessy, R., Salama, P. and Okwo-Bele, J. (2008). Estimating the costs of achieving the WHO-UNICEF Global Immunization Vision and Strategy, 2006-2015. *Bulletin of the World Health Organization.* 86: 27-39.

Worrall, E. E., Litamoi, J. K., Seek, B. M. and Ayelet, G. (2001). Xerovac: an ultra-rapid method for the dehydration and preservation of live attenuated Rinderpest and Peste des Petits ruminants vaccines. *Vaccine.* 19: 834-839.

Zhou, D., Porter, W. R. and Zhang, G. G. Z. (2009). Chapter 5-Drug stability and degradation studies. Developing Solid Oral Dosage Forms: Pharmaceutical Theory and Practice. Ed: Qiu, Y., Chen, Y., Zhang, G. G. Z., Liu, L. and Porter, W. R. Pg: 87-124.

Zweig, S. E. (2006). Advances in vaccine stability monitoring technology. *Vaccine.* 24: 5977-5985.

What is claimed is:

1. A storage-stable composition comprising a silk fibroin film, particle, or microneedle and an active agent distributed therein, wherein the active agent is a vaccine, wherein administering the composition to a subject initiates sustained release of the active agent over a period of at least 1 hour; and the active agent retains at least about 30% of its original bioactivity when the composition is (a) subjected to at least one freeze-thaw cycle, or (b) maintained for at least about 24 hours at a temperature above 0° C., or (c) both (a) and (b).

2. The storage-stable composition of claim 1, wherein the active agent retains at least about 30% of its original bioactivity when the composition is (a) subjected to at least one freeze-thaw cycle, and (b) maintained for at least about 24 hours at a temperature above 0° C.

3. The storage-stable composition of claim 1, wherein the active agent retains at least about 60% of its original bioactivity when the composition is (a) subjected to at least one freeze-thaw cycle, or (b) maintained for at least about 24 hours at a temperature above 0° C., or (c) both (a) and (b).

4. The storage-stable composition of claim 1, wherein the active agent retains at least about 60% of its original bioactivity when the composition is (a) subjected to at least one freeze-thaw cycle, and (b) maintained for at least about 24 hours at a temperature above 0° C.

5. The storage-stable composition of claim 1, the composition further comprising a stabilizing agent selected from the group consisting of a saccharide, a sugar alcohol, an ion, a surfactant, and combinations thereof.

6. The storage-stable composition of claim 5, wherein the stabilizing agent is a saccharide.

7. The storage-stable composition of claim 6, wherein the saccharide is sucrose.

8. The storage-stable composition of claim 5, wherein the stabilizing agent is a sugar alcohol.

9. The storage-stable composition of claim 8, wherein the sugar alcohol is sorbitol or mannitol.

10. The storage-stable composition of claim 1, wherein the vaccine comprises an antigenic molecule that when introduced into the subject's body produces immunity to a specific disease by causing the activation of the immune system, antibody formation, and/or creating of a T-cell and/or B-cell response.

11. The storage-stable composition of claim 1, wherein the vaccine is a live, attenuated virus or an inactivated virus.

12. The storage-stable composition of claim 11, wherein the live, attenuated virus or inactivated virus is chosen from a measles virus, a mumps virus, a rubella virus, a varicella virus, a flavivirus, a yellow fever virus, an influenza virus, a rotavirus, a reovirus, a hepatitis virus, a rabies virus, and a poliovirus.

13. The storage-stable composition of claim 11, wherein the live, attenuated virus or the inactivated virus shows an increased half-life of at least about 1.5-fold at a temperature of at least about 20° C., compared to the live, attenuated virus or the inactivated virus without the silk fibroin film, particle, or microneedle.

14. The storage-stable composition of claim 1, wherein the original bioactivity is original immunogenicity.

15. The storage-stable composition of claim 14, wherein the vaccine retains at least 30% of its original immunogenicity after the composition is maintained at 4° C. for 4 weeks.

16. The storage-stable composition of claim 1, wherein the original bioactivity is original infectivity.

17. The storage-stable composition of claim 16, wherein the vaccine retains at least 30% of its original infectivity for at least about 24 hours at a temperature of at least about room temperature or higher.

18. The storage-stable composition of claim 1, wherein the silk fibroin film, particle, or microneedle comprises a silk fibroin concentration of about 0.5% w/v to about 20% w/v.

19. The storage-stable composition of claim 1, wherein the silk fibroin film, particle, or microneedle is in an air-dried, nitrogen-dried, or lyophilized form.

20. The storage-stable composition of claim 1, wherein the composition is formulated for transdermal delivery.

21. The storage-stable composition of claim 1, wherein the composition is implantable.

22. The storage-stable composition of claim 1, wherein the composition has a residual moisture that is adapted to provide storability such that the active agent retains at least about 30% of its original bioactivity when the composition is (a) subjected to at least one freeze-thaw cycle, or (b)

maintained for at least about 24 hours at a temperature above 0° C., or (c) both (a) and (b).

23. The storage-stable composition of claim 1, which is a microneedle.

24. The storage-stable composition of claim 23, wherein the microneedle is configured to puncture the skin of a subject and release the vaccine subcutaneously.

25. The storage-stable composition of claim 24, wherein the microneedle is configured to release the vaccine by dissolving.

26. A storage-stable composition comprising a silk fibroin film, particle, or microneedle and an active agent distributed therein, the active agent is a vaccine having a bioactivity that is reduced upon being subjected to either at least one freeze-thaw cycle or maintenance for at least 24 hours at a temperature of above 0° C. in the absence of the silk fibroin film, particle, or microneedle, the composition having a residual moisture that is adapted to provide storage stability such that the active agent has at least about 30% greater bioactivity relative to the active agent in the absence of the silk fibroin film, particle, or microneedle when the composition or the at least one active agent in the absence of the silk fibroin film, particle, or microneedle is (a) subjected to at least one freeze-thaw cycle, or (b) maintained for at least about 24 hours at a temperature of above 0° C., or (c) both (a) and (b), and wherein administering the composition to a subject initiates sustained release of the active agent over a period of at least 1 hour.

\* \* \* \* \*